(12) United States Patent
Lee et al.

(10) Patent No.: US 9,216,977 B2
(45) Date of Patent: Dec. 22, 2015

(54) ANTOFINE AND CRYPTOPLEURINE DERIVATIVES AS ANTICANCER AGENTS

(75) Inventors: Kuo-Hsiung Lee, Chapel Hill, NC (US); Xiaoming Yang, Chapel Hill, NC (US); Qian Shi, Chapel Hill, NC (US); Kenneth F. Bastow, Chapel Hill, NC (US); Che-Ming Teng, Taipei (TW); Tse-Ming Hong, Taipei (TW); Pan-Chyr Yang, Taipei (TW); Shuenn-Chen Yang, Taipei (TW)

(73) Assignees: The University of North Carolina at Chapel Hill, Chapel Hill, NC (US); National Taiwan University, Taipei (TW)

( * ) Notice: Subject to any disclaimer, the term of this patent is extended or adjusted under 35 U.S.C. 154(b) by 374 days.

(21) Appl. No.: 13/503,113

(22) PCT Filed: Sep. 22, 2010

(86) PCT No.: PCT/US2010/049780
§ 371 (c)(1),
(2), (4) Date: Jul. 24, 2012

(87) PCT Pub. No.: WO2011/049704
PCT Pub. Date: Apr. 28, 2011

(65) Prior Publication Data
US 2012/0283220 A1 Nov. 8, 2012

Related U.S. Application Data

(60) Provisional application No. 61/253,966, filed on Oct. 22, 2009.

(51) Int. Cl.
| A61K 31/4355 | (2006.01) |
| A61K 31/436 | (2006.01) |
| A61K 31/4375 | (2006.01) |
| C07D 471/04 | (2006.01) |
| C07D 491/12 | (2006.01) |
| C07D 491/04 | (2006.01) |

(52) U.S. Cl.
CPC ............ *C07D 471/04* (2013.01); *C07D 491/04* (2013.01)

(58) Field of Classification Search
CPC ............ A61K 31/4355; A61K 31/436; A61K 31/4375; C07D 471/04; C07D 491/12
USPC ................... 514/279, 280; 546/38, 41, 58, 59
See application file for complete search history.

(56) References Cited

U.S. PATENT DOCUMENTS

| 4,171,366 | A | 10/1979 | Blattner et al. |
| 2005/0222418 | A1 | 10/2005 | Baker et al. |
| 2008/0300254 | A1 | 12/2008 | Lee et al. |

FOREIGN PATENT DOCUMENTS

| CN | 101189968 A | 11/2006 |
| CN | 101189968 | * 6/2008 |

OTHER PUBLICATIONS

Luo et al., Cytotoxic Alkaloids From Boehmeria Siamensis, Planta Medica, vol. 69, No. 9, pp. 842-845, 2003.*
Wang et al., Highly Efficient Synthesis of Phenanthroquinolizidine Alkaloids via Parham-type Cycliacylation, Tetrahedron Letters, vol. 51, No. 10, pp. 1377-1379, 2010.*
Gao W et al. Structural analogs of tylophora alkaloids may not be functional analogs. Bioorg Med Chem Lett. Jan. 15, 2008; 18(2): 704-709.
Chemler SR. Phenanthroindolizidines and phenanthroquinolizidines: promising alkaloids for anti-cancer therapy. Current Bioactive Compounds. Feb. 5, 2009; 5(1): 2-19.
Yang X et al. Antitumor agents 274. a new synthetic strategy for E-ring SAR study of antofine and cryptopleurine analogs. Org Lett. Apr. 2, 2010; 12(7): 1416-1419.
International Search Report and Written Opinion, PCT/US10/49780, mailed Oct. 29, 2010.

* cited by examiner

*Primary Examiner* — Brenda Coleman
(74) *Attorney, Agent, or Firm* — Myers Bigel Sibley & Sajovec, P.A.

(57) ABSTRACT

The present invention provides compounds of Formula (I-IV): compositions containing the same, and methods of use thereof such as for the treatment of cancer.

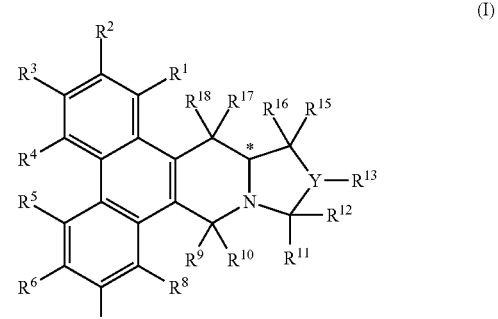

(I)

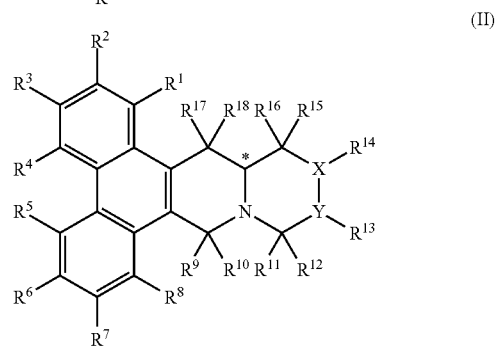

(II)

-continued
(III)
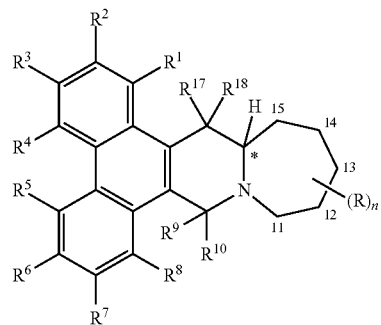
(IV)
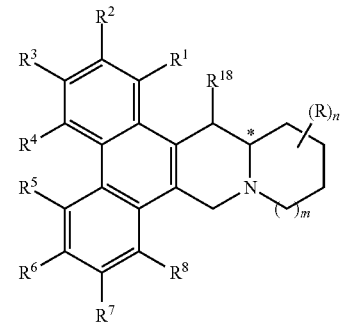
11 Claims, No Drawings

ANTOFINE AND CRYPTOPLEURINE DERIVATIVES AS ANTICANCER AGENTS

RELATED APPLICATIONS

This application is a 35 U.S.C. §371 national phase entry of PCT Application PCT/US2010/049780, filed Sep. 22, 2010, and published in English on Apr. 28, 2011, as International Publication No. WO 2011/049704, and which claims the benefit under 35 U.S.C. §119(e) of U.S. Provisional Patent Application Ser. No. 61/253,966, filed Oct. 22, 2009, the disclosure of each of which is incorporated herein by reference in its entirety.

STATEMENT OF GOVERNMENT SUPPORT

This invention was made with government support under grant number CA 17625 awarded by the National Institutes of Health. The United States Government has certain rights to this invention.

FIELD OF THE INVENTION

The present invention concerns antofine and cryptopleurine analogs as active compounds and methods of use thereof, particularly in methods of treating cancer.

BACKGROUND OF THE INVENTION

Phenanthroindolizidines and phenanthroquinolizidines are a series of plant-derived natural alkaloids primarily found in the Asclepiadaceae and Moracea plant family. The leaves of these plants have been used to treat a number of diseases such as asthma, bronchitis, and rheumatism etc. since ancient times.[1,2] Such interesting characteristics inevitably prompted scientists to identify the major therapeutic components in these plants, which led to the discovery of a series of bioactive natural products. To date, over sixty compounds have been isolated and characterized. R-tylophorine, R-antofine, and R-cryptopleurine (Scheme A) are well known representatives in the family that have been reported to have potent antitumor activity.[3] Recently, an antitumor screening program launched by National Cancer Institute (NCI) has rekindled our interests in these compounds and greatly fascinated the progress of research in the discovery and development of more potent antitumor phenanthroindolizidines and phenanthroquinolizidines. However, the facts of low natural abundance and availability have prohibited researchers from discovering more exciting therapeutic candidates efficiently; therefore, total synthesis has been considered an effective approach to take place.

Scheme A: Representative structures of phenathroindolizidines and phenanthroquinolizidines

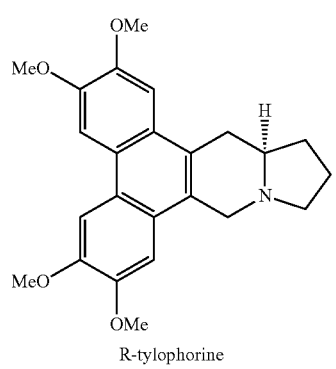

R-tylophorine

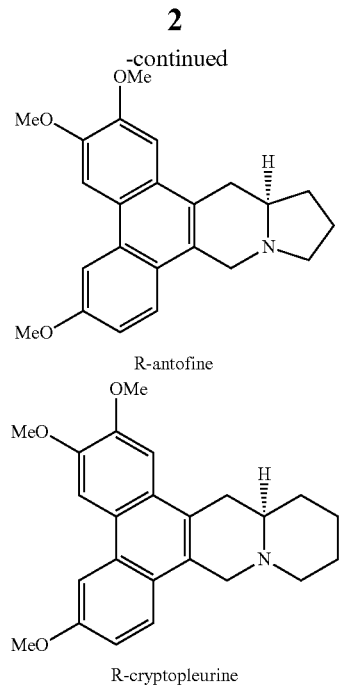

R-antofine

R-cryptopleurine

One major side effect prohibiting the use of natural alkaloids as therapeutic agents is their severe CNS toxicity, such as disorientation and ataxia.[10] Analogs with higher polarity may be desirable to manipulate such side effects by preventing them from entering the blood brain barrier. Although a number of synthetic pathways to racemates or single isomers have been reported, to date, only a few polar antofine analogs with a C14-OH group have been synthesized and reported to have better antitumor activity in vivo compared with their natural counterparts; however, their activity in vitro was lower.[11] More phenanthroindolizidines and phenanthroquinolizidines analogs with diverse structural features are urgently needed to extensively study the biological properties, especially antitumor activities. Previous methodologies to achieve these polar or non-polar active phenanthroindolizidine and phenanthroquinolizidine analogs all focused on modifications on rings -A, -C, and -D. There has been no synthetic method reported by far for making analogs with modifications on the ring-E, especially with practically versatile, efficient, and facile E-ring-derivatized advancements.

SUMMARY OF THE INVENTION

A first aspect of the present invention is a compound having a structure according to Formula I-IV:

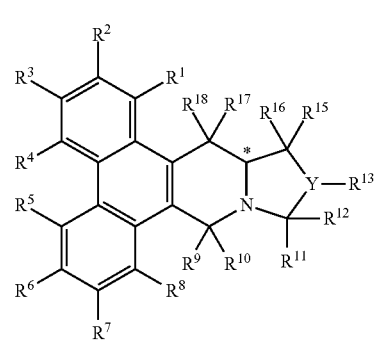

(I)

-continued

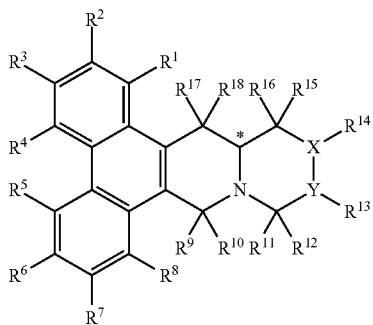

(II)

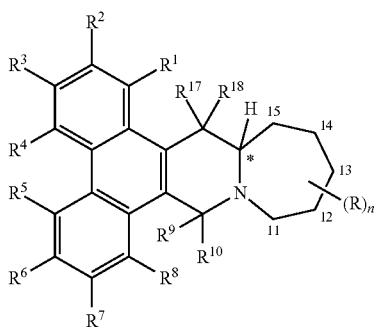

(III)

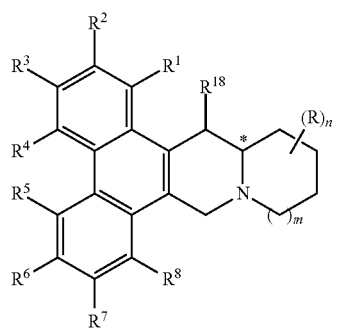

(IV)

wherein:

X and Y are each independently selected from CH, nitrogen, oxygen or sulfur atom;

optionally but preferably (particularly in the case of Formulas I, II and III) such that at least one of X or Y is nitrogen, oxygen or sulfur atom;

$R^1$, $R^2$, $R^3$, $R^4$, $R^5$, $R^6$, $R^7$ and $R^8$ are each independently selected from the group consisting of H, halo, hydroxy, amino, substituted amino, alkoxy, alkylthio, loweralkyl, loweralkenyl and loweralkynyl;

or, $R^2$ and $R^3$, or $R^5$ and $R^6$, or $R^6$ and $R^7$ are independently connected through an alkyldioxy, alkenyldioxy, alkylene or alkenylene bridge;

each $R^9$, $R^{10}$, $R^{11}$, $R^{12}$, $R^{15}$, $R^{16}$, $R^{17}$, $R^{18}$, and R are independently selected from the group consisting of H, hydroxyl, alkoxy, alkylthio, loweralkyl, loweralkenyl, loweralkynyl, alkoyl, loweralkoyl, loweralkenoyl and amino;

n is 0-5;

m is 0, 1 or 2; and $R^{13}$ and $R^{14}$ are each independently selected from the group consisting of H, hydroxyl, alkoxy, loweralkyl, loweralkenyl, loweralkynyl, alkoyl, loweralkoyl, loweralkenoyl, alkylsulfonyl, substituted amino, substituted phosphoryl, substituted aminocarbonyl, cycloalkyl and heterocycloalkyl;

or a pharmaceutically acceptable salt thereof.

R is substituted at position(s) 11, 12, 13, 14 or 15 and n is 0, 1, 2, 3, 4 or 5.

In some embodiments, at least one of $R^1$, $R^2$, $R^3$, $R^4$, $R^5$, $R^6$, $R^7$ or $R^8$ is alkoxy.

A further aspect of the present invention is a new synthetic methodology to prepare an active compound as described herein.

A still further aspect of the present invention is a pharmaceutical formulation comprising an active compound as described herein, in a pharmaceutically acceptable carrier (e.g., an aqueous carrier).

A still further aspect of the present invention is a method of treating a cancer, comprising administering to a human or animal subject in need thereof a treatment effective amount (e.g., an amount effective to treat, slow the progression of, etc.) of an active compound as described herein. Examples of cancers that may be treated include, but are not limited to, skin cancer, lung cancer including small cell lung cancer and non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

A still further aspect of the present invention is the use of an active compound as described herein for the preparation of a medicament for carrying out a method of treatment.

DETAILED DESCRIPTION OF THE INVENTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

"Moiety" and "group" are used interchangeably herein to refer to a portion of a molecule, typically having a particular functional or structural feature, e.g. a linking group (a portion of a molecule connecting two other portions of the molecule).

The term "substituted" as used herein to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" as used herein references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include but are not limited to alkyl, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, and modified lower alkyl.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkylene" as used herein refers to an alkyl chain.

"Alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Loweralkenyl" as used herein, is a subset of alkenyl and refers to a straight or branched chain hydrocarbon group containing from 2 to 4 carbon atoms.

"Alkenylene" as used herein refers to an alkenyl chain.

"Alkynyl" as used herein refers to a straight or branched chain hydrocarbon containing from 2 to 10 carbons and containing at least one carbon-carbon triple bond formed by the removal of three hydrogens. Representative examples of "alkynyl" include, but are not limited to, ethyne, propyne, 1-butyne, 2-butyne and the like. "Lower alkynyl" as used herein, is a subset of alkynyl and refers to a straight or branched chain hydrocarbon group containing from 2 to 4 carbon atoms.

"Alkyldioxy" as used herein refers to a molecular segment having the structure —O—R—O—, wherein the molecular segment is appended to the parent molecular moiety through the oxy groups, as defined herein, and R is an alkyl group, as defined herein.

"Alkenyldioxy" as used herein refers to a molecular segment having the structure —O—R—O—, wherein the molecular segment is appended to the parent molecular moiety through the oxy groups, as defined herein, and R is an alkenyl group, as defined herein.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

"Alkylsulfonyl" as used herein refers to a group of formula —S(O)$_2$-alkyl, wherein the alkyl group is as defined herein. The alkyl group is appended to the parent molecular moiety through the sulfonyl group.

"Alkylthio" as used herein refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Alkoyl" as used herein refers to a molecular segment having the structure —CO-alkyl, wherein alkyl is as defined herein and the alkyl group is appended to the parent molecular moiety through the carbonyl group. "Loweralkoyl" as used herein is a subset of alkoyl and refers to an alkoyl group where the alkyl is a loweralkyl as defined herein.

"Alkenyl" as used herein refers a molecular segment having the structure —CO-alkenyl, wherein alkenyl is as defined herein and the alkenyl group is appended to the parent molecular moiety through the carbonyl group. "Loweralkenoyl" as used herein is a subset of alkenoyl and refers to an alkenoyl group where the alkenyl is a loweralkenyl as defined herein.

"Cycloalkyl," as used herein, refers to a saturated cyclic hydrocarbon group containing from 3 or 4 to 6 or 8 carbons. Representative examples of cycloalkyl include cyclopropyl, cyclobutyl, cyclopentyl, cyclohexyl, cycloheptyl, and cyclooctyl.

"Heterocycle," as used herein, refers to a monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

Heterocycle groups of this invention can be substituted with 1, 2, or 3 substituents, such as substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkoxycarbonyl, arylalkyl, aryloxy, carboxy, cyano, formyl, oxo, halo, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NRR' (wherein, R and R' are independently selected from hydrogen, alkyl, aryl, and arylalkyl).

The term "heterocycloalkyl" as used herein refers to heterocyclic versions of "alkyl." Additionally, for heterocycloalkyl, a heteroatom can occupy the position at which the heterocycle is attached to the remainder of the molecule. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

"Aryl" as used herein refers to an aromatic species containing 1 to 5 aromatic rings, either fused or linked, and either unsubstituted or substituted with 1 or more typically selected from the group consisting of lower alkyl, modified lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azido, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic.

"Halo" as used herein refers to any halogen group, such as chloro, fluoro, bromo, or iodo.

"Hydroxyl" as used herein refers to a —OH moiety.

"Oxo" as used herein, refers to a =O moiety.

"Oxy," as used herein, refers to a —O— moiety.

"Thio" as used herein refers to a —S— moiety.

"Amine" or "amino" is intended to mean the radical —NH$_2$.

"Substituted amino" or "substituted amine" refers to an amino group, wherein one or two of the hydrogens are replaced by a suitable substituent. Disubstituted amines may have substituents that are bridging, i.e., forming a heterocyclic ring structure that includes the amine nitrogen as the linking atom to the parent compound. Examples of substituted amines include but are not limited to alkylamino, dialkylamino, and heterocyclo (where the heterocyclo is linked to the parent compound by a nitrogen atom in the heterocyclic ring or heterocyclic ring system).

"Alkylamino" is intended to mean the radical —NHR', where R' is alkyl.

"Dialkylamino" is intended to mean the radical NR'R", where R' and R" are each independently an alkyl group.

"Substituted aminocarbonyl" as used herein refers to the molecular segment having the structure —CONR'R", wherein this molecular segment is connected to the parent molecular moiety through the carbonyl group and R' and R" are substituents as described herein.

"Substituted phosphoryl" as used herein refers to the molecular segment having the structure —POR'R", wherein this molecular segment is connected to the parent molecular moiety through the phosphoryl group and R' and R" are substituents as described herein.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Treatment effective amount" as used herein refers to an amount of the active compound effective to treat the disease, slow the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

The present invention is concerned primarily with the treatment of human subjects, but may also be employed for the treatment of other animal subjects (i.e., mammals such as dogs, cats, horses, etc. or avians) for veterinary purposes. Mammals are preferred, with humans being particularly preferred.

A. Active Compounds.

Active compounds of the present invention are, in general, compounds of Formula I-IV:

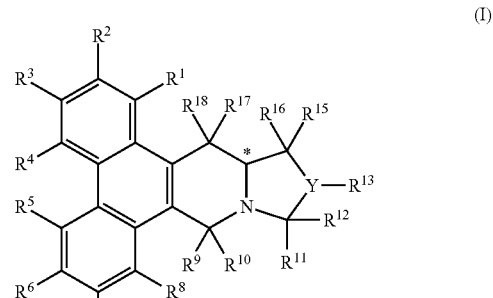

(I)

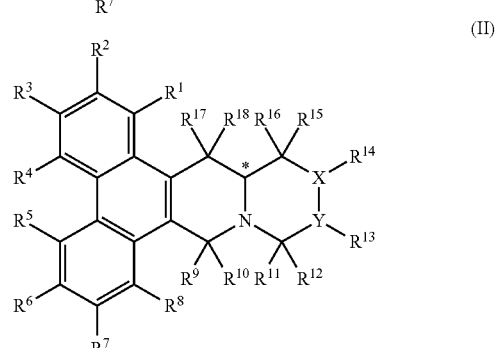

(II)

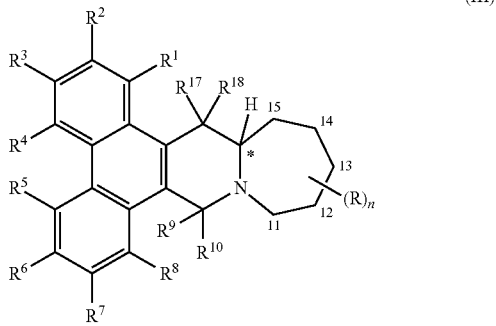

(III)

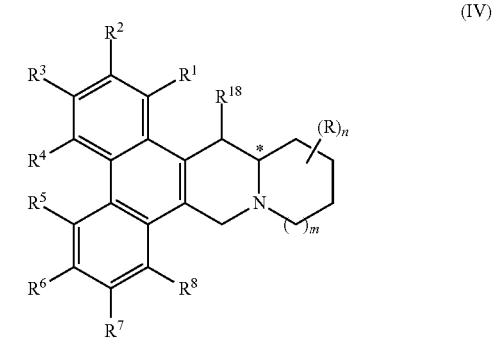

(IV)

wherein:

X and Y are each independently selected from CH, nitrogen, oxygen or sulfur atom; optionally but preferably (particularly in the case of Formulas I, II or III) such that at least one of X or Y is nitrogen, oxygen or sulfur atom;

$R^1$, $R^2$, $R^3$, $R^4$, $R^5$, $R^6$, $R^7$ and $R^8$ are each independently selected from the group consisting of H, halo, hydroxy, amino, substituted amino, alkoxy, alkylthio, loweralkyl, loweralkenyl and loweralkynyl;

or, $R^2$ and $R^3$, or $R^5$ and $R^6$, or $R^6$ and $R^7$ are independently connected through an alkyldioxy, alkenyldioxy, alkylene or alkenylene bridge;

each $R^9$, $R^{10}$, $R^{11}$, $R^{12}$, $R^{15}$, $R^{16}$, $R^{17}$, $R^{18}$ and R are independently selected from the group consisting of H, hydroxyl, alkoxy, alkylthio, loweralkyl, loweralkenyl, loweralkynyl, alkoyl, loweralkoyl, loweralkenoyl and amino;

n is 0-5;

m is 0, 1 or 2: and $R^{13}$ and $R^{14}$ are each independently selected from the group consisting of H, hydroxyl, alkoxy, loweralkyl, loweralkenyl, loweralkynyl, alkoyl, loweralkoyl, loweralkenoyl, alkylsulfonyl, substituted amino, substituted phosphoryl, substituted aminocarbonyl, cycloalkyl and heterocycloalkyl;

or a pharmaceutically acceptable salt thereof.

R is substituted at position(s) 11, 12, 13, 14 or 15 and n is 0, 1, 2, 3, 4 or 5.

More particular examples of compounds of Formula I include Formula Ia:

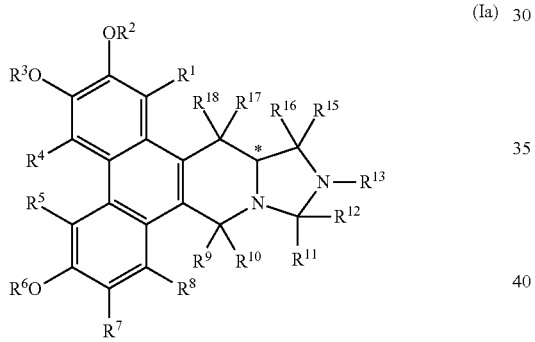

(Ia)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, $R^{17}$, and $R^{18}$ are as given above; or a pharmaceutically acceptable salt thereof.

More particular examples of compounds of Formula II include compounds of Formula IIa, Formula IIb, Formula IIc, and Formula IId:

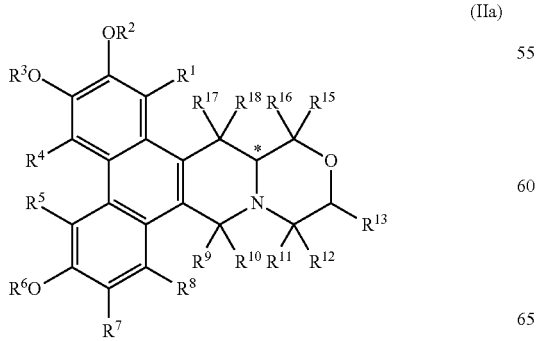

(IIa)

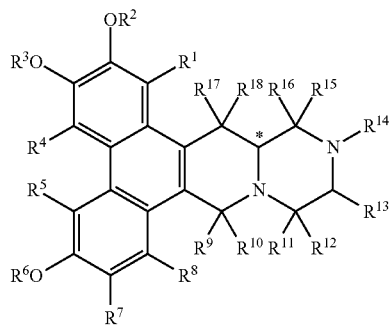

(IIb)

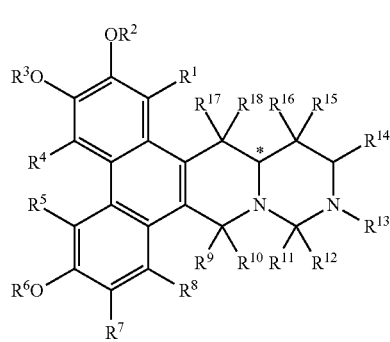

(IIc)

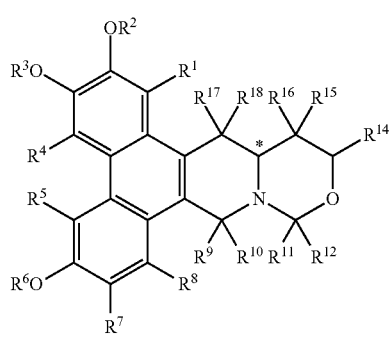

(IId)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are as given above; or a pharmaceutically acceptable salt thereof.

In some embodiments of the foregoing, $R^2$ and $R^3$ are both alkyl, such as methyl or ethyl, or both together are a methylene group.

In some embodiments of the foregoing, $R^6$ is alkyl, such as methyl or ethyl.

More particular examples of compounds of Formula III include compounds of Formula IIIa:

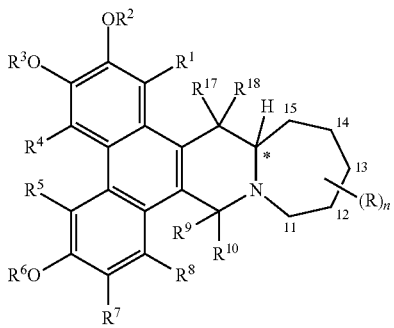

wherein $R^1$, $R^2$, $R^3$, $R^4$, $R^5$, $R^6$, $R^7$, $R^8$, $R^9$, $R^{10}$, $R^{17}$, $R^{18}$, and each R are each independently selected as given above and n is 0, 1, 2, 3, 4 or 5; or a pharmaceutically acceptable salt thereof.

More particular examples of compounds of Formula IV include compounds of Formula IVa:

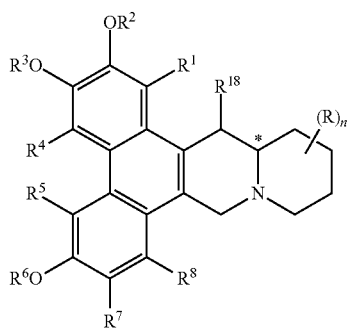

wherein $R^1$, $R^2$, $R^3$, $R^4$, $R^5$, $R^6$, $R^7$, $R^8$, $R^{18}$, and each R are each independently selected as given above and n is 0, 1, 2, 3, 4 or 5; or a pharmaceutically acceptable salt thereof.

In some embodiments, particular preferred examples of substituents $R^2$, $R^3$, and $R^6$ are methyl;

for some embodiments of Formula Ia, $R^1$, $R^4$, $R^5$, $R^7$, $R^8$, $R^9$, $R^{10}$, $R^{11}$, $R^{12}$, $R^{15}$, $R^{16}$, $R^{17}$, and $R^{18}$ are H and $R^{13}$ is methyl;

for some embodiments of Formula IIa, $R^1$, $R^4$, $R^5$, $R^7$, $R^8$, $R^9$, $R^{10}$, $R^{11}$, $R^{12}$, $R^{13}$, $R^{15}$, $R^{16}$, $R^{17}$, and $R^{18}$ are H;

for some embodiments of Formula IIb, $R^1$, $R^4$, $R^5$, $R^7$, $R^8$, $R^9$, $R^{10}$, $R^{11}$, $R^{12}$, $R^{13}$, $R^{15}$, $R^{16}$, $R^{17}$, and $R^{18}$ are H and $R^{14}$ is dimethoxyphosphoryl or cyclopropylmethyl;

for some embodiments of Formula IIc, $R^1$, $R^4$, $R^5$, $R^7$, $R^8$, $R^9$, $R^{10}$, $R^{11}$, $R^{12}$, $R^{14}$, $R^{15}$, $R^{16}$, $R^{17}$, and $R^{18}$ are H and $R^{13}$ is dimethylamino;

for some embodiments of Formula IId, $R^1$, $R^4$, $R^5$, $R^7$, $R^8$, $R^9$, $R^{10}$, $R^{11}$, $R^{12}$, $R^{14}$, $R^{15}$, $R^{16}$, $R^{17}$, and $R^{18}$ are H; and for some embodiments of Formula IIIa, $R^1$, $R^4$, $R^5$, $R^7$, $R^8$, $R^9$, $R^{10}$, $R^{17}$, $R^{18}$, and R are H.

for some embodiments of Formula IVa, $R^4$, $R^5$, $R^7$, $R^{18}$ are H and R is hydroxyl or methoxy group.

B. Formulations and Pharmaceutically Acceptable Salts.

The term "active agent" as used herein refers to the compounds of Formula I, Formula II and Formula III as well as pharmaceutically acceptable salts of these compounds. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base. Because the free base of the compound is less soluble than the salt, free base compositions are employed to provide more sustained release of the active agent to the target area. Active agent present in the target area which has not gone into solution is not available to induce a physiological response, but serves as a depot of bioavailable drug which gradually goes into solution.

The compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth, and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3:318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

C. Methods of Use.

In addition to the compounds of the formulas described herein, the present invention also provides useful therapeutic methods. For example, the present invention provides a method of inducing cytotoxicity against tumor cells, or treating a cancer or tumor in a subject in need thereof.

Cancer cells which may be inhibited include but are not limited to cells from skin cancer, small cell lung cancer, non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of Formula I, Formula II or Formula III as described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLE 1

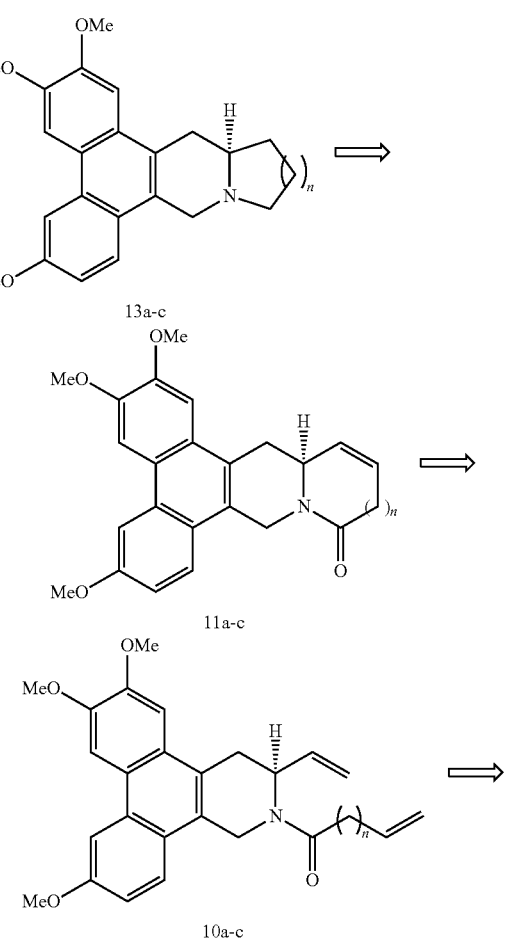

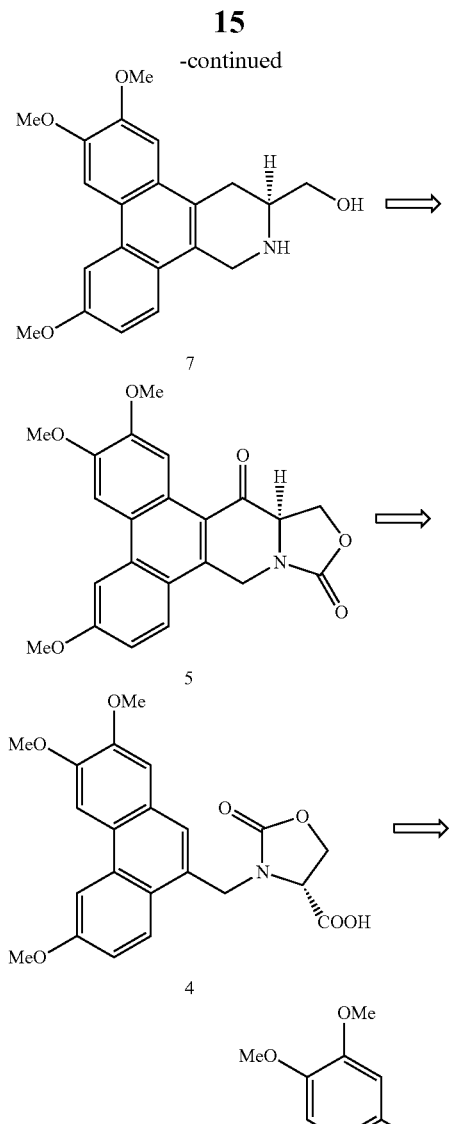

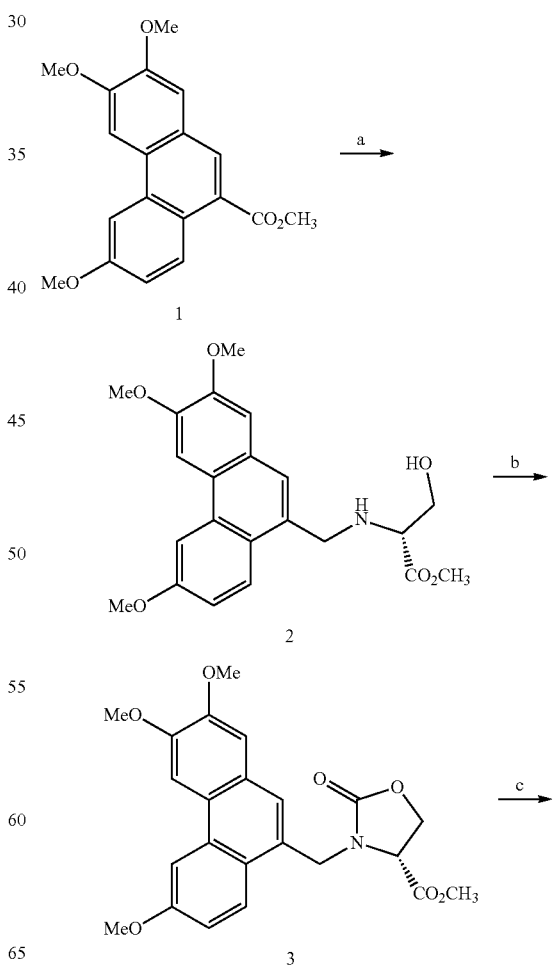

ety of functional groups can be readily introduced during E-ring formation and subsequent reactions.[12] New analogs synthesized with our method might potentially fill in missing SAR information about the alkaloid E ring.

Another novel strategy in this synthesis is related to formation of the D-ring, a piperidine moiety with the N atom at the desired position. This ring is constructed by using an intramolecular acylation assisted by a Lewis acid, such as $SnCl_4$ or $AlCl_3$ (formation of 5 in Scheme 1).[5] However, in order for this intramolecular acylation reaction to occur in high yield, the N atom has to first be present as an amide moiety in a ring system, as neither a tertiary amine nor a non-cyclic amide will provide the desired acylation product efficiently. The 2-oxo-oxazolidine-4-carboxylic acid moiety in compound 4 is such a N source (Scheme 1). In addition, in order to eventually construct a permanent E ring of the desired size into the target compounds, the end ring moiety in 5 should be readily manipulated synthetically. The oxazolidinone system is an ideal moiety and was successfully employed in our synthesis. Not only do the physicochemical properties of oxazolidinone allow it to be easily managed, but in its formation, a chiral center optically identical to the natural products is incorporated into the molecule without using expensive enantioselective catalysts.

The natural product R-antofine has been totally synthesized and reported to have potent antitumor activity. However, its structure-activity relationship (SAR) profile has not been fully explored, because no practical synthetic methodologies are available to make antofine analogs with only slight synthetic manipulation. Thus, one objective in our research was to develop a versatile synthetic methodology by which a series of novel antofine analogs with E-ring modifications could be generated. Our retrosynthetic analysis is outlined in Scheme 1.

In conventional syntheses of phenanthroindolizidine/phenanthroquinolizidine analogs, the E ring was formed prior to the D ring being conjugated to the phenanthrene system. In contrast, in our innovative approach, the E ring is constructed after the D ring has been conjugated. This synthetic strategy has the following merits: the size of the E ring can be easily manipulated via a Grubb's $2^{nd}$ generation catalyst and a vari-

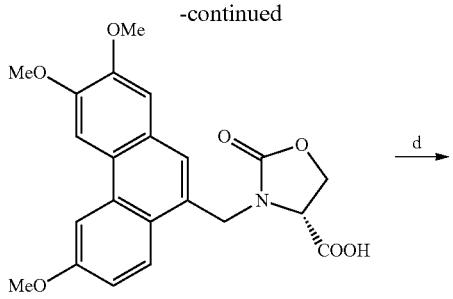

4

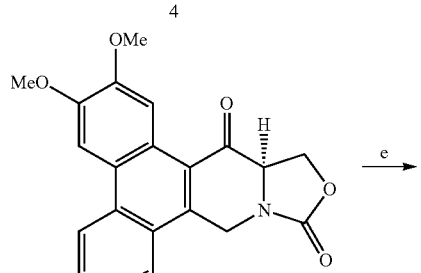

5

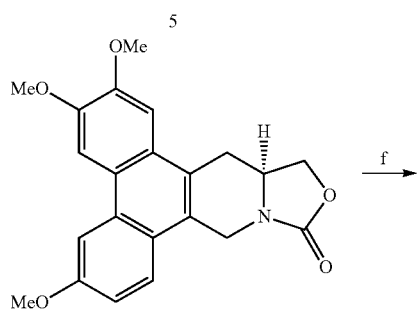

6

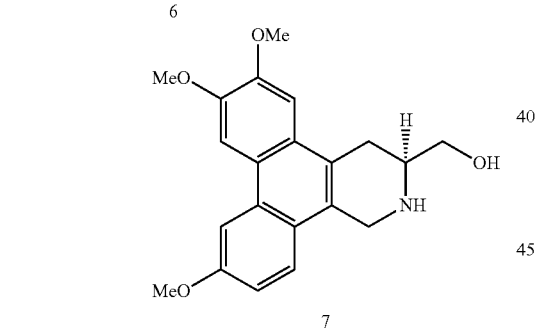

7

Reagents and conditions: (a) i) LiAlH$_4$, THF; ii) Py·SO$_3$, DMSO, CH$_2$Cl$_2$, Et$_3$N; iii) R-serine methyl ester hydrochloride, Et$_3$N, AcOH, NaBH$_3$CN, MeOH (b) Im$_2$CO, CH$_2$Cl$_2$, reflux (c) Dioxane, 2N KOH (d) Oxalyl chloride, DMF, SnCl$_4$, CH$_2$Cl$_2$, 50° C. (e) i) NaBH$_4$, MeOH; ii) Et$_3$SiH, TFA (f) NaOH, MeOH, 100° C.

As shown in Scheme 2, compound 1 was obtained via three steps as reported in the literature in 45% yield.[13] Subsequent reduction with LiAlH$_4$ was followed by oxidization with Py.SO$_3$/DMSO to yield an aldehyde. The resulting aldehyde was reductively aminated by using D-serine methyl ester hydrochloride in the presence of NaBH$_3$CN to give 2 in an overall yield of 59% (three steps). This yield of 2 was improved over the less than 20% yield obtained by direct reaction of serine methyl ester with 9-bromomethylphenanthrene. In addition, the poor solubility of 9-bromomethylphenanthrene in common organic solvents would also be problematic in large-scale reactions. Construction of the oxazolidinone ring system was accomplished by reaction of 2 with Im$_2$CO in CH$_2$Cl$_2$ under reflux to afford 3 in 76% yield.[14] Triphosgene/THF/reflux was tried and found to be sluggish, resulting in a low yield of the target compound 3. The D-ring was formed in two steps: initial hydrolysis of the methyl ester to form the acid 4 and subsequent cyclization aided by SnCl$_4$ and oxalyl chloride to yield 5 in 79% yield. The ester hydrolysis occurred successfully in dioxane under basic conditions without breakage of the oxazolidinone moiety. Compound 6 was obtained from 5 by reduction of ketone to methylene in two steps. The ketone carbonyl group was first reduced in the presence of NaBH$_4$ to a mixture of diastereomeric secondary alcohols, which were further converted to a methylene group (—CH$_2$—) in nearly quantitative yield by using Et$_3$SiH/TFA.[6] Direct reaction of the ketone carbonyl with Et$_3$SiH/TFA, however, failed to afford 6. Treating 6 with 6N NaOH (aq.) in MeOH at reflux temperature overnight, successfully cleaved the oxazolidinone to give the key intermediate 7 in 95% yield. By using the above synthetic strategies, 7 can be easily synthesized on large scale without noticeable racemization as confirmed by NMR.

Scheme 3.

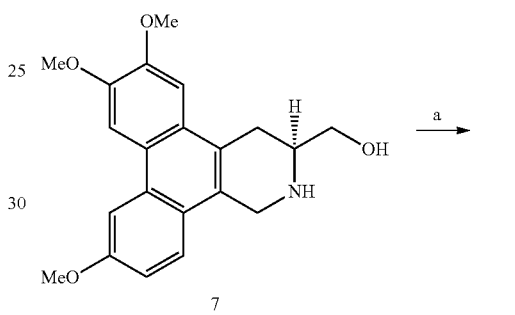

7

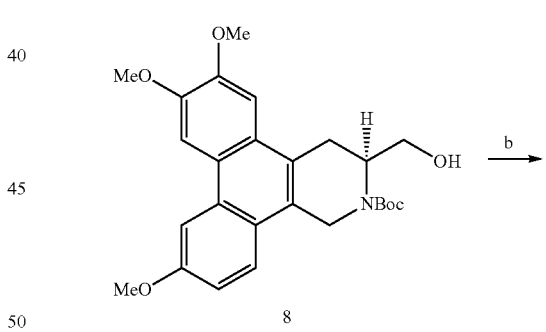

8

9

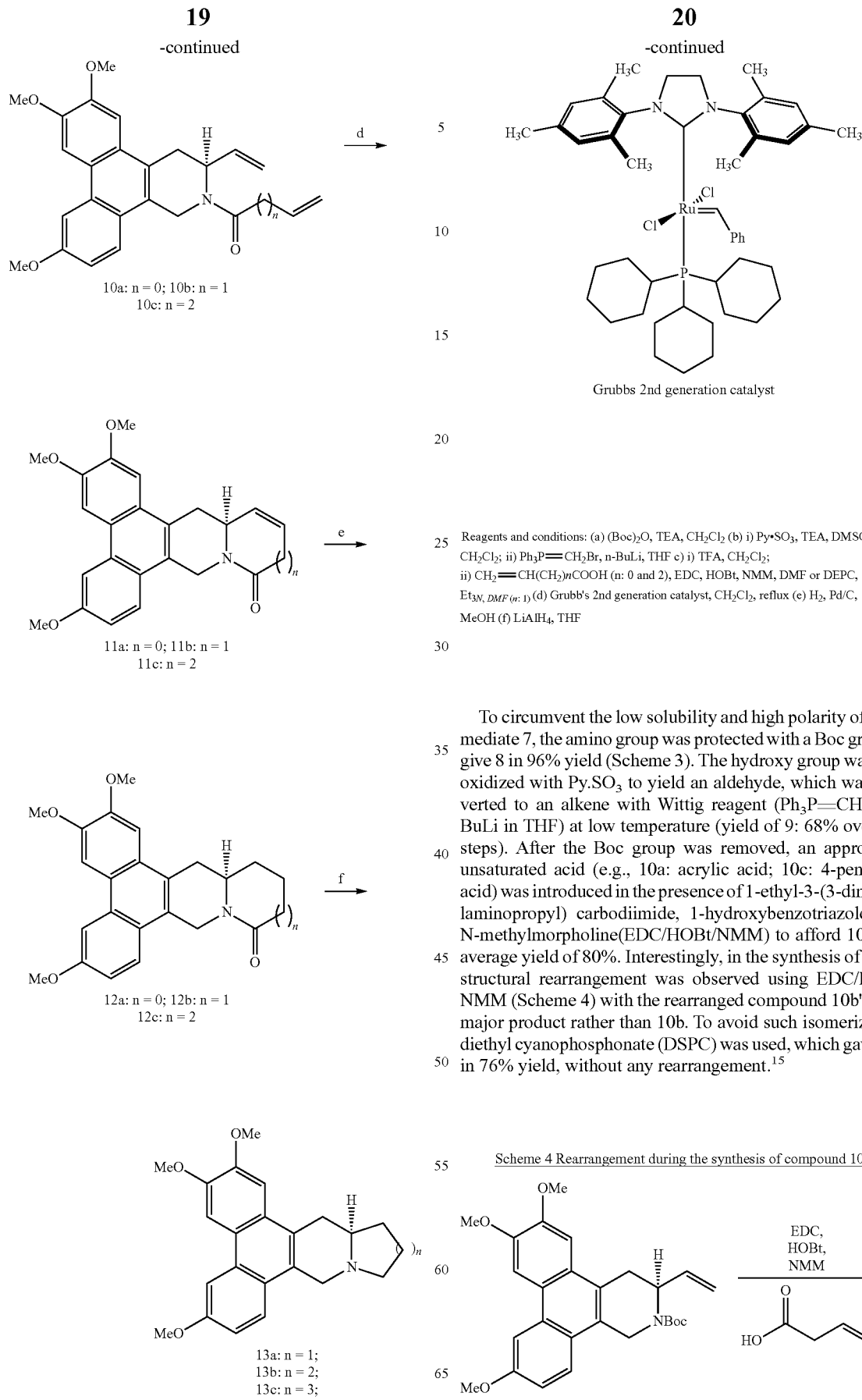

To circumvent the low solubility and high polarity of intermediate 7, the amino group was protected with a Boc group to give 8 in 96% yield (Scheme 3). The hydroxy group was then oxidized with Py.SO₃ to yield an aldehyde, which was converted to an alkene with Wittig reagent (Ph₃P=CH₂Br/n-BuLi in THF) at low temperature (yield of 9: 68% over two steps). After the Boc group was removed, an appropriate unsaturated acid (e.g., 10a: acrylic acid; 10c: 4-pentenoic acid) was introduced in the presence of 1-ethyl-3-(3-dimethylaminopropyl) carbodiimide, 1-hydroxybenzotriazole, and N-methylmorpholine(EDC/HOBt/NMM) to afford 10 in an average yield of 80%. Interestingly, in the synthesis of 10b, a structural rearrangement was observed using EDC/HOBt/NMM (Scheme 4) with the rearranged compound 10b' as the major product rather than 10b. To avoid such isomerization, diethyl cyanophosphonate (DSPC) was used, which gave 10b in 76% yield, without any rearrangement.[15]

Scheme 4 Rearrangement during the synthesis of compound 10b

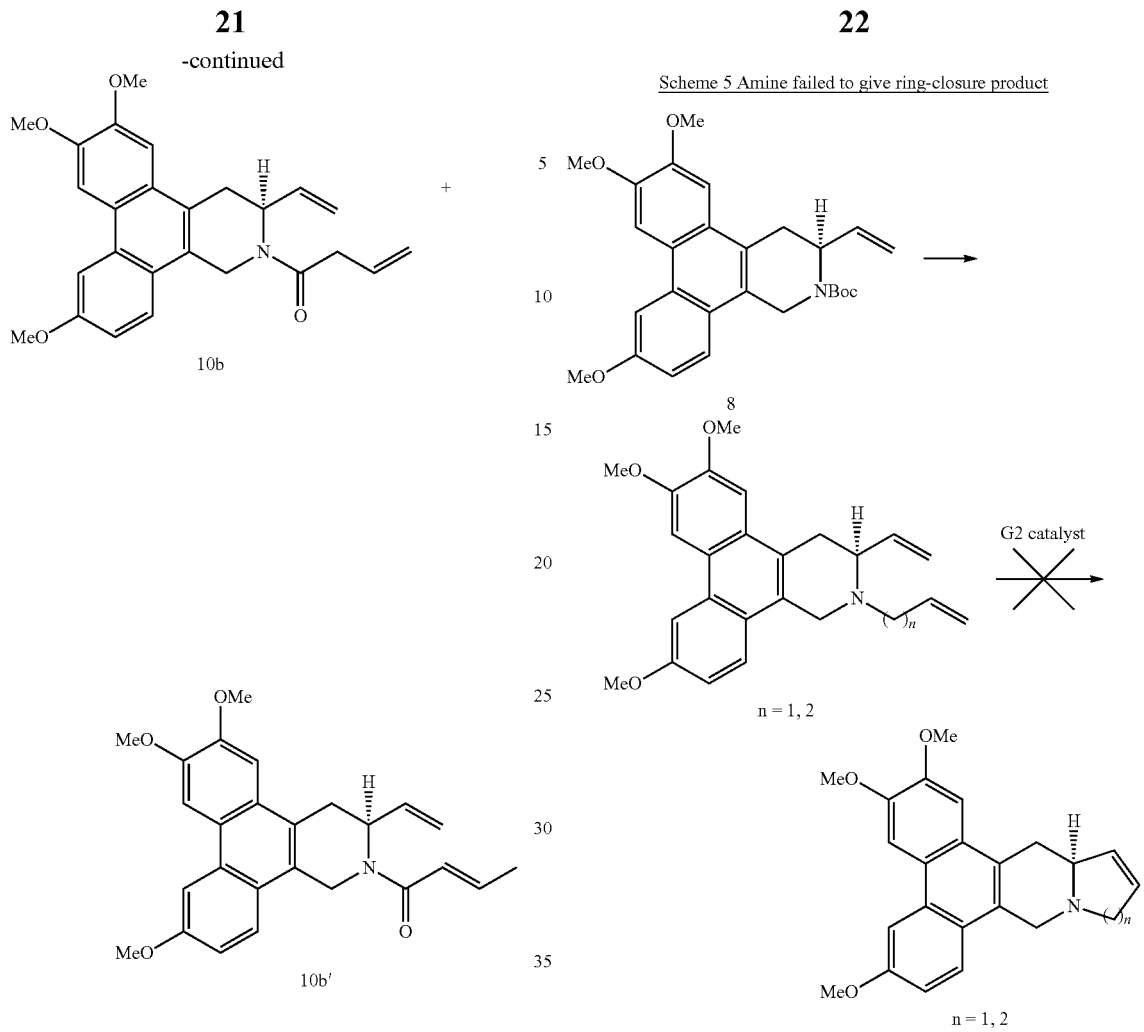

The ring closure reaction was carried out using Grubb's $2^{nd}$ generation (G2) catalyst (Scheme 4) in $CH_2Cl_2$ with reflux. The duration of the reaction ranged from two hours (6-membered) to longer, depending on the size of the ring system being constructed. Treatment of 10b' with G2 catalyst afforded the 5-membered analogs 11a. Initially, we planned to use tertiary amine (Scheme 5) rather than tertiary amide (Scheme 3) intermediates; however, reaction with G2 or other catalysts did not give the expected ring-closure products (Scheme 5). This failure is probably due to the competitive coordination of the N atom to the ruthenium center, which resulted in catalyst poisoning. Several preventive procedures were therefore investigated, for example, using p-toluenesulfonic acid to form a salt with the amine or using $Ti(OiPr)_4$ to chelate with the N atom.[16,17] However, none of these efforts succeeded. The ultimate successful formation of 11 is significant because it opens an avenue not only to analogs with variously sized E-rings but also to more analogs with E-ring substituted with different functional group by using conventional chemical transformation such as oxidation or alkylation. The newly-formed cycloalkene analogs (11a-c) underwent hydrogenation with $H_2$/Pd/C (50 psi) in MeOH to afford 12a-c in high yields. The desired target alkaloids were obtained by reduction of amide to amine in an average yield of 70% to give R-antofine (13a) and R-cryptopleurine (13b), as well as an E-ring expanded analog (13c). The melting points, optical rotations, and NMR spectra of our synthesized 13a and 13b agreed with the data reported in the literature.[7]

New compound 13c was screened in vitro against a panel of human tumor cell lines including A549 (lung), KB (nasopharyngeal), DU-145 (prostate), and HCT-8 (colon), using antofine and cryptopleurine as comparison. The results ($GI_{50}$) are listed in Table 1. Interestingly, compound 13c showed significant cytotoxic activity and was as potent as antofine against A549 and HCT-8 cell growth but with improved selectivity relative to KB and DU145 tumor cell lines. This result suggests that the E-ring size may affect the interaction of the drug molecule and binding site on the target receptor, and the expansion of the E-ring may play a role in the anticancer selectivity. By applying our versatile synthetic methodologies, additional promising analogs will be prepared, including the introduction of polar groups that might lead to enhanced antitumor activity and selectivity, especially to reduce CNS toxicity.

TABLE 1

Anticancer activities of R-antofine and compound 13c

| Compound | A549 $GI_{50}$ (nM) | DU145 $GI_{50}$ (nM) | KB $GI_{50}$ (nM) | HCT-8 $GI_{50}$ (nM) |
|---|---|---|---|---|
| R-antofine | 22 | 25 | 36 | ND |
| R-cryptopleurine | 1.38 | 1.59 | 1.51 | 1.09 |
| 13c | 25 | 179 | 102 | 10 |

In conclusion, we have developed a new efficient, facile, and versatile synthetic route to antofine and cryptopleurine as well as an E-ring expanded analog 13c. A seven-membered E-ring analog was synthesized and reported for the first time. The synthetic 7-membered analog 13c demonstrated comparable cytotoxic potency to the natural product antofine, but with better selectivity than antofine to lung and colon tumor cell lines. Compared with previously reported approaches, our synthetic route has the following advantages. All reactions are performed in high yields and under relatively mild conditions without using expensive enantioselective catalysts or chiral auxiliary agents. In addition and most importantly, our methods have great potential for derivatization on the E ring. Further efforts to create additional analogs of antofine and cryptopleurine through E-ring modification are currently underway. We hope that potent and selective analogs of antofine and cryptopleurine with reduced CNS toxicity will be discovered throughout studies.

Experimental Section

N-(2,3,6-Trimethoxyphenanthren-9-ylmethyl)-D-serine methyl ester (2)

Compound 1 (15.56 g, 47.73 mmol) was suspended in 400 mL of THF, to which LiAlH$_4$ (2.729 g, 71.60 mmol) was added carefully at rt. After 2 h, water and 1N NaOH were added to quench the reaction, which was then filtered. Removal of the solvent in vacuo gave a white solid, which was then dissolved in CHCl$_3$, washed with water and brine, and dried over MgSO$_4$. After removing solvent, the crude product was used in the next step without further purification.

The white solid was suspended in Et$_3$N (18 mL) and CH$_2$Cl$_2$ (400 mL) at 0° C., and then Py.SO$_3$ (22.90 g, 143.19 mmol) in 80 mL of DMSO was added dropwise. The reaction was monitored by TLC before 150 mL of HCl (1N) was added. The organic layer was then washed with sat. NaHCO$_3$, brine, and dried over MgSO$_4$.

After evaporation of the solvent, the resulting yellow oil was dissolved in CH$_2$Cl$_2$ (100 mL) and MeOH (300 mL) at 0° C., to which D-serine hydrochloride (6.22 g, 40 mmol) and Et$_3$N (5.70 mL, 41 mmol) were added. The reaction was stirred at 0° C. for 30 min before HOAc (4.42 mL, 77.60 mmol) and NaBH$_3$CN (5.133 g, 77.60 mmol) were added. The reaction mixture was then warmed to rt and stirred overnight. Sat. NaHCO$_3$ was added to quench the reaction, and the mixture extracted with CH$_2$Cl$_2$. The organic layers were collected, washed with brine, dried over Na$_2$SO$_4$. Column chromatography eluting with CH$_2$Cl$_2$/MeOH gave 2 (11.38 g 59.7% for three steps) as a light yellow solid: mp 97-99° C.; $[\alpha]^{23}_D$=15.1 (c 2.56, CHCl$_3$); $^1$H NMR (300 MHz, CDCl$_3$): δ 8.12 (d, J=9.0 Hz, 1H), 7.88 (d, J=2.4 Hz, 1H), 7.84 (s, 1H), 7.47 (s, 1H), 7.24 (dd, J=9.0 Hz, J=2.4 Hz, 1H), 7.18 (s, 1H), 4.33 (d, J=12.9 Hz, 1H), 4.13 (d, J=13.2 Hz, 1H), 4.09 (s, 3H), 4.02 (s, 3H), 4.01 (s, 3H), 3.78 (m, 1H), 3.75 (s, 3H); 3.58 (m, 2H); $^{13}$C NMR (75 MHz, CDCl$_3$): δ 173.7, 158.2, 149.8, 149.3, 131.9, 131.5, 127.3, 126.2, 124.9, 124.4 (2×C), 115.4, 108.5, 104.9, 103.6, 62.8, 62.4, 56.3, 56.1, 55.7, 52.4, 50.8; ESI-HRMS ([M+H]$^+$) calcd for C$_{22}$H$_{26}$NO$_6$ 400.1760. found 400.1764.

(R)-Methyl-N-(2,3,6-trimethoxyphenanthren-9-ylmethyl)-oxazolidinone-4-carboxylate (3)

The ester 2 (6.30 g, 15.77 mmol) was dissolved in 200 mL of CH$_2$Cl$_2$ at room temperature, to which 1,1'-carbonyldiimidazole (5.11 g, 31.54 mmol) was added. The mixture was stirred at reflux overnight. Column chromatography eluting with CH$_2$Cl$_2$/MeOH gave 3 (5.10 g, 76%) as a light yellow solid: mp 83-85° C.; $[\alpha]^{23}_D$=11.5 (c 1.36, CHCl$_3$); $^1$H NMR (300 MHz, CDCl$_3$): δ 7.99 (d, J=9.0 Hz, 1H), 7.83 (d, J=2.4 Hz, 1H), 7.78 (s, 1H), 7.33 (s, 1H), 7.21 (dd, J=9.0 Hz, J=2.4 Hz, 1H), 7.13 (s, 1H), 5.28 (d, J=14.7 Hz, 1H), 4.61 (d, J=14.7 Hz, 1H), 4.28-4.27 (m, 2H), 4.07 (s, 3H), 4.01 (s, 3H), 3.98 (s, 3H), 3.95 (dd, J=8.7 Hz, J=5.4 Hz, 1H), 3.64 (s, 3H); $^{13}$C NMR (75 MHz, CDCl$_3$): δ 170.4, 158.5, 157.4, 149.9, 149.8, 132.0, 127.2, 126.8, 126.3, 126.2, 124.9, 124.3, 115.7, 108.5, 105.2, 103.6, 64.8, 56.3, 56.1 (2×C), 55.7, 52.9, 46.3; ESI-HRMS ([M+H]$^+$) calcd for C$_{23}$H$_{24}$NO$_7$ 426.1553. found 426.1566.

(R)—N-(2,3,6-Trimethoxyphenanthren-9-ylmethyl)-oxazolidinone-4-carboxylic acid (4)

The oxazolidinone (5.10 g, 12.00 mmol) was dissolved in 1,4-dioxane (100 mL), to which aq. KOH (2N, 50 mL) was added. The mixture was stirred at rt for 1.5 h, and then cooled to 0° C. The pH was adjusted to 3 with 85% H$_3$PO$_4$. The resulting solid was collected and washed sequentially with cold water, cold MeOH, and diethyl ether. After being dried under vacuum, 4.10 g of white solid were obtained. Yield: 83%; mp 248-250° C.; $[\alpha]^{23}_D$=-4.8 (c 0.23, MeOH); $^1$H NMR (300 MHz, DMSO-d$_6$): δ 8.14 (d, J=2.4 Hz, 1H), 8.07 (s, 1H), 7.97 (d, J=9.3 Hz, 1H), 7.49 (s, 1H), 7.43 (s, 1H), 7.27 (dd, J=9.0 Hz, J=2.4 Hz, 1H), 5.19 (d, J=15.3 Hz, 1H), 4.52 (d, J=15.6 Hz, 1H), 4.44 (t, J=9.3 Hz, 1H), 4.31 (dd, J=9.0 Hz, J=3.3 Hz, 1H), 4.04 (m, 1H), 4.03 (s, 3H), 4.00 (s, 3H), 3.92 (s, 3H); $^{13}$C NMR (75 MHz, DMSO-d$_6$): δ 171.3, 157.9, 157.2, 149.5, 149.3, 131.6, 127.1, 126.4, 125.3, 124.5, 124.1, 123.6, 115.8, 108.7, 105.1, 104.2, 64.8, 55.9, 55.8, 55.5 (2×C), 45.0; ESI-HRMS ([M–H]$^-$) calcd for C$_{22}$H$_{20}$NO$_7$ 410.1240. found 410.1255.

(R)-11,14-Dioxo-12-oxa-antofine (5)

The acid (5.06 g, 12.31 mmol) was suspended in CH$_2$Cl$_2$ (200 mL) and DMF (1 mL), to which (COCl)$_2$ (3.75 mL, 43.09 mmol) was added. The mixture was stirred for 1 h, and then SnCl$_4$ (5.76 mL, 49.24 mmol) was added dropwise. The mixture was then warmed to 50° C. and stirred overnight. The reactions was quenched with HCl (2N). After normal workup, column chromatography eluting with CH$_2$Cl$_2$/MeOH gave 5 (4.60 g, 95%) as a light yellow solid: mp 244° C. (dec.); $[\alpha]^{23}_D$=-204.4 (c 0.59, CHCl$_3$); $^1$H NMR (300 MHz, CDCl$_3$): δ 9.07 (s, 1H), 7.95 (d, J=9.3 Hz, 1H), 7.81 (d, J=2.7 Hz, 1H), 7.79 (s, 1H), 7.26 (dd, J=9.3 Hz, J=2.7 Hz, 1H), 5.59 (d, J=18.0 Hz, 1H), 4.93 (dd, J=13.2 Hz, J=9.0 Hz, 1H), 4.92 (d, J=17.7 Hz, 1H), 4.68 (t, J=9.0 Hz, 1H), 4.51 (ddd, J=9.0 Hz, J=4.2 Hz, J=1.5 Hz, 1H), 4.11 (s, 3H), 4.09 (s, 3H), 4.06 (s, 3H); $^{13}$C NMR (75 MHz, CDCl$_3$): δ 193.5, 161.4, 157.4, 150.8, 149.4, 139.0, 134.8, 127.0 (2×C), 124.7, 124.3, 121.3, 116.6, 108.1, 104.9, 103.3, 64.9, 58.3, 56.1, 56.0, 55.8, 42.3; ESI-HRMS ([M+H]$^+$) calcd for C$_{22}$H$_{20}$NO$_6$ 394.1291. found 394.1296.

(R)-11-Oxo-12-oxa-antofine (6)

The ketone (4.60 g, 11.70 mmol) was suspended in MeOH, to which NaBH$_4$ (888 mg, 23.40 mmol) was added at rt The mixture was stirred for 1 h before sat. NaHCO$_3$ was added. Most solvent was removed by evaporation and the solid was collected by filtration, washed with cold MeOH and diethyl ether. The white solid was then dissolved in TFA (200 mL) and Et$_3$SiH (3.75 mL, 23.40 mmol) and refluxed for 1 h. TFA was removed under reduced pressure. Column chromatography eluting with CH$_2$Cl$_2$/MeOH furnished 6 (4.21 g, 95%) as a white solid: mp 253-255° C.; $[\alpha]^{23}_D = -177.5$ (c 0.44, CHCl$_3$); $^1$H NMR (300 MHz, CDCl$_3$): δ 7.90 (s, 1H), 7.89 (d, J=3.0 Hz, 1H), 7.78 (d, J=9.0 Hz, 1H), 7.24 (dd, J=9.6 Hz, J=3.0 Hz, 1H), 7.22 (s, 1H), 5.18 (d, J=16.5 Hz, 1H), 4.73 (t, J=8.1 Hz, 1H), 4.71 (d, J=16.5 Hz, 1H), 4.34 (dd, J=8.7 Hz, J=5.1 Hz, 1H), 4.17-4.09 (m, 1H), 4.11 (s, 3H), 4.06 (s, 3H), 4.03 (s, 3H), 3.41 (dd, J=15.9 Hz, J=4.2 Hz, 1H), 2.97 (dd, J=15.6 Hz, J=10.8 Hz, 1H); $^{13}$C NMR (75 MHz, CDCl$_3$ and CD$_3$OD): δ 158.3, 157.7, 149.8, 149.0, 130.6, 126.2, 124.2, 124.1, 123.6, 123.1, 122.6, 115.5, 105.0, 104.2, 103.9, 69.2, 56.2, 56.1, 55.7, 50.9, 41.8, 30.8; ESI-HRMS ([M+H]$^+$) calcd for C$_{22}$H$_{22}$NO$_5$ 380.1498. found 380.1478.

(R)-(6,7,10-Trimethoxy-1,2,3,4-tetrahydrodibenzo[f,h]isoquinolin-3-yl)methanol (7)

11-Oxo-12-oxa-antofine (4.21 g, 11.10 mmol) was suspended in 100 mL of MeOH and 50 mL of NaOH (6N), and the mixture was stirred at 100° C. overnight. Most solvent was removed by evaporation and the residue was suspended in 200 mL of cold water. The solid was filtered, washed sequentially with cold MeOH and diethyl ether, and dried under vacuum to give 3.61 g of white solid. Yield: 92%; mp 243-245° C.; $[\alpha]^{23}_D = 100$ (c 0.71, CHCl$_3$); $^1$H NMR (300 MHz, DMSO-d$_6$): δ 8.08 (s, 1H), 8.07 (d, J=2.7 Hz, 1H), 7.80 (d, J=9.0 Hz, 1H), 7.31 (s, 1H), 7.21 (dd, J=9.0 Hz, J=2.4 Hz, 1H), 4.79 (t, 8.5 Hz, 1H), 4.42 (d, J=16.2 Hz, 1H), 4.18 (d, J=16.2 Hz, 1H), 4.02 (s, 3H), 3.98 (s, 3H), 3.94 (s, 3H), 3.68-3.63 (m, 1H), 3.56-3.51 (m, 1H), 3.01-2.97 (m, 2H), 2.67-2.58 (m, 1H); $^{13}$C NMR (75 MHz, DMSO-d$_6$): δ 157.6, 149.6, 148.6, 129.9, 127.8, 127.0, 125.5, 124.4, 123.8, 123.2, 115.7, 105.0 (2×C), 104.2, 65.7, 56.2, 55.8, 55.7, 55.2, 46.1, 29.2; ESI-HRMS ([M+H]$^+$) calcd for C$_{21}$H$_{24}$NO$_4$ 354.1705. found 354.1702.

(R)—N-Boc-(6,7,10-trimethoxy-1,2,3,4-tetrahydrodibenzo[f,h]isoquinolin-3-yl)methanol (8)

(Boc)$_2$O (3.14 g, 14.40 mmol) was added to the amino-alcohol (4.240 g, 12 mmol) in 100 mL of CH$_2$Cl$_2$ and Et$_3$N (6 mL), and the mixture was stirred for 2 h. HCl (50 mL, 1N) was added and the organic layer was separated, washed with sat. NaHCO$_3$ and brine, and dried over MgSO$_4$. Column chromatography eluting with CH$_2$Cl$_2$/MeOH gave 5.20 g of compound 8 as a white solid. Yield: 95.6%; mp 105-107° C.; $[\alpha]^{23}_D = 85.5$ (c 0.42, CHCl$_3$); $^1$H NMR (300 MHz, CDCl$_3$): δ 7.89 (s, 2H), 7.81 (d, J=9.0 Hz, 1H), 7.28 (s, 1H), 7.22 (d, J=8.7 Hz, 1H), 5.29 (br s, 1H), 4.84 (m, 1H), 4.61 (br s, 1H), 4.09 (s, 3H), 4.05 (s, 3H), 4.01 (s, 3H), 3.73-3.62 (m, 2H), 3.27 (dd, J=16.5 Hz, J=6.3 Hz, 1H), 3.18 (t, J=16.5 Hz, 1H), 1.55 (s, 9H); $^{13}$C NMR (75 MHz, CDCl$_3$): δ 157.9, 156.2, 149.7, 148.8, 130.4, 126.7, 124.0, 123.9, 123.8, 123.4, 122.8, 115.2, 105.1, 104.2, 104.0, 80.6, 62.7, 56.2, 56.0, 55.7, 50.6, 41.0, 28.6 (3×C), 26.5; ESI-HRMS ([M+H]$^+$) calcd for C$_{26}$H$_{32}$NO$_6$ 454.2230. found 454.2246.

(S)-tert-Butyl-6,7,10-trimethoxy-3-vinyl-3,4-dihydrodibenzo[f,h]isoquinoline-2(1H)-carboxylate (9)

To a solution of Ph$_3$P═CH$_2$Br (1.43 g, 4 mmol) in THF was added n-BuLi (2M in heptanes, 1.95 mL) at 0° C. under N$_2$. The mixture was stirred for 0.5 h before compound 8 (906 mg, 2 mmol) in THF (20 mL) was added dropwise. The mixture was then stirred for 2 h (monitored by TLC). Sat. NH$_4$Cl was added to quench the reaction and THF was removed by evaporation. The residue was dissolved in CH$_2$Cl$_2$ (50 mL), washed with sat. NaHCO$_3$ and brine, and dried over MgSO$_4$. Column chromatography eluting with EtOAc/Hexane gave 9 (684 mg, 76%) as a light yellow foam: mp 177-179° C.; $[\alpha]^{23}_D = 118.2$ (c 0.56, CHCl$_3$); $^1$H NMR (300 MHz, CDCl$_3$): δ 7.92 (s, 1H), 7.91 (d, J=2.4 Hz, 1H), 7.85 (d, J=9.0 Hz, 1H), 7.31 (s, 1H), 7.23 (dd, J=9.0 Hz, J=2.7 Hz, 1H), 5.86-5.75 (m, 1H), 5.29 (m, 1H), 5.26 (d, J=16.8 Hz, 1H), 5.16-5.04 (m, 2H), 4.59 (d, J=17.4 Hz, 1H), 4.11 (s, 3H), 4.06 (s, 3H), 4.01 (s, 3H), 3.36 (dd, J=16.2 Hz, J=6.0 Hz, 1H), 3.29 (t, J=16.5 Hz, 1H), 1.55 (s, 9H); $^{13}$C NMR (75 MHz, CDCl$_3$): δ 157.9, 155.3, 149.8, 148.8, 136.5, 130.4, 126.8, 124.4, 124.2, 123.9, 123.6, 123.1, 116.6, 115.2, 105.1, 104.3, 104.1, 80.3, 77.4, 56.3, 56.1, 55.7, 41.1, 29.8, 28.7 (3×C); ESI-HRMS ([M+Na]$^+$) calcd for C$_{27}$H$_{31}$NO$_5$Na 472.2100. found 472.2103.

General Procedures for the Synthesis of 10a-c:

Compound 9 (225 mg, 0.50 mmol) was dissolved in TFA/CH$_2$Cl$_2$ (10 mL) at rt, and the mixture was stirred for 1 h. The solvent was removed by evaporation and TFA was neutralized with NMM. The residue was redissolved in DMF (10 mL), to which the appropriate unsaturated acid (0.70 mmol), EDC hydrochloride (134 mg, 0.70 mmol), HOBt (95 mg, 0.70 mmol), NMM (0.35 mL) were added. Stirring was continued overnight. DMF was then removed under reduced pressure, and the residue was dissolved in CH$_2$Cl$_2$ (30 mL), washed with HCl (1N), sat. NaHCO$_3$, and brine, and dried over MgSO$_4$. Compounds 10a and 10c were isolated by column chromatography eluting with MeOH/CH$_2$Cl$_2$. For 10b, the unsaturated acid (1.50 mmol) was added to a mixture of amine (0.50 mmol), DEPC (0.25 mL, 1.50 mmol), and Et$_3$N (0.42 mL, 3.00 mmol) in DMF, which was stirred overnight at room temperature. Standard workup and chromatography with EtOAc/Hexane gave 10b in 76% yield.

10a:

mp 104-106° C.; $[\alpha]^{23}_D = 136$ (c 0.58, CHCl$_3$); $^1$H NMR (300 MHz, CDCl$_3$, compound rotameric at rt): δ 7.86 (m, 3H), 7.26 (s, 1H), 7.21 (dd, J=9.3 Hz, J=2.4 Hz, 1H), 6.77 (brs, 1H), 6.40 (d, J=16.8 Hz, 1H), 5.93-5.57 (m, 3H), 5.24-5.01 (m, 3H), 4.83-4.59 (d, J=17.1 Hz, 1H), 4.09 (s, 3H), 4.05 (s, 3H), 4.02 (s, 3H), 3.33 (s, 2H); $^{13}$C NMR (75 MHz, CDCl$_3$): δ 166.7, 166.1, 157.9, 149.6, 148.7, 136.0, 130.4, 128.3, 126.3, 123.8, 123.2, 122.0, 117.4, 115.1, 105.1, 104.9, 104.1, 103.8, 57.0, 56.2, 56.0, 55.9, 55.7, 55.5, 52.9, 48.1, 42.7, 40.1, 30.6, 29.8, 28.9; ESI-HRMS ([M+H]$^+$) calcd for C$_{25}$H$_{26}$NO$_4$ 404.1862. found 404.1854.

10b:

mp 170-172° C.; $[\alpha]^{23}_D = 125.1$ (c 0.64, CHCl$_3$); $^1$H NMR (300 MHz, CDCl$_3$, compound rotameric at rt): δ 7.95-7.73 (m, 3H), 7.32-7.23 (m, 2H), 6.09-6.03 (m, 1H), 5.89-5.77 (m, 3H), 5.27-5.01 (m, 4H), 4.85-4.53 (d, J=17.4 Hz, 1H), 4.11 (s, 3H), 4.07 (s, 3H), 4.03 (s, 3H), 3.40-3.31 (m, 4H); $^{13}$C NMR (75 MHz, CDCl$_3$): δ 170.5, 170.2, 158.0, 149.8, 148.8, 135.9, 135.6, 131.7, 131.4, 130.5, 126.4, 124.6, 124.2, 123.9, 123.4, 122.1, 118.2, 117.3, 115.4, 115.1, 105.2, 104.3, 103.9, 56.2, 56.1, 55.7, 53.1, 47.9, 42.7, 39.9, 39.8, 39.4, 30.7, 29.0; ESI-HRMS ([M+H]$^+$) calcd for C$_{26}$H$_{28}$NO$_4$ 418.2018. found 418.2024.

10c:

mp 73-75° C.; $[\alpha]^{23}_D = 144.6$ (c 0.35, CHCl$_3$); $^1$H NMR (300 MHz, CDCl$_3$, compound rotameric at rt): δ 7.94-7.75 (m, 3H), 7.31-7.22 (m, 2H), 5.98-5.76 (m, 3H), 5.19-4.99 (m, 5H), 4.84-4.53 (d, J=17.1 Hz, 1H), 4.10 (s, 3H), 4.06 (s, 3H), 4.00 (s, 3H), 3.33 (d, J=18.6 Hz, 2H), 2.65 (q, J=7.2 Hz, 2H), 2.55-2.46 (m, 2H); $^{13}$C NMR (75 MHz, CDCl$_3$): δ 171.8, 171.5, 158.0, 149.7, 148.8, 137.6, 136.1, 135.8, 130.5, 126.7, 126.4, 124.5, 124.4, 124.0, 123.9, 123.5, 123.1, 122.0, 117.3, 117.1, 115.5, 115.1, 105.2, 104.3, 103.9, 56.2, 56.1, 55.7, 52.9, 47.8, 42.5, 39.9, 33.6, 33.0, 30.8, 29.5, 29.0; ESI-HRMS ([M+H]$^+$) calcd for $C_{27}H_{30}NO_4$ 432.2175. found 432.2184.

General Procedures for the Synthesis of 11a-c:

Compounds 10a-c were dissolved in degassed $CH_2Cl_2$ under $N_2$, to which Grubb's $2^{nd}$ generation catalyst in $CH_2Cl_2$ was added in one portion. The reaction was stirred at reflux for 2 h or monitored by TLC. Compounds 11a-c were isolated by column chromatography eluting with $CH_2Cl_2$/MeOH. Yield: 70%-85%.

11a:

mp 105-107° C.; $[\alpha]^{23}_D$=−191.8 (c 0.55, CHCl$_3$); $^1$H NMR (300 MHz, CDCl$_3$): δ 7.90 (s, 1H), 7.89 (d, J=3.3 Hz, 1H), 7.87 (d, J=9.0 Hz, 1H), 7.42 (d, J=5.7 Hz, 1H), 7.25 (s, 1H), 7.24 (dd, J=9.0 Hz, J=2.7 Hz, 1H), 6.39 (d, J=6.0 Hz, 1H), 5.49 (d, J=17.1 Hz, 1H), 4.75 (d, J=17.7 Hz, 1H), 4.35 (dd, J=12 Hz, J=5.4 Hz, 1H), 4.11 (s, 3H), 4.06 (s, 3H), 4.02 (s, 3H), 3.62 (dd, J=15.9 Hz, J=4.5 Hz, 1H), 2.71 (dd, J=15.0 Hz, 12.0 Hz, 1H); $^{13}$C NMR (75 MHz, CDCl$_3$): δ 169.5, 158.2, 149.8, 149.0, 147.4, 130.6, 128.6, 126.2, 124.4, 124.1, 123.9, 123.4, 122.4, 115.4, 105.2, 104.2, 104.0, 57.7, 56.2, 56.1, 55.7, 40.2, 30.0; ESI-HRMS ([M+H]$^+$) calcd for $C_{23}H_{22}NO_4$ 376.1549. found 376.1559.

11b:

mp 238-240° C.; $[\alpha]^{23}_D$=−216.4 (c 0.58, CHCl$_3$); $^1$H NMR (300 MHz, CDCl$_3$): δ 7.93 (d, J=9.3 Hz, 1H), 7.90-7.89 (m, 2H), 7.23-7.21 (m, 2H), 6.07 (d, J=17.7 Hz, 1H), 6.03-5.90 (m, 2H), 4.49 (d, J=17.4 Hz, 1H), 4.40-4.36 (m, 1H), 4.11 (s, 3H), 4.05 (s, 3H), 4.02 (s, 3H), 3.35 (dd, J=15.6 Hz, J=2.4 Hz, 1H), 3.13 (brs, 2H), 3.04-2.99 (m, 1H); $^{13}$C NMR (75 MHz, CDCl$_3$): δ 166.4, 158.1, 149.7, 148.8, 130.5, 126.2, 125.1, 124.7, 124.6, 123.9, 123.8, 123.5, 122.2, 115.2, 105.1, 104.1, 103.9, 56.2, 56.1, 55.7, 54.6, 42.8, 34.8, 32.1; ESI-HRMS ([M+H]$^+$) calcd for $C_{24}H_{24}NO_4$ 390.1705. found 390.1706.

11c:

mp 205-207° C.; $[\alpha]^{23}_D$=−81.9 (c 1.50, CHCl$_3$); $^1$H NMR (300 MHz, CDCl$_3$): δ 8.08 (d, J=9.0 Hz, 1H), 7.93 (s, 1H), 7.90 (d, J=2.7 Hz, 1H), 7.36 (s, 1H), 7.25 (dd, J=9.0 Hz, J=2.4 Hz, 1H), 5.75-5.70 (m, 1H), 5.59-5.54 (m, 1H), 5.32 (d, J=15.9 Hz, 1H), 4.97 (d, J=16.2 Hz, 1H), 4.89 (m, 1H), 4.11 (s, 3H), 4.08 (s, 3H), 4.01 (s, 3H), 3.37 (dd, J=15.3 Hz, J=5.4 Hz, 1H), 3.25 (dd, J=15.3 Hz, J=8.1 Hz, 1H), 3.10 (dt, J=13.2 Hz, J=8.1 Hz, 1H), 2.56 (dt, J=13.5 Hz, 4.8 Hz, 1H), 2.42 (m, 2H); $^{13}$C NMR (75 MHz, CDCl$_3$): δ 173.8, 158.0, 149.9, 148.9, 131.6, 130.6, 130.5, 128.2, 125.8, 125.7, 125.0, 124.0, 123.2, 115.4, 105.1, 104.3, 103.7, 56.2, 56.1, 55.7, 51.6, 40.9, 35.1, 31.7, 25.2; ESI-HRMS ([M+H]$^+$) calcd for $C_{25}H_{26}NO_4$ 404.1862. found 404.1856.

General Procedure for the Synthesis of 12a-c:

Compounds 11a-d were dissolved in MeOH, to which Pd/C was added. The mixture was hydrogenated under $H_2$ at 50 psi overnight. The catalyst was removed by filtration and column chromatography eluting with $CH_2Cl_2$/MeOH gave 12a-c. Yield: 90%.

12a:

mp 185-187° C.; $[\alpha]^{23}_D$=−134.4 (c 0.45, CHCl$_3$); $^1$H NMR (300 MHz, CDCl$_3$): δ 7.84 (s, 1H), 7.83 (d, J=3.0 Hz, 1H), 7.79 (d, J=9.0 Hz, 1H), 7.20 (dd, J=9.0 Hz, J=2.7 Hz, 1H), 7.19 (s, 1H), 5.29 (d, J=17.4 Hz, 1H), 4.50 (d, J=17.1 Hz, 1H), 4.08 (s, 3H), 4.03 (s, 3H), 4.00 (s, 3H), 3.91-3.84 (m, 1H), 3.36 (dd, J=15.6 Hz, J=4.2 Hz, 1H), 2.73 (dd, J=15.6 Hz, 11.1 Hz, 1H), 2.59-2.44 (m, 3H), 2.05-2.44 (m, 1H); $^{13}$C NMR (75 MHz, CDCl$_3$): δ 174.2, 158.1, 149.7, 148.8, 130.4, 126.4, 124.4, 124.0, 123.9, 123.8, 123.4, 115.2, 105.1, 104.2, 104.0, 56.1, 56.0, 55.7, 53.3, 41.1, 33.5, 30.3, 25.5; ESI-HRMS ([M+H]$^+$) calcd for $C_{23}H_{24}NO_4$ 378.1705. found 378.1713.

12b:

mp 257-259° C.; $[\alpha]^{23}_D$=−183.6 (c 1.9, CHCl$_3$); $^1$H NMR (300 MHz, CDCl$_3$): δ 7.88 (d, J=9.0 Hz, 1H), 7.86 (s, 1H), 7.85 (d, J=3.0 Hz, 1H), 7.21 (dd, J=9.0 Hz, J=2.7 Hz, 1H), 7.16 (s, 1H), 5.88 (d, J=17.4 Hz, 1H), 4.41 (d, J=17.4 Hz, 1H), 4.09 (s, 3H), 4.04 (s, 3H), 4.00 (s, 3H), 3.79-3.74 (m, 1H), 3.11-3.02 (m, 2H), 2.52 (t, J=6.0 Hz, 2H), 2.28-2.20 (m, 1H), 2.05-1.96 (m, 1H), 1.94-1.84 (m, 2H); $^{13}$C NMR (75 MHz, CDCl$_3$): δ 169.7, 157.9, 149.6, 148.7, 130.4, 126.2, 124.7, 124.6, 124.0, 123.7, 123.5, 115.1, 105.1, 104.1, 103.9, 56.2, 56.1, 55.7, 52.7, 43.4, 34.0, 33.1, 29.2, 18.6; ESI-HRMS ([M+H]$^+$) calcd for $C_{24}H_{26}NO_4$ 392.1862. found 392.1865.

12c:

mp 232-234° C.; $[\alpha]^{23}_D$=47.2 (c 0.97, CHCl$_3$); $^1$H NMR (300 MHz, CDCl$_3$): δ 8.12 (d, J=9.0 Hz, 1H), 7.95 (s, 1H), 7.92 (d, J=2.4 Hz, 1H), 7.38 (s, 1H), 7.26 (dd, J=9.0 Hz, J=2.4 Hz, 1H), 5.23 (d, J=15.9 Hz, 1H), 4.97 (d, J=15.9 Hz, 1H), 4.12 (s, 3H), 4.09 (s, 3H), 4.02 (s, 3H), 3.96-3.92 (m, 1H), 3.39 (dd, J=15.0 Hz, J=5.4 Hz, 1H), 3.15 (dd, J=15.3 Hz, 6.9 Hz, 1H), 2.66-2.64 (m, 2H), 1.88-1.84 (m, 3H), 1.65-1.56 (m, 3H); $^{13}$C NMR (75 MHz, CDCl$_3$): δ 175.0, 158.0, 149.9, 148.9, 130.4, 127.4, 126.0, 125.7, 125.1, 124.1, 123.2, 115.4, 105.1, 104.4, 103.8, 56.2, 56.1, 55.7, 54.3, 40.0, 37.0, 34.4, 32.4, 28.2, 23.1; ESI-HRMS ([M+H]$^+$) calcd for $C_{25}H_{28}NO_4$ 406.2018. found 406.2024.

General Procedure for the Synthesis of R-Antofine (13a), R-Cryptopleurine (13b), and Compound 13c:

The amides 12a-c and LiAlH$_4$ (2 equiv.) were suspended in THF (15 mL), which was stirred for 2-3 h. Water was then added to quench the reaction, followed by aq. NaOH (1N, 1 mL) and H$_2$O (1 mL). The mixture was filtered and then extracted with CHCl$_3$ and dried over MgSO$_4$. Column chromatography eluting with $CH_2Cl_2$/MeOH gave the target products. Yield: 70-80%.

R-Antofine (13a):

mp 204-206° C. (lit. 206-211° C.); $[\alpha]^{23}_D$=−129.2 (c 0.48, CHCl$_3$); $^1$H NMR (300 MHz, CDCl$_3$): δ 7.92 (s, 1H), 7.90 (d, J=2.4 Hz, 1H), 7.82 (d, J=9.0 Hz, 1H), 7.32 (s, 1H), 7.20 (dd, J=9.0 Hz, J=2.7 Hz, 1H), 4.69 (d, J=15.9 Hz, 1H), 4.11 (s, 3H), 4.07 (s, 3H), 4.02 (s, 3H), 3.69 (d, J=14.7 Hz, 1H), 3.46 (dt, J=8.7 Hz, J=1.8 Hz, 1H), 3.35 (dd, J=16.2 Hz, J=2.4 Hz, 1H), 2.90 (dd, J=15.6 Hz, J=10.8 Hz, 1H), 2.51-2.41 (m, 2H), 2.26-2.21 (m, 1H), 2.05-1.91 (m, 2H), 1.83-1.74 (m, 1H); $^{13}$C NMR (75 MHz, CDCl$_3$): δ 157.6, 149.6, 148.5, 130.3, 127.3, 126.8, 125.7, 124.4, 124.3, 123.7, 115.0, 104.9, 104.2, 104.1, 60.4, 56.2, 56.0, 55.7, 55.2, 54.0, 33.9, 31.5, 21.8; ESI-HRMS ([M+H]$^+$) calcd for $C_{23}H_{26}NO_3$ 364.1913. found 364.1918.

R-Cryptopleurine (13b):

mp 201-203° C.; $[\alpha]^{23}_D$=−108.8 (c 0.64, CHCl$_3$); $^1$H NMR (300 MHz, CDCl$_3$): δ 7.87 (s, 1H), 7.86 (d, J=3.0 Hz, 1H), 7.76 (d, J=9.0 Hz, 1H), 7.20 (s, 1H), 7.17 (dd, J=9.0 Hz, J=2.7 Hz, 1H), 4.39 (d, J=15.6 Hz, 1H), 4.08 (s, 3H), 4.04 (s, 3H), 3.99 (s, 3H), 3.56 (d, J=15.3 Hz, 1H), 3.24 (d, J=11.1 Hz, 1H), 3.00 (dd, J=16.5 Hz, J=3.0 Hz, 1H), 2.82 (dd, J=15.9 Hz, J=10.5 Hz, 1H), 2.33-2.21 (m, 2H), 2.01-1.97 (m, 1H), 1.89-1.84 (m, 1H), 1.78 (m, 2H), 1.52-1.45 (m, 2H); $^{13}$C NMR (75 MHz, CDCl$_3$): δ 157.5, 149.5, 148.4, 130.2, 126.6, 125.7, 124.6, 124.2, 123.8, 123.5, 114.9, 104.8, 104.0 (2×C), 57.6, 56.4, 56.2, 56.1, 56.0, 55.6, 34.9, 33.9, 26.1, 24.5; ESI-HRMS ([M+H]$^+$) calcd for $C_{24}H_{28}NO_3$ 378.2069. found 378.2077.

13c:

mp 193-195° C.; $[\alpha]^{23}_D$=−82.6 (c 0.38, CHCl$_3$); $^1$H NMR (300 MHz, CDCl$_3$): δ 7.90 (s, 1H), 7.89 (d, J=2.4 Hz, 1H), 7.78 (d, J=9.0 Hz, 1H), 7.27 (s, 1H), 7.19 (dd, J=9.0 Hz, J=2.7 Hz, 1H), 4.42 (d, J=15.0 Hz, 1H), 4.10 (s, 3H), 4.06 (s, 3H), 4.05 (d, J=15.3 Hz, 1H), 4.01 (s, 3H), 3.07-2.93 (m, 4H), 2.82-2.77 (m, 1H), 1.95-1.59 (m, 8H); $^{13}$C NMR (75 MHz, CDCl$_3$): δ 157.5, 149.5, 148.4, 130.2, 127.1, 126.0, 124.3 (2×C), 124.1, 123.6, 115.0, 104.9, 104.2, 104.0, 60.6, 57.3, 56.2, 56.1, 55.7, 55.4, 35.8, 33.9, 29.2, 27.8, 24.7; ESI-HRMS ([M+H]$^+$) calcd for C$_{25}$H$_{30}$NO$_3$ 392.2226. found 392.2225.

References (1) Zeng, W.; Chemler, S. R. *J. Org. Chem.* 2008, 73, 6045-6047.
(2) Gellert, E. *J. Nat. Prod.* 1982, 45, 50-73.
(3) Gao, W.; Chen, A. P.-C.; Leung, C.-H.; Gullen, E. A.; Fuerstner, A.; Shi, Q.; Wei, L.; Lee, K.-H.; Cheng, Y.-C. *Bioorg. Med. Chem. Lett.* 2008, 18, 704-709.
(4) Fuerstner, A.; Kennedy, J. W. *J. Chem.—Eur. J.* 2006, 12, 7398-7410.
(5) Buckley, T. F., III; Henry, R. *J. Org. Chem.* 1983, 48, 4222-32.
(6) Jin, Z.; Li, S. P.; Wang, Q. M.; Huang, R. Q. *Chin. Chem. Lett.* 2004, 15, 1164-1166.
(7) Kim, S.; Lee, T.; Lee, E.; Lee, J.; Fan, G.-j.; Lee Sang, K.; Kim, D. *J Org Chem* 2004, 69, 3144-9.
(8) Suzuki, H.; Aoyagi, S.; Kibayashi, C. *J. Org. Chem.* 1995, 60, 6114-22.
(9) Kim, S.; Lee, J.; Lee, T.; Park, H.-g.; Kim, D. *Org. Lett.* 2003, 5, 2703-2706.
(10) Staerk, D.; Lykkeberg Anne, K.; Christensen, J.; Budnik Bogdan, A.; Abe, F.; Jaroszewski Jerzy, W. *J. Nat. Prod.* 2002, 65, 1299-302.
(11) Gao, W.; Bussom, S.; Grill, S. P.; Gullen, E. A.; Hu, Y.-C.; Huang, X.; Zhong, S.; Kaczmarek, C.; Gutierrez, J.; Francis, S.; Baker, D. C.; Yu, S.; Cheng, Y.-C. *Bioorg. Med. Chem. Lett.* 2007, 17, 4338-4342.
(12) Lesma, G.; Colombo, A.; Landoni, N.; Sacchetti, A.; Silvani, A. *Tetrahedron: Asymmetry* 2007, 18, 1948-1954.
(13) Su, C.-R.; Damu, A. G.; Chiang, P.-C.; Bastow, K. F.; Morris-Natschke, S. L.; Lee, K.-H.; Wu, T.-S. *Bioorg. Med. Chem.* 2008, 16, 6233-6241.
(14) Acherki, H.; Alvarez-Ibarra, C.; Garcia-Navazo, G.; Gomez-Sanchez, E.; Quiroga-Feijoo, M. L. *Tetrahedron: Asymmetry* 2004, 15, 3419-3426.
(15) Lim, S. H.; Ma, S.; Beak, P. *Org. Chem.* 2001, 66, 9056-9062.
(16) Wright, D. L.; Schulte, J. P., II; Page, M. A. *Org. Lett.* 2000, 2, 1847-1850.
(17) Au, C. W. G.; Pyne, S. G. *J. Org. Chem.* 2006, 71, 7097-7099.

EXAMPLE 2

The key intermediate 1 was synthesized and obtained in a gram scale through 12 steps. With a sufficient amount of 1 in hand, a new synthetic route to substituted 12-aza-antofine was designed. The amino group of compound 1 was first protected by the Boc group to give compound 2. Then the hydroxyl group was oxidized to aldehyde using Py.SO$_3$, which was converted to a variety of secondary amines by way of reductive amination using RNH$_2$ and NaBH$_3$CN. Subsequently, the Boc group was removed by TFA, which was reacted with HCHO to give compound 3a-k (Scheme 6).

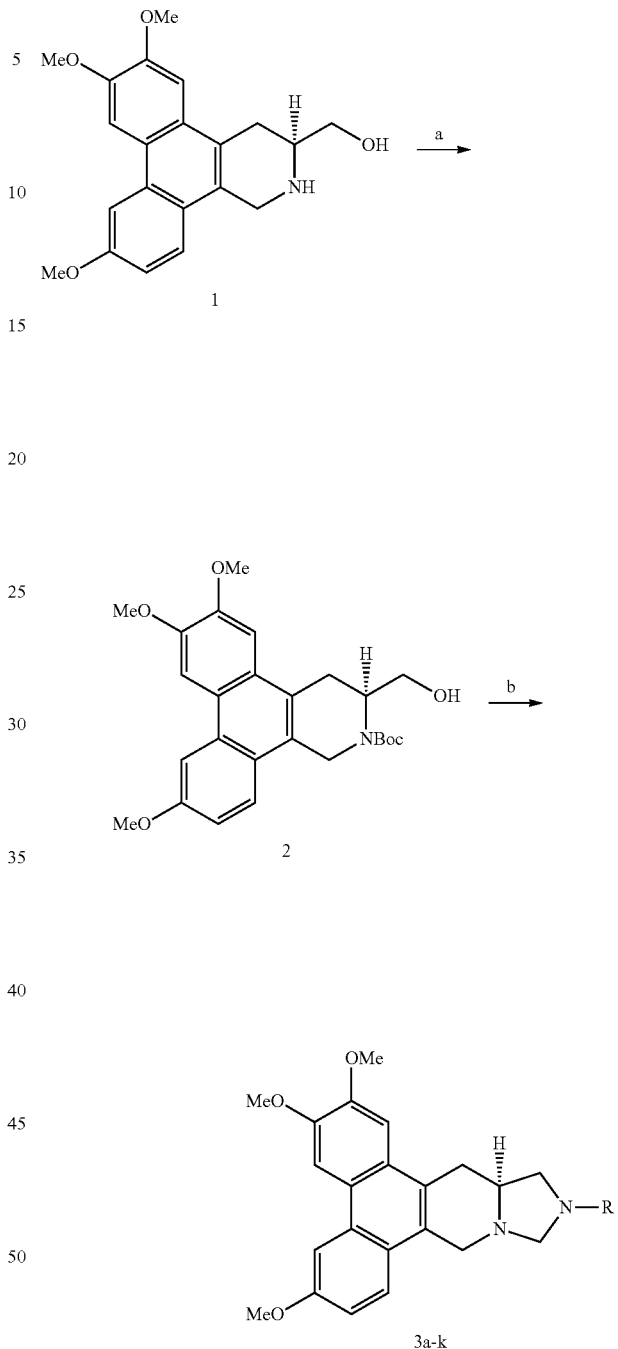

Scheme 6.

Reagents and conditions: (a) (Boc)$_2$O, Et$_3$N, CH$_2$Cl$_2$ (b) i) Py•SO$_3$, DMSO, Et$_3$N, CH$_2$Cl$_2$; ii) RNH$_2$, AcOH, NaBH$_3$CN, MeOH; iii) TFA, CH$_2$Cl$_2$; iv) K$_2$CO$_3$, MgSO$_4$, HCHO, CH$_2$Cl$_2$ The newly synthesized compounds were then screened against a panel of cancer cell lines including A549 (lung), DU-145 (prostate), KB (nasopharyngeal), and HCT-8 (colon). The screening results are shown in Table 2. All compounds showed a substantial decrease of activities compared with R-antofine. In this series, bulky groups such as phenyl or benzyl further reduced the activity (compound 3a/3d/3f). Compound 3h showed the highest activities in a range of 0.66 μM-2.03 μM.

TABLE 2

GI₅₀'s of 12-aza-antofines

| Compound | R | Configuration | A549 (μM) | DU145 (μM) | KB (μM) | HCT-8 (μM) |
|---|---|---|---|---|---|---|
| 3a | –CH₂Ph | S | 5.30 | 4.95 | 5.70 | 3.63 |
| 3b | –CH₂CH(CH₃)₂ | S | 2.00 | 6.60 | 4.40 | 1.82 |
| 3c | –CH₂CH₂CH₂CH₃ | S | 3.94 | 7.38 | 6.64 | 2.71 |
| 3d | –CH₂CH₂Ph | S | 6.62 | 10.20 | 10.03 | 7.47 |
| 3e | –CH₂CH₂CH₂OH | S | 4.41 | 6.36 | 7.83 | 10.77 |
| 3f | –CH(CH₃)Ph | S | >40 | >40 | 36.32 | 20.20 |
| 3g | –CH₂-cyclopropyl | S | 1.80 | 3.70 | 2.71 | 1.85 |
| 3h | –CH(CH₃)₂ | S | 0.66 | 2.03 | 1.72 | 1.00 |
| 3i | –CH₂CH₂NMe₂ | S | 1.67 | 2.26 | 2.31 | 2.01 |
| 3j | –CH₂Ph | R | 2.68 | 4.62 | 3.41 | 1.87 (KBvin) |
| 3k | –CH₂CH₂NMe₂ | R | 4.15 | 6.01 | 2.38 | 10.98 (KBvin) |

In addition, the effect of introducing heteroatoms in the 6-membered E ring was examined and different synthetic strategies were designed to give the 12-aza-cryptopleurine and 13-aza-cryptopleurine. Compound 2 was converted to 4 through oxidation by Py.SO₃ and subquently reductive amination using glycine methyl ester hydrochloride. The cyclization step was accomplished either through TFA/CH₂Cl₂ or indirectly in two steps: deprotection using HCl/MeOH and cyclization using Et₃N/MeOH. Given the fact that compound 5 cannot be readily separated in a large scale by chromatography due to its basic characteristic and high polarity, it was transformed to more easily separatable intermediate 6. The amide was then reduced to amine using BMS/THF to afford compound 7. After deprotection of the Boc group using TFA, a series of 13-aza-cryptopleurines (8a-n) were obtained and screened (Scheme 7).

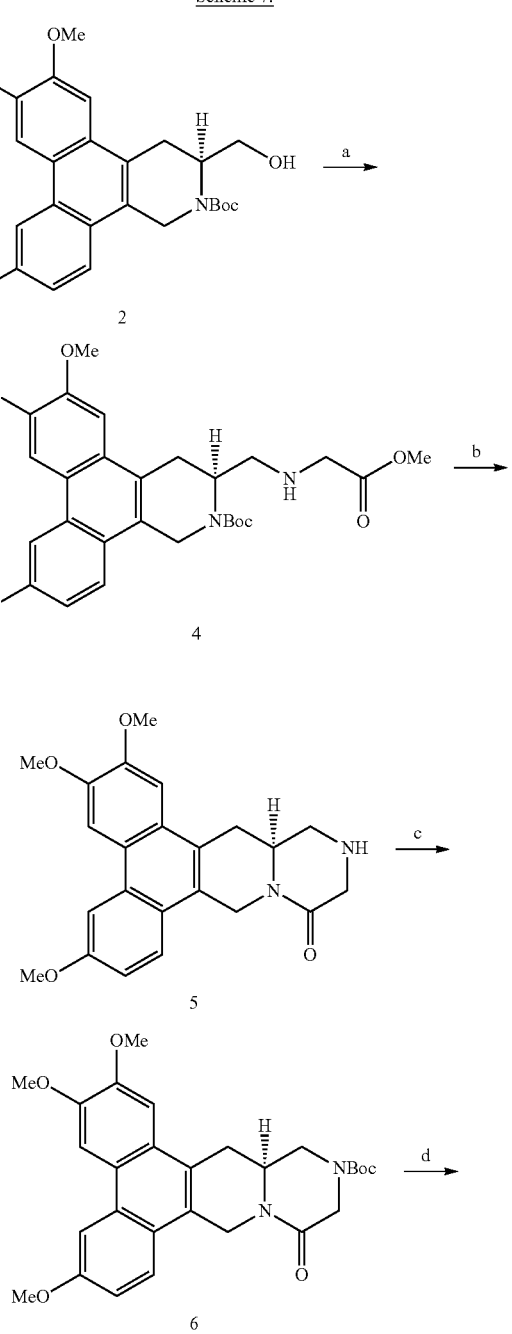

Scheme 7.

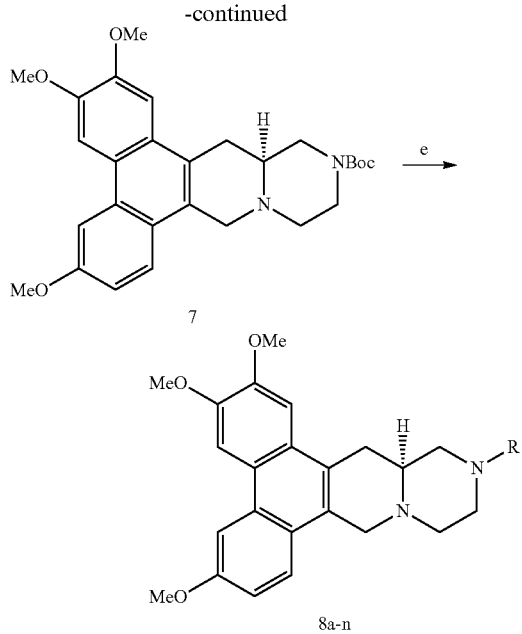

Reagents and conditions: (a) i) Py•SO$_3$, DMSO, Et$_3$N, CH$_2$Cl$_2$; ii) Glycine methyl ester hydrochloride, Et$_3$N, AcOH, NaBH$_3$CN, MeOH (b) i) HCl, MeOH; ii) MeOH, Et$_3$N (c) (Boc)$_2$O, Et$_3$N, CH$_2$Cl$_2$ (d) BMS, THF (e) i) TFA, CH$_2$Cl$_2$; ii) RCOCl, Et$_3$N, CH$_2$Cl$_2$ or RCHO, Et$_3$N, AcOH, NaBH$_3$CN, MeOH The GI$_{50}$'s are listed in Table 3.

TABLE 3

GI$_{50}$'s of 13-aza-cryptopleurines

| Compound | R | Configuration | A549 (μM) | DU145 (μM) | KB (μM) | HCT-8 (μM) |
|---|---|---|---|---|---|---|
| 8a | H, HCl salt | S | 1.73 | 2.08 | 1.79 | 1.62 |
| 8b | (ethyl) | S | 7.13 | 10.48 | 8.24 | 9.45 |
| 8c | (CH$_2$CO$_2$Me) | S | 10.93 | 12.19 | 11.32 | 12.05 |
| 8d | (COCH$_3$) | S | 11.65 | 11.94 | 15.46 | 13.82 |
| 8e | (SO$_2$CH$_3$) | S | 14.52 | 16.97 | 17.52 | 17.83 |
| 8f | (CH$_2$CO$_2$Me) | S | 14.74 | 20.82 | 14.65 | 14.03 |
| 8g | (CH$_2$-cyclopropyl) | S | 0.79 | 2.94 | 6.57 | 0.25 |
| 8h | (cyclopropyl) | S | 23.18 | 17.92 | 23.42 | 13.02 |
| 8i | (COPh) | S | 15.00 | 15.71 | 20.10 | 18.11 |
| 8j | (CH$_2$CH$_2$OH) | S | 14.08 | 12.62 | 8.62 | 7.41 |
| 8k | (PO$_3$(CH$_3$)$_2$) | S | 0.41 | 18.25 | 0.41 | 0.41 |
| 8l | (COCH$_2$N(CH$_3$)$_2$) | R | | | | |
| 8m | (CH$_2$CH(CH$_3$)$_2$) | R | 12.86 | 12.24 | 11.25 | 9.96 (KBvin) |
| 8n | (CH$_2$Ph) | R | 16.43 | 11.87 | 12.14 | 7.64 (KBvin) |

Although all the compounds 8a-n showed a reduced activity compared with cryptopleurine, some interesting results have also been found. Compound 8g exhibited the highest activity against HCT-8 cell line with a GI$_{50}$ of 0.25 μM, and in the meantime, an improved selectivity against A549 and HCT-8 vs. DU145 and KB. Compound 8k was found to have most potent activity against A549, HCT-8 and KB cell lines compared with DU145 cell line.

Considering the versatility of this new synthetic methodology, the effect of heteroatoms incorporated at C-12 position for cryptopleurine was explored (Scheme 8). Compound 2 was first converted to enolether 9 through oxidation to aldehyde followed by Wittig reaction using Ph₃P=CH₂OMe, which was then hydrolyzed to give the one-carbon elongated aldehyde 10 using Hg(OAc)₂ to avoid deprotection of the Boc group. At last, a similar strategy was utilized to synthesize 12-aza-cryptopleurines as that of compound 3a-k. The GI$_{50}$'s are listed in Table 4.

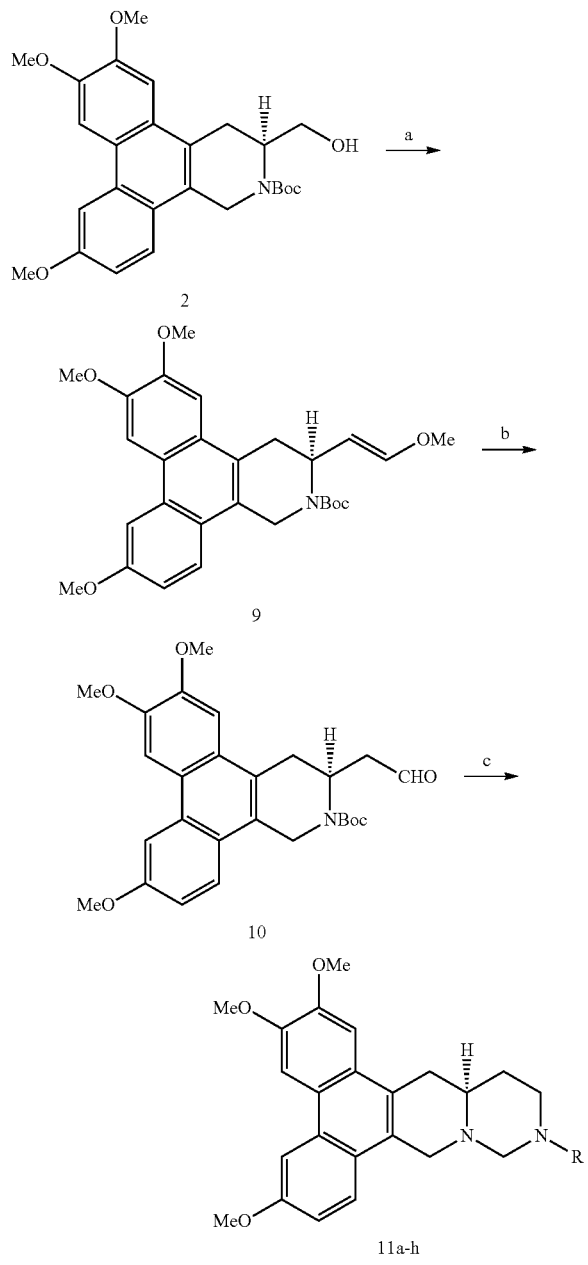

Reagents and conditions: (a) i) Py·SO₃, DMSO, Et₃N, CH₂Cl₂; ii) Ph₃P⁺CH₂OMeCl⁻, THF, KOtBu (b) Hg(OAc)₂, THF, H₂O (c) i) RNH₂, AcOH, NaBH₃CN, MeOH; ii) TFA, CH₂Cl₂; iii) K₂CO₃, MgSO₄, HCHO, CH₂Cl₂

TABLE 4

GI$_{50}$'s of 12-aza-cryptopleurines

| Compound | R | Configuration | A549 (μM) | DU145 (μM) | KB (μM) | HCT-8 (μM) |
|---|---|---|---|---|---|---|
| 11a | ⤳CH₂CH₂OH | S | 5.68 | 1.99 | 1.59 | 10.65 |
| 11b | ⤳CH₂Ph | S | >40 | >40 | >40 | 28.38 |
| 11c | ⤳CH₂CH(CH₃)₂ | S | 1.52 | 2.30 | 5.06 | 1.36 |
| 11d | ⤳CH₂CH₂Ph | S | 29.88 | >40 | >40 | 21.34 |
| 11e | ⤳-cyclopropyl | S | 4.30 | 14.33 | 11.47 | 5.73 |
| 11f | ⤳CH₂NMe₂ | S | 1.78 | 2.97 | 3.08 | 2.37 |
| 11g | ⤳CH₂CH(CH₃)₂ | R | 5.11 | 1.66 | 1.45 | 7.32 (KBvin) |

Compared with modifications at C13 position, a further reduction of activity was observed. Bulky substituents such as phenyl and benzyl group in compound 11b and 11d both had a greatly decreased activity, indicating a relatively smaller binding pocket in the putative target. Compound 11c and 11f showed a similar level of activity in terms of the size of R group.

Besides incorporation of the nitrogen atom, oxygen atom was also examined. Compound 12 was obtained through 3 steps: alkylation with ClCOCH₂Cl, intramolecular substitution aided by NaH, and reduction with BMS (Scheme 9). Its isomer 13 was synthesized by reduction of the aldehyde 10 and subsequent cyclization using HCHO following deprotection of the Boc group (Scheme 10).

Scheme 9.

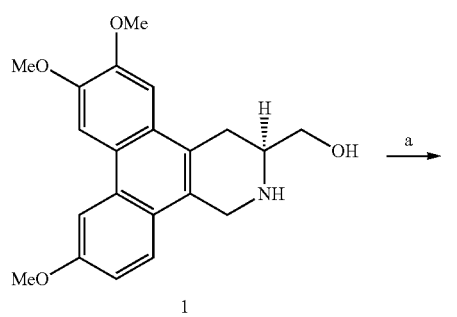

Reagents and conditions: (a) i) ClCH$_2$COCl, Et$_3$N, CH$_2$Cl$_2$; ii) NaH, THF, reflux; iii) BMS, THF

Scheme 10.

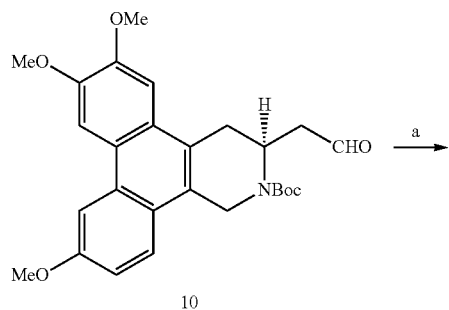

Reagents and conditions: (a) i) NaBH$_4$, MeOH; ii) TFA, CH$_2$Cl$_2$; iii) K$_2$CO$_3$, MgSO$_4$, HCHO, CH$_2$Cl$_2$ The GI$_{50}$'s of both analogs are listed in Table 5.

TABLE 5

GI$_{50}$'s of compound 12 and 13

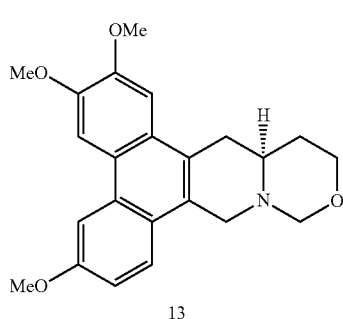

| Compound | Configuration | A549 | DU145 | KB | HCT-8 |
|---|---|---|---|---|---|
| 12 | S | 23 nM | 67 nM | 37 nM | 9 nM |
| 13 | S | 1.79 μM | 1.82 μM | 1.66 μM | 1.45 μM |

Interestingly, a substantial difference was observed between these two isomers. Compound 12 was found to have a potent anticancer activity, especially against A549 and HCT-8, with a GI$_{50}$ of 0.5 nM, whereas compound 13 only has an average GI$_{50}$ around 1-2 μM. Given the similar conformations of both isomers, this could possibly explained by the relative instability of hemiaminal structure in compound 13 under experimental conditions. Although compound 12 has a lower activity in comparison with cryptopleurine, it has a better predicted AUC profile, indicating a relatively lower distribution in brain, which might potentially reduce CNS toxicity.

In conclusion, we have found a series of heteroatom incorporated antofine and cryptopleurine analogs. Compound 12 has the highest anticancer activity and an improved AUC profile, which is promising for further modifications.

Experimental Section (S)—N-Boc-(6,7,10-trimethoxy-1,2,3,4-tetrahydrodibenzo[f,h]isoquinolin-3-yl)methanol (2)

(Boc)$_2$O (3.14 g, 14.40 mmol) was added to amino-alcohol 1 (4.240 g, 12 mmol) in 100 ml of CH$_2$Cl$_2$ and Et$_3$N (6 ml), which was stirred for 2 h. HCl (50 ml, 1N) was added and the organic layer was separated, washed with sat. NaHCO$_3$ and brine, dried over MgSO$_4$. Chromatography gave 5.20 g of white solid. Yield: 95.6%.

General Procedures for the Synthesis of 12N-Substituted Antofines (3a-k):

The N-Boc-aldehyde was obtained using the same procedure as compound 9. A variety of amines were added to the aldehyde (0.1 mmol) in MeOH, followed by addition of AcOH and NaBH$_3$CN, which was stirred at r.t. for 4 h. Sat. NaHCO$_3$ was added to quench the reaction and CH$_2$Cl$_2$ was used for extraction. The residue was purified through a quick TLC column and TFA was used to remove the Boc group. Then TFA was removed by evaporation and the residue was dissolved in CH$_2$Cl$_2$ (10 ml), to which K$_2$CO$_3$ (100 mg) and MgSO$_4$ (0.5 g) were added, followed by HCHO (37%, 0.1 ml). The mixture was stirred at r.t. overnight. Chromatography gave 3a-k as light yellow to white solids. Yield: 40%-80%.

(S)-12-aza-12N-benzyl-antofine (3a)

light yellow solid; mp 113-115° C.; $[\alpha]^{23}_D$=−31.7 (c 0.48, CHCl$_3$); $^1$H NMR (300 MHz, CDCl$_3$): δ 7.87-7.86 (m, 2H), 7.67 (d, J=9.0 Hz, 1H), 7.47-7.40 (m, 5H), 7.22 (dd, J=9.0 Hz, J=2.7 Hz, 1H), 7.14 (s, 1H), 4.59 (d, J=14.4 Hz, 1H), 4.31-4.20 (m, 3H), 4.10 (s, 3H), 4.06-3.87 (m, 4H), 4.03 (s, 3H), 4.01 (s, 3H), 3.31-3.25 (m, 1H), 3.07 (m, 2H); ESI MS m/z 455.15 (M+H)$^+$.

(S)-12-aza-12N-isobutyl-antofine (3b)

yellow solid; mp 93-95° C.; $[\alpha]^{23}_D$=−84.0 (c 0.37, CHCl$_3$); $^1$H NMR (300 MHz, CDCl$_3$): δ 7.88-7.86 (m, 2H), 7.74 (d, J=9.0 Hz, 1H), 7.23 (s, 1H), 7.19 (dd, J=9.0 Hz, J=2.4 Hz, 1H), 4.54 (d, J=14.7 Hz, 1H), 4.14 (d, J=5.4 Hz, 1H), 4.10 (s, 3H), 4.04 (s, 3H), 4.01 (s, 3H), 3.76 (d, J=15.0 Hz, 1H), 3.62 (d, J=5.1 Hz, 1H), 3.41-3.38 (m, 1H), 3.26-3.19 (m, 1H), 2.95-2.83 (m, 3H), 2.58 (d, J=7.2 Hz, 2H), 1.84-1.75 (m, 1H), 1.00-0.98 (d, J=6.0 Hz, 6H); ESI MS m/z 421.10 (M+H)$^+$.

(S)-12-aza-12N-propyl-antofine (3c)

light yellow solid; mp 155-157° C.; $[\alpha]^{23}_D$=−75.4 (c 0.50, CHCl$_3$); $^1$H NMR (300 MHz, CDCl$_3$): δ 7.90 (s, 1H), 7.88 (d, J=2.7 Hz, 1H), 7.76 (d, J=9.0 Hz, 1H), 7.26 (s, 1H), 7.20 (dd, J=9.3 Hz, J=2.4 Hz, 1H), 4.56 (d, J=14.4 Hz, 1H), 4.16 (d, J=5.1 Hz, 1H), 4.11 (s, 3H), 4.05 (s, 3H), 4.01 (s, 3H), 3.77 (d, J=14.7 Hz, 1H), 3.62 (d, J=4.8 Hz, 1H), 3.44-3.40 (m, 1H), 3.30-3.27 (m, 1H), 3.01-2.80 (m, 3H), 2.72 (t, J=7.5 Hz, 2H), 1.64-1.54 (m, 2H), 0.98 (t, J=7.5 Hz, 3H); ESI MS m/z 407.15 (M+H)$^+$.

(S)-12-aza-12N-phenylethylenyl-antofine (3d)

light yellow solid; mp 85-87° C.; $[\alpha]^{23}_D$=−63.2 (c 0.28, CHCl$_3$); $^1$H NMR (300 MHz, CDCl$_3$): δ 7.88-7.87 (m, 2H), 7.74 (d, J=9.0 Hz, 1H), 7.34-7.22 (m, 6H), 7.21 (dd, J=9.0 Hz, J=2.4 Hz, 1H), 4.55 (d, J=14.4 Hz, 1H), 4.23 (d, J=5.1 Hz, 1H), 4.10 (s, 3H), 4.04 (s, 3H), 4.01 (s, 3H), 3.78 (d, J=14.7 Hz, 1H), 3.69 (d, J=5.4 Hz, 1H), 3.54-3.52 (m, 1H), 3.29-3.22 (m, 1H), 3.10-3.05 (m, 2H), 2.83-2.78 (m, 5H); ESI MS m/z 469.20 (M+H)$^+$.

(S)-12-aza-12N-hydroxylethyl-antofine (3e)

white solid; mp 210-212° C.; $[\alpha]^{23}_D$=−57.8 (c 0.36, CHCl$_3$); $^1$H NMR (300 MHz, CDCl$_3$): δ 7.90-7.89 (m, 2H), 7.75 (d, J=9.0 Hz, 1H), 7.24-7.22 (m, 2H), 4.62 (d, J=15.0 Hz, 1H), 4.39 (d, J=6.3 Hz, 1H), 4.11 (s, 3H), 4.03 (s, 3H), 4.02 (s, 3H), 3.83 (d, J=15.0 Hz, 1H), 3.81-3.77 (m, J=5.1 Hz, 2H), 3.71 (d, J=5.4 Hz, 1H), 3.64 (m, 1H), 3.41-3.29 (m, 1H), 3.16-3.11 (m, 3H), 3.02-2.95 (m, 2H); ESI MS m/z 409.15 (M+H)$^+$.

(S)-12-aza-12N-phenyl-antofine (3f)

white solid; mp 244-246° C.; $[\alpha]^{23}_D$=−121.8 (c 0.34, CHCl$_3$); $^1$H NMR (300 MHz, CDCl$_3$): δ 7.88-7.86 (m, 2H), 7.77 (d, J=9.3 Hz, 1H), 7.28 (t, J=7.5 Hz, 2H), 7.25 (s, 1H), 7.21 (dd, J=9.0 Hz, J=2.4 Hz, 1H), 6.74 (t, J=7.5 Hz, 1H), 6.56 (d, J=8.1 Hz, 2H), 4.73 (d, J=3.6 Hz, 1H), 4.65 (d, J=14.4 Hz, 1H), 4.09 (s, 3H), 4.05 (s, 3H), 4.00 (s, 3H), 3.97 (d, J=3.3 Hz, 1H), 3.89 (d, J=14.7 Hz, 1H), 3.74 (dd, J=7.8 Hz, J=5.4 Hz, 1H), 3.43-3.31 (m, 2H), 3.07-3.02 (m, 2H); ESI MS m/z 441.10 (M+H)$^+$.

(S)-12-aza-12N-cyclopropyl-antofine (3g)

white solid; mp 204-206° C.; $[\alpha]^{23}_D$=−87.9 (c 0.34, CHCl$_3$); $^1$H NMR (300 MHz, CDCl$_3$): δ 7.88 (s, 1H), 7.86 (d, J=2.7 Hz, 1H), 7.76 (d, J=9.0 Hz, 1H), 7.25 (s, 1H), 7.18 (dd, J=9.0 Hz, J=2.4 Hz, 1H), 4.55 (d, J=14.7 Hz, 1H), 4.29 (d, J=5.4 Hz, 1H), 4.09 (s, 3H), 4.04 (s, 3H), 4.00 (s, 3H), 3.73 (d, J=14.7 Hz, 1H), 3.59 (d, J=5.4 Hz, 1H), 3.44 (dd, J=8.7 Hz, J=6.0 Hz, 1H), 3.26 (d, J=15.3 Hz, 1H), 2.99-2.92 (m, 2H), 2.88-2.81 (m, 1H), 2.22-2.19 (m, 1H), 0.53-0.45 (m, 4H); ESI MS m/z 405.10 (M+H)$^+$.

(S)-12-aza-12N-methyl-antofine (3h)

white solid; mp 182-184° C.; $[\alpha]^{23}_D$=−45.0 (c 0.34, CHCl$_3$); $^1$H NMR (300 MHz, CDCl$_3$): δ 7.90 (s, 1H), 7.89 (d, J=2.7 Hz, 1H), 7.76 (d, J=9.0 Hz, 1H), 7.26 (s, 1H), 7.19 (dd, J=9.0 Hz, J=2.7 Hz, 1H), 4.57 (d, J=14.7 Hz, 1H), 4.11 (d, J=5.1 Hz, 1H), 4.10 (s, 3H), 4.05 (s, 3H), 4.01 (s, 3H), 3.80 (d, J=15.0 Hz, 1H), 3.62 (d, J=5.1 Hz, 1H), 3.41 (dd, J=8.4 Hz, J=5.1 Hz, 1H), 3.48 (d, J=12.9 Hz, 1H), 3.01-2.95 (m, 2H), 2.85-2.79 (m, 1H), 2.62 (s, 3H); ESI MS m/z 379.05 (M+H)$^+$.

(S)-12-aza-12N-dimethylamino-antofine (3i)

white solid; mp 113-115° C.; $[\alpha]^{23}_D$=−71.9 (c 0.31, CHCl$_3$); $^1$H NMR (300 MHz, CDCl$_3$): δ 7.91 (s, 1H), 7.89 (d, J=2.4 Hz, 1H), 7.77 (d, J=9.0 Hz, 1H), 7.29 (s, 1H), 7.20 (dd, J=9.0 Hz, J=2.7 Hz, 1H), 4.56 (d, J=14.7 Hz, 1H), 4.40 (d, J=6.6 Hz, 1H), 4.11 (s, 3H), 4.06 (s, 3H), 4.01 (s, 3H), 3.70 (d, J=14.7 Hz, 1H), 3.56 (d, J=6.6 Hz, 1H), 3.51 (dd, J=9.0 Hz, J=5.4 Hz, 1H), 3.32 (m, 1H), 3.07-2.95 (m, 2H), 2.84-2.78 (m, 1H), 2.50 (s, 6H); ESI MS m/z 408.10 (M+H)$^+$.

(R)-12-aza-12N-benzyl-antofine (3j)

light yellow solid; mp 95-97° C.; $[\alpha]^{23}_D$=28.6 (c 0.28, CHCl$_3$); $^1$H NMR (300 MHz, CDCl$_3$): δ 7.89 (s, 1H), 7.88 (d, J=2.7 Hz, 1H), 7.74 (d, J=9.0 Hz, 1H), 7.44-7.42 (m, 2H), 7.38-7.27 (m, 3H), 7.25 (s, 1H), 7.19 (dd, J=9.0 Hz, J=2.7 Hz, 1H), 4.55 (d, J=14.4 Hz, 1H), 4.17 (d, J=5.4 Hz, 1H), 4.10 (s, 3H), 4.03 (s, 3H), 4.01 (s, 3H), 3.96 (s, 2H), 3.78 (d, J=14.4 Hz, 1H), 3.60 (d, J=5.4 Hz, 1H), 3.40-3.38 (m, 1H), 3.29-3.26 (m, 1H), 3.00-2.85 (m, 3H); ESI MS m/z 455.20 (M+H)$^+$.

(R)-12-aza-12N-dimethylamino-antofine (3k)

white solid; mp 112-114° C.; $[\alpha]^{23}_D$=65.3 (c 0.28, CHCl$_3$); ESI MS m/z 408.05 (M+H)$^+$. white solid; mp 77-79° C.; $[\alpha]^{23}_D$=54.3° (c 0.93, CHCl$_3$); $^1$H NMR (400 MHz, CDCl$_3$): δ 7.90 (s, 1H), 7.88 (d, J=2.4 Hz, 1H), 7.76 (d, J=9.2 Hz, 1H), 7.27 (s, 1H), 7.19 (dd, J=9.2 Hz, J=2.8 Hz, 1H), 4.55 (d, J=14.4 Hz, 1H), 4.39 (d, J=6.4 Hz, 1H), 4.10 (s, 3H), 4.05 (s, 3H), 4.01 (s, 3H), 3.69 (d, J=14.8 Hz, 1H), 3.55 (d, J=6.4 Hz, 1H), 3.50 (dd, J=8.8 Hz, J=6.0 Hz, 1H), 3.30 (dd, J=15.2 Hz, J=2.4 Hz, 1H), 3.03 (t, J=9.2 Hz, 1H), 3.01-2.95 (m, 1H), 2.81-2.77 (m, 1H), 2.50 (s, 6H); ESI MS m/z 408.05 (M+H)$^+$.

(S)-tert-butyl-6,7,10-trimethoxy-3-((2-methoxy-2-oxoethylamino)methyl)-3,4-dihydrodibenzo[f,h]isoquinoline-2(1H)-carboxylate (4)

The N-Boc-aldehyde was obtained using the same procedure as compound 9. Glycine methyl ester hydrochloride (314 mg, 2.5 mmol) and Et$_3$N (0.35 ml, 2.5 mmol) were added to the aldehyde in MeOH (30 ml), which was stirred for 0.5 h. Then AcOH (0.70 ml, 12 mmol) and NaBH$_3$CN (165 mg, 2.5 mmol) were added. The mixture was stirred for 2 h until all the aldehyde disappeared. Sat. NaHCO$_3$ was used to quench the reaction and CH$_2$Cl$_2$ was used for extraction, and washed with brine, dried over MgSO$_4$. Chromatography gave 635 mg of white solid. Yield: 61% for two steps. mp 78-80° C.; $[\alpha]^{23}_D$=91.6° (c 0.37, CHCl$_3$); $^1$H NMR (400 MHz, CDCl$_3$): δ 7.92 (s, 1H), 7.91 (d, J=2.4 Hz, 1H), 7.87 (brs, 1H), 7.44-7.42 (m, 2H), 7.29 (s, 1H), 7.25-7.23 (m, 1H), 5.40-5.29 (m, 1H), 4.92-4.78 (m, 1H), 4.56 (m, 1H), 4.11 (s, 3H), 4.05 (s, 3H), 4.02 (s, 3H), 3.66 (s, 3H), 3.47-3.36 (m, 2H), 3.27 (dd, J=16.4 Hz, J=6.4 Hz, 1H), 3.14 (d, J=16.4 Hz, 1H), 2.81 (dd, J=12.0 Hz, J=8.8 Hz, 1H), 2.64 (dd, J=12.0 Hz, J=6.4 Hz, 1H), 1.54 (s, 9H); ESI MS m/z 525.20 (M+H)$^+$.

(S)-13N-Boc-11-oxo-13-aza-cryptopleurine (6)

The ester 4 (635 mg, 1.21 mmol) was dissolved in HCl (1.25M in methanol, 15 mL), which was stirred at 50° C. for 1 h. The solvent was removed. 30 mL of MeOH and Et$_3$N (0.3 mL) were added. The mixture was stirred at r.t. for 2 h. After normal workup, chromatography afforded 404 mg of ring-closed intermediate as a white solid. Using similar procedure as compound 2, the intermediate was protected by (Boc)$_2$O to give 456 mg of 6 as a white solid. Yield: 76% over three steps. mp 125-127° C.; $[\alpha]^{23}_D$=−202.8° (c 0.50, CHCl$_3$); $^1$H NMR (400 MHz, CDCl$_3$): δ 7.89 (s, 1H), 7.88 (d, J=2.8 Hz, 1H), 7.87 (d, J=9.2 Hz, 1H), 7.23 (dd, J=9.2 Hz, J=2.8 Hz, 1H), 7.19 (s, 1H), 5.88 (d, J=17.2 Hz, 1H), 4.49 (d, J=17.2 Hz, 1H), 4.40 (d, J=18.0 Hz, 1H), 4.10 (s, 4H), 4.05 (s, 4H), 4.01 (s, 3H), 3.87-3.77 (m, 2H), 3.16 (m, 2H), 1.51 (s, 9H); ESI MS m/z 493.10 (M+H)$^+$, 985.20 (2M+H)$^+$.

(S)-13-aza-13N-Boc-cryptopleurine (7)

To a solution of the amide 6 (456 mg, 0.93 mmol) in THF (30 ml) was added BMS (2M in THF, 2.79 ml), which was stirred at r.t. overnight. 5 ml of MeOH was added and the mixture was refluxed for 1 h. Chromatography afforded 400 mg of white solid. Yield: 90%. mp 116-118° C.; $[\alpha]^{23}_D$=−182.5° (c 0.28, CHCl$_3$); $^1$H NMR (400 MHz, CDCl$_3$): δ 7.88-7.87 (m, 2H), 7.76 (d, J=8.8 Hz, 1H), 7.20 (s, 1H), 7.19 (dd, J=8.8 Hz, J=2.8 Hz, 1H), 4.44 (d, J=15.2 Hz, 1H), 4.29 (m, 1H), 4.11 (m, 1H), 4.09 (s, 3H), 4.05 (s, 3H), 4.00 (s, 3H), 3.66 (d, J=15.2 Hz, 1H), 3.15 (m, 2H), 3.04 (dd, J=16.4 Hz, J=3.2 Hz, 1H), 2.87 (m, 1H), 2.80 (dd, J=16.4 Hz, J=11.8 Hz, 1H), 2.57-2.52 (m, 1H), 2.45 (dt, J=12.0 Hz, 3.2 Hz, 1H); ESI MS m/z 479.10 (M+H)$^+$.

General Procedures for the Synthesis of 13N-Substituted Cryptopleurines (8a-n):

(a) Compound 7 was dissolved in 10 ml of anhydrous CH$_2$Cl$_2$ and Et$_3$N (0.1 ml), to which RCOCl was added at 0° C. The mixture was stirred at r.t. for 4 h before 1N HCl was added. After normal workup, chromatography afforded from light orange to white solids. Yield: 70%-80%. (b) Using the same procedures (reductive amination) as for compound 4. Yield: 50%-80%.

(S)-13-aza-cryptopleurine dihydrochloride (8a)

light yellow solid; mp 228° C. (dec.); $[\alpha]^{23}_D$=−66.7° (c 0.77, DMSO); $^1$H NMR (400 MHz, free amine, CDCl$_3$): δ 7.89 (s, 1H), 7.88 (d, J=2.4 Hz, 1H), 7.77 (d, J=8.8 Hz, 1H), 7.20 (s, 1H), 7.19 (dd, J=8.8 Hz, J=2.8 Hz, 1H), 4.41 (d, J=15.2 Hz, 1H), 4.17 (d, J=5.4 Hz, 1H), 4.09 (s, 3H), 4.05 (s, 3H), 4.00 (s, 3H), 3.96 (s, 2H), 3.67 (d, J=15.2 Hz, 1H), 3.33 (dd, J=12.0 Hz, J=2.0 Hz, 1H), 3.20-3.08 (m, 3H), 3.01 (dd, J=16.0 Hz, J=2.8 Hz, 1H), 2.85-2.78 (m, 2H), 2.61-2.48 (m, 2H); ESI MS m/z 379.10 (M+H)$^+$.

(S)-13-aza-13N-ethyl-cryptopleurine (8b)

yellow solid; mp 83-85° C.; $[\alpha]^{23}_D$=−100.5 (c 0.61, CHCl$_3$); $^1$H NMR (300 MHz, CDCl$_3$): δ 7.91 (s, 1H), 7.90 (d, J=2.7 Hz, 1H), 7.79 (d, J=9.0 Hz, 1H), 7.23 (s, 1H), 7.20 (dd, J=9.0 Hz, J=2.7 Hz, 1H), 4.47 (d, J=14.7 Hz, 1H), 4.10 (s, 3H), 4.06 (s, 3H), 4.01 (s, 3H), 3.70 (d, J=14.7 Hz, 1H), 3.24 (m, 2H), 3.07 (m, 2H), 2.93-2.84 (m, 2H), 2.71-2.63 (m, 2H), 2.54 (q, J=7.2 Hz, 2H), 2.39-2.32 (m, 1H), 2.11 (t, J=10.5 Hz, 1H), 1.18 (t, J=6.9 Hz, 3H); ESI MS m/z 407.15 (M+H)$^+$.

(S)-13-aza-13N-methoxycarbonyl-cryptopleurine (8c)

yellow solid; mp 99-101° C.; $[\alpha]^{23}_D$=−110.4 (c 0.28, CHCl$_3$); $^1$H NMR (300 MHz, CDCl$_3$): δ 7.89-7.88 (m, 2H), 7.75 (d, J=9.0 Hz, 1H), 7.20 (dd, J=8.7 Hz, J=2.4 Hz, 1H), 7.19 (s, 1H), 4.44 (d, J=15.3 Hz, 1H), 4.10 (s, 3H), 4.05 (s, 3H), 4.01 (s, 3H), 3.76 (s, 3H), 3.65 (d, J=15.0 Hz, 1H), 3.30-3.04 (m, 4H), 3.00-2.77 (m, 3H), 2.62-2.42 (m, 2H); ESI MS m/z 437.10 (M+H)$^+$.

(S)-13-aza-13N-acetyl-cryptopleurine (8d)

yellow solid; mp 123-125° C.; $[\alpha]^{23}_D$=−105.3 (c 0.17, CHCl$_3$); $^1$H NMR (300 MHz, CDCl$_3$): δ 7.90 (t, J=3.3 Hz, 2H), 7.79-7.74 (d, J=9.0 Hz, 1H), 7.23-7.18 (m, 2H), 4.84-4.66 (d, J=12.6 Hz, 1H), 4.47 (dd, J=15.6 Hz, J=3.0 Hz, 1H), 4.11 (s, 3H), 4.06 (s, 3H), 4.01 (s, 3H), 3.88-3.48 (m, 2H), 3.26-2.97 (m, 3H), 2.90-2.70 (m, 2H), 2.58-2.39 (m, 2H), 2.20-2.18 (s, 3H); ESI MS m/z 421.10 (M+H)$^+$.

(S)-13-aza-13N-methylsulfonyl-cryptopleurine (8e)

light yellow solid; mp 230° C. (dec.); $[\alpha]^{23}_D$=−66.9 (c 0.16, CHCl$_3$); $^1$H NMR (300 MHz, CDCl$_3$): δ 7.90 (s, 1H), 7.88 (d, J=3.0 Hz, 1H), 7.74 (d, J=9.0 Hz, 1H), 7.20 (dd, J=9.0 Hz, J=2.4 Hz, 1H), 7.15 (s, 1H), 4.45 (d, J=15.6 Hz, 1H), 4.11 (s, 3H), 4.04 (s, 3H), 4.02 (s, 3H), 3.98 (m, 1H), 3.81 (d, J=9.0 Hz, 1H), 3.71 (d, J=16.2 Hz, 1H), 3.26 (d, J=11.7 Hz, 1H), 3.14-3.00 (m, 2H), 2.87 (s, 3H), 2.81-2.60 (m, 4H); ESI MS m/z 457.05 (M+H)$^+$.

(S)-13-aza-13N-methoxycarbonylmethyl-cryptopleurine (8f)

white solid; mp 111-113° C.; $[\alpha]^{23}_D$=−29.2 (c 0.36, CHCl$_3$); $^1$H NMR (300 MHz, CDCl$_3$): δ 7.89 (s, 1H), 7.88 (d, J=3.0 Hz, 1H), 7.76 (d, J=9.0 Hz, 1H), 7.21-7.17 (m, 2H), 4.44 (d, J=15.6 Hz, 1H), 4.10 (s, 3H), 4.04 (s, 3H), 4.01 (s, 3H), 3.77 (s, 3H), 3.70 (d, J=14.4 Hz, 1H), 3.34 (s, 2H), 3.26

(d, J=10.8 Hz, 1H), 3.18 (d, J=11.4 Hz, 1H), 3.04 (m, 2H), 2.88-2.70 (m, 3H), 2.64-2.56 (m, 1H), 2.36-2.30 (m, 1H); ESI MS m/z 451.15 (M+H)+.

(S)-13-aza-13N-cyclopropylmethyl-cryptopleurine (8g)

white solid; mp 160-162° C.; [α]$^{23}$$_D$=−42.6 (c 0.34, CHCl$_3$); $^1$H NMR (300 MHz, CDCl$_3$): δ 7.91 (s, 1H), 7.89 (d, J=2.4 Hz, 1H), 7.79 (d, J=9.0 Hz, 1H), 7.24 (s, 1H), 7.20 (dd, J=9.0 Hz, J=2.4 Hz, 1H), 4.48 (d, J=15.6 Hz, 1H), 4.10 (s, 3H), 4.06 (s, 3H), 4.01 (s, 3H), 3.69 (d, J=15.6 Hz, 1H), 3.37 (d, J=10.2 Hz, 1H), 3.19 (t, J=13.2 Hz, 2H), 3.15-3.06 (m, 1H), 2.92-2.83 (m, 1H), 2.78-2.65 (m, 2H), 2.43-2.38 (m, 1H), 2.37 (d, J=6.6 Hz, 2H), 2.14 (t, J=10.5 Hz, 1H), 0.96-0.89 (m, 1H), 0.58 (d, J=7.8 Hz, 2H), 0.19 (d, J=5.4 Hz, 2H); ESI MS m/z 433.15 (M+H)+.

(S)-13-aza-13N-cyclopropyl-cryptopleurine (8h)

white solid; mp 115-117° C.; [α]$^{23}$$_D$=−104.6 (c 0.28, CHCl$_3$); $^1$H NMR (300 MHz, CDCl$_3$): δ 7.89 (s, 1H), 7.88 (d, J=2.7 Hz, 1H), 7.76 (d, J=9.0 Hz, 1H), 7.21 (s, 1H), 7.19 (dd, J=9.3 Hz, J=2.7 Hz, 1H), 4.49 (d, J=15.6 Hz, 1H), 4.10 (s, 3H), 4.04 (s, 3H), 4.00 (s, 3H), 3.69 (d, J=14.4 Hz, 1H), 3.34 (d, J=10.8 Hz, 1H), 3.26-3.18 (m, 1H), 3.13-3.02 (m, 2H), 2.97-2.80 (m, 1H), 2.72-2.57 (m, 3H), 2.52-2.40 (m, 1H), 1.79-1.72 (m, 1H), 0.54-0.52 (m, 4H); ESI MS m/z 419.10 (M+H)+.

(S)-13-aza-13N-benzoyl-cryptopleurine (8i)

white solid; mp 203° C. (dec.); [α]$^{23}$$_D$=−66.6 (c 0.50, CHCl$_3$); $^1$H NMR (300 MHz, CDCl$_3$): δ 7.87 (brs, 2H), 7.72 (brs, 1H), 7.51-7.45 (m, 5H), 7.19 (dd, J=9.0 Hz, J=2.4 Hz, 1H), 7.06 (s, 1H), 4.88-4.81 (m, 1H), 4.44 (m, 1H), 4.09-4.00 (s, 9H), 3.85-3.46 (m, 2H), 3.27-3.08 (m, 3H), 2.85-2.70 (m, 2H), 2.58-2.41 (m, 2H); ESI MS m/z 483.15 (M+H)+.

(S)-13-aza-13N-hydroxylethyl-cryptopleurine (8j): light yellow solid; mp 266° C. (dec.); [α]$^{23}$$_D$=−56.0 (c 0.15, CHCl$_3$); $^1$H NMR (300 MHz, CDCl$_3$): δ 7.90-7.88 (m, 2H), 7.78 (d, J=9.0 Hz, 1H), 7.20 (dd, J=9.0 Hz, J=2.7 Hz, 1H), 7.19 (s, 1H), 4.46 (d, J=15.0 Hz, 1H), 4.10 (s, 3H), 4.04 (s, 3H), 4.01 (s, 3H), 3.71 (t, J=5.1 Hz, 2H), 3.67 (d, J=14.7 Hz, 1H), 3.21-3.19 (m, 2H), 3.06-2.97 (m, 2H), 2.90-2.81 (m, 1H), 2.65 (t, J=5.4 Hz, 2H), 2.62-2.47 (m, 3H), 2.25 (t, J=10.5 Hz, 1H); ESI MS m/z 423.15 (M+H)+.

(S)-13-aza-13N-dimethoxyphosphoryl-cryptopleurine (8k)

light yellow solid; mp 98-100° C.; [α]$^{23}$$_D$=−92.4 (c 0.25, CHCl$_3$); $^1$H NMR (300 MHz, CDCl$_3$): δ 7.89-7.88 (m, 2H), 7.76 (d, J=9.3 Hz, 1H), 7.19 (dd, J=9.0 Hz, J=2.7 Hz, 1H), 7.18 (s, 1H), 4.44 (d, J=15.6 Hz, 1H), 4.09 (s, 3H), 4.04 (s, 3H), 4.01 (s, 3H), 3.77 (d, J=3.3 Hz, 3H), 3.73 (d, J=3.0 Hz, 3H), 3.67 (m, 2H), 3.58 (m, 1H), 3.24-3.13 (m, 2H), 3.06 (dd, J=16.2 Hz, J=3.3 Hz, 1H), 2.94-2.75 (m, 2H), 2.62-2.46 (m, 2H); ESI MS m/z 487.15 (M+H)+.

(R)-13-aza-13N-dimethylcarbamyl-cryptopleurine (8l)

yellow solid; mp 206-208° C.; [α]$^{23}$$_D$=139 (c 0.3, CHCl$_3$); $^1$H NMR (300 MHz, CDCl$_3$): δ 7.89-7.88 (m, 2H), 7.76 (d, J=9.0 Hz, 1H), 7.21 (s, 1H), 7.19 (dd, J=9.0 Hz, J=2.1 Hz, 1H), 4.45 (d, J=15.3 Hz, 1H), 4.10 (s, 3H), 4.06 (s, 3H), 4.01 (s, 3H), 3.90 (m, 1H), 3.75-3.65 (m, 1H), 3.68 (d, J=15.6 Hz, 1H), 3.26-3.15 (m, 2H), 3.09-3.04 (m, 1H), 2.95-2.85 (m, 2H), 2.90 (s, 6H), 2.67-2.55 (m, 2H); ESI MS m/z 450.15 (M+H)+.

(R)-13-aza-13N-isobutyl-cryptopleurine (8m)

white solid; mp 175-177° C.; [α]$^{23}$$_D$=98.2 (c 1.1, CHCl$_3$); $^1$H NMR (300 MHz, CDCl$_3$): δ 7.87-7.86 (m, 2H), 7.74 (d, J=9.0 Hz, 1H), 7.20 (dd, J=9.0 Hz, J=2.7 Hz, 1H), 7.18 (s, 1H), 4.53 (d, J=15.3 Hz, 1H), 4.10 (s, 3H), 4.05 (s, 3H), 4.01 (s, 3H), 3.80 (m, 1H), 3.37-3.28 (m, 2H), 3.18-3.09 (m, 2H), 2.95-2.86 (m, 2H), 2.63-2.60 (m, 2H), 2.42 (d, J=6.6 Hz, 2H), 2.41 (m, 1H), 1.98 (m, 1H), 1.01 (s, 3H), 0.99 (s, 3H); ESI MS m/z 435.10 (M+H)+.

(R)-13-aza-13N-benzyl-cryptopleurine (8n)

white solid; mp 86-88° C.; [α]$^{23}$$_D$=31.9 (c 3.3, CHCl$_3$); $^1$H NMR (300 MHz, CDCl$_3$): δ 7.87 (s, 2H), 7.76 (d, J=9.0 Hz, 1H), 7.42-7.30 (m, 5H), 7.18 (dd, J=9.6 Hz, J=2.4 Hz, 1H), 7.15 (s, 1H), 4.45 (d, J=15.3 Hz, 1H), 4.08 (s, 3H), 4.01 (s, 3H), 4.00 (s, 3H), 3.70 (d, J=16.5 Hz, 1H), 3.67 (d, J=12.9 Hz, 1H), 3.56 (d, J=12.9 Hz, 1H), 3.21-3.12 (m, 2H), 3.00-2.96 (m, 2H), 2.87-2.78 (m, 1H), 2.70-2.63 (m, 2H), 2.49-2.42 (m, 1H), 2.14 (t, J=10.2 Hz, 1H); ESI MS m/z 469.15 (M+H)+.

(S,E)-6,7,10-trimethoxy-3-(2-methoxyvinyl)-1,2,3,4-tetrahydrodibenzo[f,h]isoquinoline (9)

N-Boc-alcohol 2 (1.812 g, 4 mmol) was dissolved in CH$_2$Cl$_2$ (50 ml) and Et$_3$N (1.95 ml, 14 mmol) at 0° C., to which Py.SO$_3$ (2.23 g, 14 mmol) in 10 ml of DMSO was added dropwise. The ice bath was then removed and the mixture was stirred at r.t. until alcohol disappeared by TLC. HCl (1N) was added, and the organic layer was then separated and washed with sat. NaHCO$_3$, brine, and dried over MgSO$_4$. In another flask, Ph$_3$P$^+$CH$_2$OMeCl$^−$ (2.74 g, 8 mmol) was added to KOtBu (875 mg, 7.8 mmol) at 0° C. under N$_2$, which was stirred for 0.5 h. The aldehyde in 20 ml of CH$_2$Cl$_2$ was added dropwise, followed by removal of ice bath. The reaction was kept for 2-3 h before sat. NH$_4$Cl was poured into the mixture. CH$_2$Cl$_2$ was used for extraction and the organic layers were washed with sat. NaHCO$_3$ and brine, dried over MgSO$_4$. Chromatography afforded 1.5 g of light yellow solid. Yield: 78% for two steps. mp 150-152° C.; [α]$^{23}$$_D$=108.1° (c 0.59, CHCl$_3$); $^1$H NMR (400 MHz, CDCl$_3$, E/Z=2.5:1): δ 7.94-7.91 (m, 2H), 7.88 (d, J=9.2 Hz, 1H), 7.29 (s, 1H), 7.26-7.22 (m, 1H), 6.30 (d, J=12.8 Hz, 0.68H, E isomer), 5.86 (dd, J=6.4 Hz, J=1.6 Hz, 0.28 Hz, Z isomer), 5.72 (m, 0.31H, Z isomer), 5.30-5.25 (d, J=16.8 Hz, 1H+0.67H, E isomer), 4.80 (dd, J=12.8 Hz, J=8.4 Hz, 0.71H, E isomer), 4.59 (d, J=17.2 Hz, 1H), 4.42 (dd, J=8.0 Hz, J=6.4 Hz, 0.29H, Z isomer), 4.12-4.11 (m, 3H), 4.05-4.04 (m, 3H), 4.03-4.02 (m, 3H), 3.62 (s, 0.7111, Z isomer), 3.44-3.32 (m, 1H), 3.36 (s, 211, E isomer), 3.13 (d, J=16.0 Hz, 1H), 1.55 (s, 9H); ESI MS m/z 480.05 (M+H)+.

(S)-2-(6,7,10-trimethoxy-1,2,3,4-tetrahydrodibenzo [f,h]isoquinolin-3-yl)acetaldehyde (10)

The alkene 9 (1.5 g, 3.12 mmol) was dissolved in THF (50 ml) and H$_2$O (5 ml), to which Hg(OAc)$_2$ (3.0 g, 9.36 mmol) was added at 0° C. Then the ice bath was removed and the mixture was stirred overnight. Freshly prepared Sat. KI (50 ml) was added dropwise at 0° C. for 10 min, and CH$_2$Cl$_2$ was used for extraction. The organic layers were collected and washed with brine, dried over MgSO₄. Chromatography furnished 1.09 g of light yellow foam. Yield: 75%. mp 98-100° C.; [α]²³_D=94.4° (c 0.68, CHCl₃); ¹H NMR (400 MHz, CDCl₃): δ 9.79 (s, 1H), 7.93 (s, 1H), 7.91 (d, J=2.4 Hz, 1H), 7.85 (brs, 1H), 7.26-7.24 (m, 2H), 5.38-5.29 (m, 2H), 4.58 (d, J=16.0 Hz, 1H), 4.11 (s, 3H), 4.05 (s, 3H), 4.02 (s, 3H), 3.38 (dd, J=16.0 Hz, J=6.4 Hz, 1H), 3.12 (d, J=16.4 Hz, 1H), 2.70-2.59 (m, 2H), 1.53 (s, 9H); ESI MS m/z 466.10 (M+H)⁺, 488.15 (M+Na)⁺.

General Procedures for the Synthesis of 12N-Substituted Cryptopleurines (11a-g):

as with general procedures for 12N-substituted antofines 3a-k. Yield: 50%-70%.

(S)-12-aza-12N-hydroxylethyl-cryptopleurine (11a)

white solid; mp 138-140° C.; [α]²³_D=116.1 (c 0.28, CHCl₃); ¹H NMR (300 MHz, CDCl₃): δ 7.88-7.87 (m, 2H), 7.73 (d, J=9.0 Hz, 1H), 7.21 (s, 1H), 7.18 (dd, J=9.0 Hz, J=2.4 Hz, 1H), 4.34 (d, J=14.7 Hz, 1H), 4.09 (s, 3H), 4.04 (s, 3H), 4.00 (s, 3H), 3.75-3.69 (m, 1H), 3.65 (t, J=4.5 Hz, 1H), 3.57 (d, J=14.7 Hz, 1H), 3.13-3.06 (m, 3H), 2.95-2.89 (m, 1H), 2.84-2.81 (m, 2H), 2.65-2.46 (m, 3H), 1.92-1.86 (m, 2H); ESI MS m/z 423.10 (M+H)⁺.

(S)-12-aza-12N-phenyl-cryptopleurine (11b)

white solid; mp 225-227° C.; [α]²³_D=-85.6 (c 0.25, CHCl₃); ¹H NMR (300 MHz, CDCl₃): δ 7.88 (s, 2H), 7.78 (d, J=9.0 Hz, 1H), 7.27 (t, J=7.8 Hz, 2H), 7.22-7.18 (m, 2H), 7.09 (d, J=8.1 Hz, 2H), 6.87 (t, J=6.9 Hz, 1H), 4.77 (d, J=11.1 Hz, 1H), 4.44 (d, J=15.3 Hz, 1H), 4.09 (s, 3H), 4.03 (s, 3H), 4.01 (s, 3H), 3.85 (d, J=12.9 Hz, 1H), 3.63 (d, J=15.3 Hz, 1H), 3.57 (d, J=10.8 Hz, 1H), 3.19-3.06 (m, 2H), 2.93-2.84 (m, 1H), 2.60 (m, 1H), 1.95-1.87 (m, 2H); ESI MS m/z 455.10 (M+H)⁺.

(S)-12-aza-12N-isobutyl-cryptopleurine (11c)

light yellow solid; mp 177-179° C.; [α]²³_D=-83.7 (c 0.30, CHCl₃); ¹H NMR (300 MHz, CDCl₃): δ 7.86 (s, 2H), 7.70 (d, J=9.3 Hz, 1H), 7.18 (dd, J=9.0 Hz, J=2.7 Hz, 1H), 7.17 (s, 1H), 4.42 (d, J=15.9 Hz, 1H), 4.08 (s, 3H), 4.02 (s, 3H), 3.99 (s, 3H), 3.65 (d, J=14.7 Hz, 1H), 3.12-2.87 (m, 5H), 2.50-2.37 (m, 2H), 2.36 (d, J=7.2 Hz, 2H), 1.94-1.81 (m, 3H), 0.96 (d, J=6.6 Hz, 61-1); ESI MS m/z 435.15 (M+H)⁺.

(S)-12-aza-12N-benzyl-cryptopleurine (11d)

white solid; mp 211-213° C.; [α]²³_D=-80.5 (c 0.41, CHCl₃); ¹H NMR (300 MHz, CDCl₃): δ 7.88-7.87 (m, 2H), 7.72 (d, J=9.0 Hz, 1H), 7.44-7.27 (m, 5H), 7.23 (s, 1H), 7.16 (dd, J=9.0 Hz, J=2.4 Hz, 1H), 4.32 (d, J=15.3 Hz, 1H), 4.09 (s, 3H), 4.05 (s, 3H), 4.01 (m, 3H), 3.99 (s, 3H), 3.70 (s, 2H), 3.56 (d, J=15.0 Hz, 1H), 3.12-3.05 (m, 2H), 2.96-2.91 (m, 1H), 2.86 (d, J=9.0 Hz, 1H), 2.44-2.29 (m, 2H), 1.94-1.83 (m, 2H); ESI MS m/z 469.15 (M+H)⁺.

(S)-12-aza-12N-cyclopropyl-cryptopleurine (11e)

white solid; mp 164-166° C.; [α]²³_D=-105.4 (c 0.50, CHCl₃); ¹H NMR (300 MHz, CDCl₃): δ 7.88-7.87 (m, 2H), 7.74 (d, J=9.0 Hz, 1H), 7.21 (s, 1H), 7.18 (dd, J=9.0 Hz, J=2.4 Hz, 1H), 4.38 (d, J=14.4 Hz, 1H), 4.16 (d, J=9.0 Hz, 1H), 4.08 (s, 3H), 4.04 (s, 3H), 3.99 (s, 3H), 3.59 (d, J=15.3 Hz, 1H), 3.20 (m, 1H), 3.09-3.01 (m, 2H), 2.94-2.85 (m, 1H), 2.58- 2.41 (m, 2H), 1.99-1.94 (m, 1H), 1.87-1.84 (m, 2H), 0.57-0.49 (m, 4H); ESI MS m/z 419.10 (M+H)⁺.

(S)-12-aza-12N-dimethylamino-cryptopleurine (11f)

white solid; mp 225-227° C.; [α]²³_D=-86.4 (c 0.50, CHCl₃); ¹H NMR (300 MHz, CDCl₃): δ 7.89-7.88 (m, 2H), 7.76 (d, J=9.0 Hz, 1H), 7.23 (s, 1H), 7.20 (dd, J=9.0 Hz, J=2.4 Hz, 1H), 4.42 (d, J=14.7 Hz, 1H), 4.20 (d, J=7.8 Hz, 1H), 4.09 (s, 3H), 4.05 (s, 3H), 4.00 (s, 3H), 3.65 (d, J=14.7 Hz, 1H), 3.18-3.06 (m, 2H), 3.04 (d, J=8.1 Hz, 1H), 2.88 (dd, J=15.6 Hz, J=10.5 Hz, 1H), 2.52 (s, 6H), 2.48 (m, 1H), 2.31-2.24 (m, 1H), 2.01-1.83 (m, 2H); ESI MS m/z 422.15 (M+H)⁺.

(R)-12-aza-12N-isobutyl-cryptopleurine (11g)

light yellow solid; mp 175-177° C.; [α]²³_D=85.0 (c 0.38, CHCl₃); ¹H NMR (300 MHz, CDCl₃): δ 7.87 (m, 2H), 7.64 (d, J=9.0 Hz, 1H), 7.22 (dd, J=9.0 Hz, J=2.4 Hz, 1H), 7.16 (s, 1H), 4.85 (d, J=15.3 Hz, 1H), 4.56 (d, J=9.3 Hz, 1H), 4.09 (s, 3H), 4.04 (s, 3H), 4.00 (s, 3H), 3.76 (d, J=9.9 Hz, 1H), 3.34-3.17 (m, 3H), 3.03 (m, 2H), 2.79 (m, 2H), 2.21 (m, 1H), 2.04-1.89 (m, 2H), 1.00-0.98 (s, 6H); ESI MS m/z 435.20 (M+H)⁺.

(S)-13-oxa-cryptopleurine (12)

Amino-alcohol 1 (177 mg, 0.5 mmol) was suspended in dry CH₂Cl₂ (15 ml) and Et₃N (0.14 ml, 1.00 mmol) at 0° C., to which chloroacetyl chloride (40 μl, 0.50 mmol) in 10 ml of CH₂Cl₂ was added dropwise. The mixture was stirred at 0° C. for 5 h before 1N HCl was added. The organic layer was separated and washed with sat. NaHCO₃ and brine, dried over MgSO₄. CH₂Cl₂ was removed and the residue was dissolved in anhydrous THF (5 ml), to which NaH (2 equiv.) was added at r.t. followed by reflux for 2 h. Sat. NH₄Cl was added and CH₂Cl₂ was used for extraction. After workup, the organic layer was dried over MgSO₄. Then the residue was dissolved in 10 ml anhydrous THF, BMS (1.50 ml, 6 mmol) was added, which was stirred at r.t. overnight. MeOH (5 ml) was added and the mixture was refluxed for 1 h. Chromatography gave 73 mg of off-white solid. Yield: 38.5% for three steps; mp 199-201° C.; [α]²³_D=-134.6 (c 0.52, CHCl₃); ¹H NMR (300 MHz, CDCl₃): δ 7.86-7.85 (m, 2H), 7.74 (d, J=9.0 Hz, 1H), 7.18 (dd, J=9.0 Hz, J=2.4 Hz, 1H), 7.14 (s, 1H), 4.39 (d, J=15.6 Hz, 1H), 4.12 (m, 2H), 4.08 (s, 3H), 4.03 (s, 3H), 4.00 (s, 3H), 3.91-3.83 (m, 1H), 3.66 (d, J=15.6 Hz, 1H), 3.51 (dd, J=11.1 Hz, J=9.0 Hz, 1H), 3.06 (d, J=11.7 Hz, 1H), 2.91-2.87 (m, 1H), 2.76-2.59 (m, 3H); ESI MS m/z 380.05 (M+H)⁺.

(S)-12-oxa-cryptopleurine (13)

The aldehyde 10 (100 mg, 0.21 mmol) was dissolved in MeOH, to which NaBH₄ (19 mg, 0.50 mmol) was added in one portion. The mixture was stirred for 1 h and Sat. NaHCO₃ was added. After Normal workup, 80 mg of white solid was obtained, which was used without further purification. The residue was dissolved in CH₂Cl₂ (10 ml), to which MgSO₄, K₂CO₃, and HCHO were added sequentially. The mixture was stirred overnight. After normal workup, chromatography gave 32 mg of white solid. Yield: 40% for two steps; mp 195-197° C.; [α]²³_D=-56.8 (c 0.60, CHCl₃); ¹H NMR (300 MHz, CDCl₃): δ 7.89-7.88 (m, 2H), 7.75 (d, J=9.3 Hz, 1H), 7.22 (s, 1H), 7.19 (dd, J=9.0 Hz, J=2.7 Hz, 1H), 4.79 (d, J=8.4 Hz, 1H), 4.41 (d, J=15.3 Hz, 1H), 4.19 (dd, J=11.1 Hz, J=5.1 Hz, 1H), 4.10 (s, 4.05 (s, 3H), 4.03 (s, 1H), 4.01 (s, 3H), 3.75-3.65 (m, 2H), 3.17 (dd, J=15.9 Hz, J=3.6 Hz, 1H), 2.95-2.80 (m, 2H), 2.06-1.92 (m, 1H), 1.74 (m, 1H); ESI MS m/z 380.05 (M+H)+.

Compounds, schemes and tables are numbered separately in the Examples below from the Examples above.

EXAMPLE 3A

Boc group using TFA. Then the diastereomers underwent reduction using LiAlH$_4$ to afford the goal product 3a and 3b in a ratio of 2:1.

EXAMPLE 3B

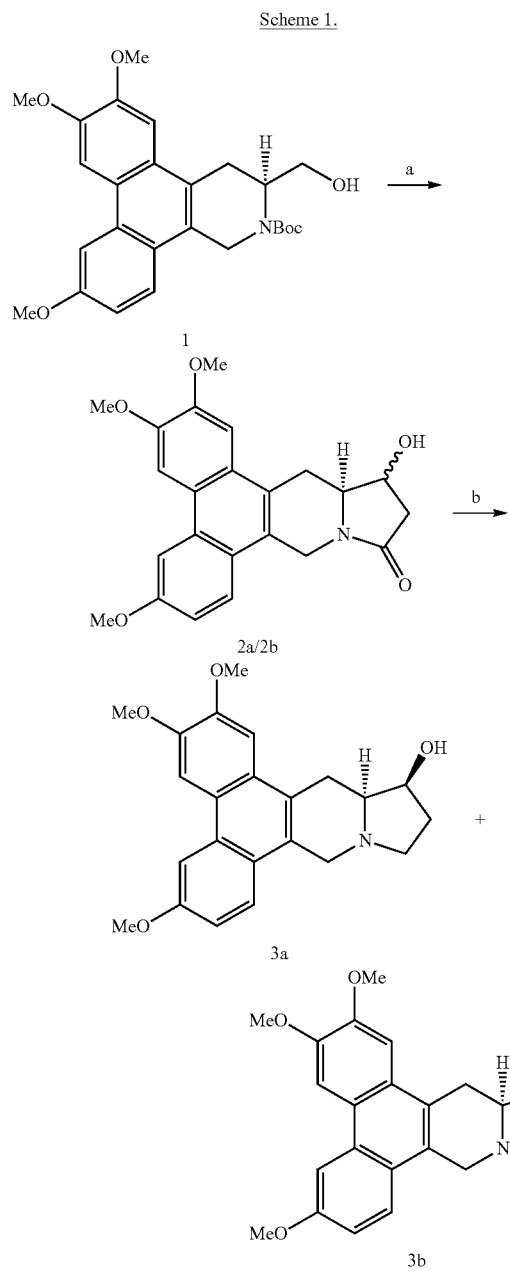

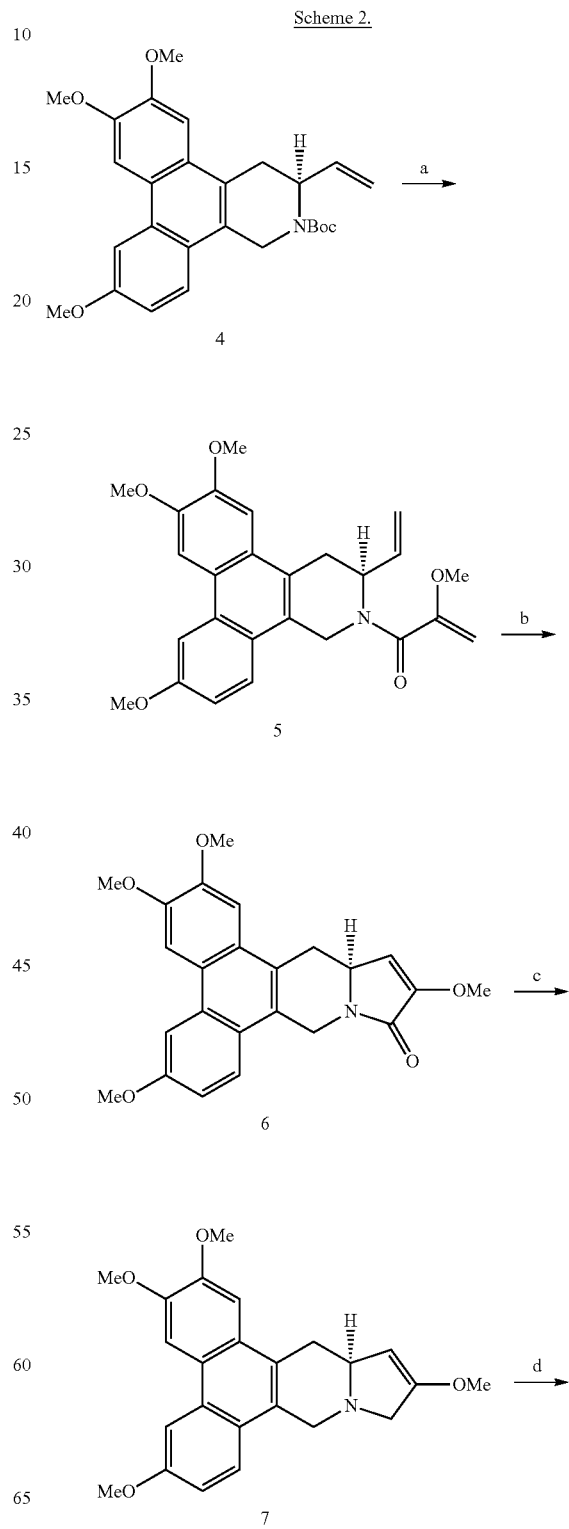

Reagents and conditions: (a) i) Py·SO$_3$, DMSO, Et$_3$N, CH$_2$Cl$_2$; ii) LiHMDs, EtOAc, −78° C., THF; iii) TFA, CH$_2$Cl$_2$; iv) Et$_3$N, MeOH, reflux, 57% over four steps (b) LiAlH$_4$, THF, 70%

Compound 1 was first oxidized to aldehyde followed by reaction with ethyl acetate under LiHMDs at −78° C. to give a mixture of diastereomeric intermediates, which were converted to inseparable compounds 2a/b after removal of the -continued

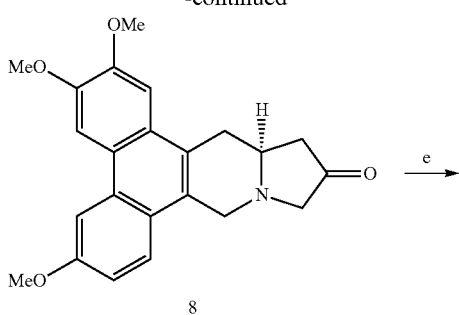
8

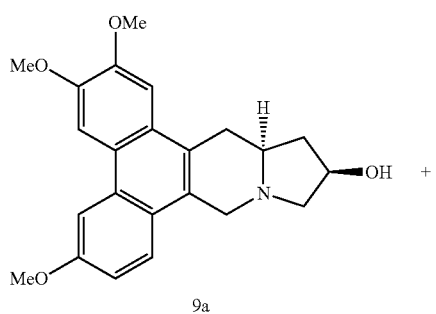
9a

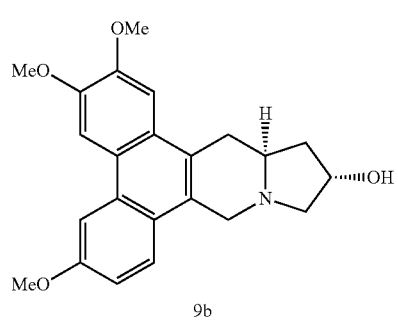
9b

Reagents and conditions: (a) i) TFA, CH₂Cl₂; ii) 2-methylacrylic acid, EDC, HOBt, DMF, 83% over two steps (b) Grubb's 2nd generation catalyst, CH₂Cl₂, 88% (c) LiAlH₄, THF, 69% (d) HCl, THF, reflux, 68% (e) NaBH₄, MeOH, r.t., 80%, 9a/9b = 5/3

Compound 4 was condensed with 2-methoxyacrylic acid to form amide 5 after removal of the Boc group by TFA. Ring closure then took place to give compound 6 through intromolecular metathesis using G2 catalyst, which was subsequently reduced to give amine 7 before being subject to HCl to furnish the rearrangement product ketone 8. At last, the carbonyl group was reduced to give the goal product 9a and 9b in a ratio of 5:3.

EXAMPLE 3C

Scheme 3.

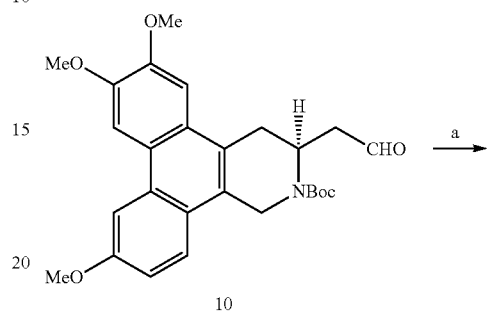
10

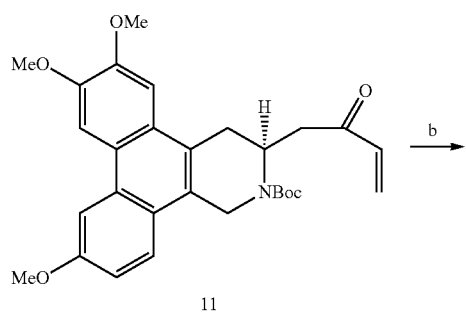
11

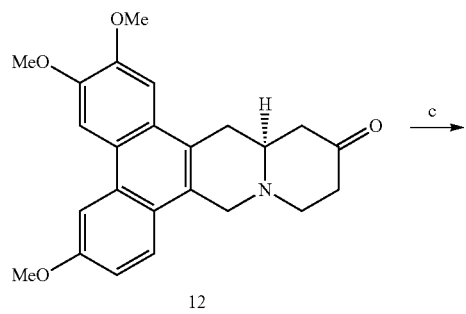
12

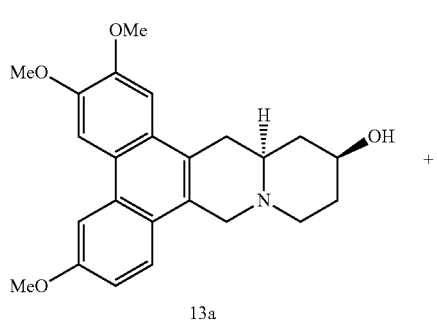
13a

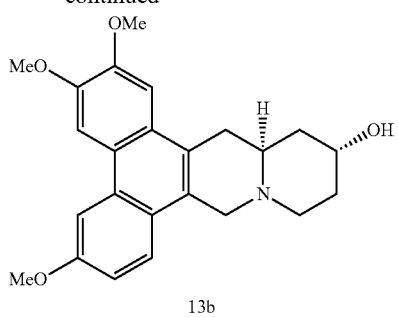

13b

Reagents and conditions: (a) i) vinylmagnesium bromide, THF, 0° C. ii) Dess-Martin reagent, CH₂Cl₂, 57% over two steps (b) i) TFA, CH₂Cl₂; ii) Cs₂CO₃, MeOH, reflux, 63% over two steps (c) NaBH₄, MeOH, 13a:13b = 3:7, 80% or L-selectride, THF, 0° C., 13a:13b = 1:9, 90%

Aldehyde 10 was reacted with vinylmagnesium bromide to give a mixture of alcohols, which were converted to α,β-unsaturated ketone 11 using Dess-Martin reagent. The ring closure step was accomplished through intramolecular Michael addition to give 12 after removal of the Boc group. At last, the ketone was reduced either using NaBH₄ to give compound 13a and 13b in a ration of 3:7 or using L-selectride to afford both compounds with a much higher diastereomeric selectivity (1:9). Compound 13a and 13b can also be obtained using a similar method as described in Scheme 1 in about 1:1 ratio (not shown).

EXAMPLE 3D

Scheme 4.

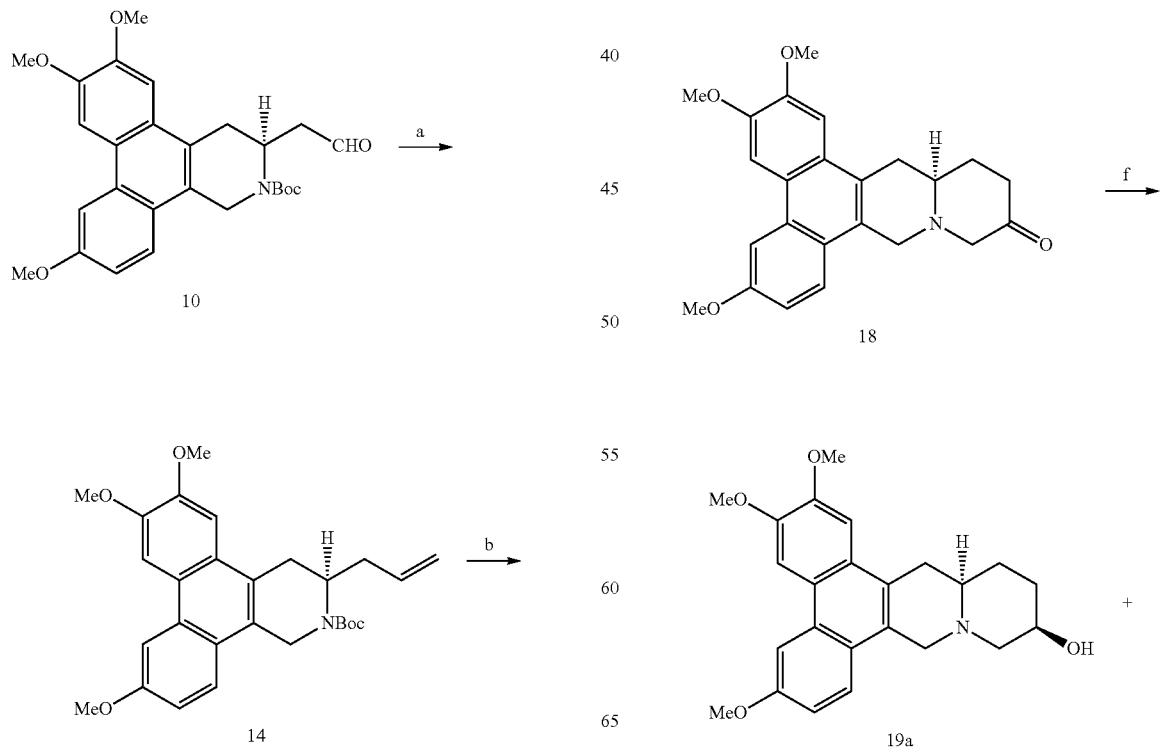

-continued

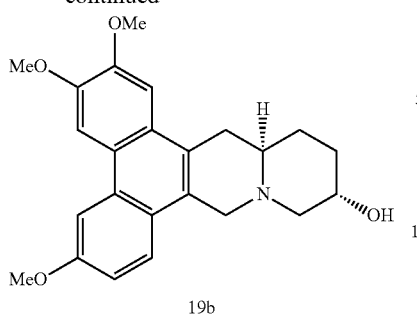

19b

Reagents and conditions: (a) Ph₃P═CH₂Br, n-BuLi, THF, 85% (b) i) TFA, CH₂Cl₂; ii) 2-methoxyacrylic acid, EDC, HOBt, DMF, 77% (c) Grubb's 2nd generation catalyst, CH₂Cl₂, reflux, 65% (d) LiAlH₄, THF, 70% (e) HCl, THF, reflux, 80% (f) NaBH₄, MeOH, 19a:19b = 4:1, 73% or L-selectride, THF, 0° C., 19a (80%), 19b (0%)

Aldehyde 10 was converted to alkene 14 through Wittig reaction using Ph₃P═CH₂Br, which was then condensed with 2-methoxyacrylic acid to give amide 15 after removal of the Boc group. Ring-closing metathesis was again used to afford compound 16 followed by reduction to amine 17 using LiAlH₄. The ketone 18 was obtained through enol rearrangement under acidic condition and then reduced to alcohol 19a and 19b using NaBH₄ in a ratio of 4:1 or L-selectride, in which case only 19a was isolated.

EXAMPLE 3E

Scheme 5.

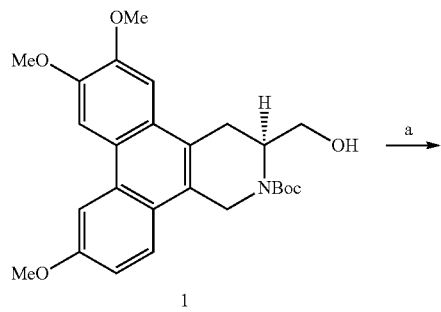

1

-continued

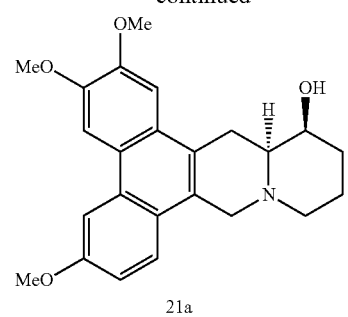

21a

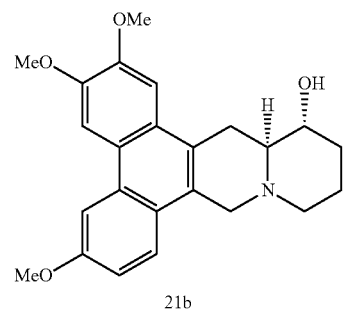

21b

Reagents and conditions: (a) i) Py•SO₃, DMSO, Et₃N, CH₂Cl₂; ii) LiHMDs, methyl propiolate, -78° C., THF; iii) Pd/C, H₂, MeOH; iv) TFA, CH₂Cl₂; v) Et₃N, MeOH, reflux, 47% over five steps (b) BMS, THF, 41%

Compound 1 was oxidized to aldehyde by Py.SO₃ before nucleophilic addition of lithium propiolate prepared in situ. The intermediate alcohol was then subject to hydrogenation and subsequent cyclization to give a mixture of inseperable 20a/20b after removal of the Boc group. ¹H NMR indicated the two diastereomers were present in about 1:1 ratio. At last, the goal products 21a and 21b were obtained by reduction in a yield of 41%.

EXAMPLE 3F

Scheme 6.

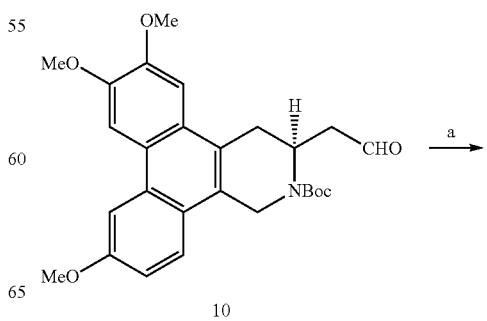

10

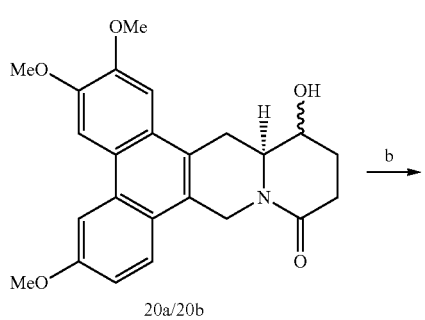

20a/20b

-continued

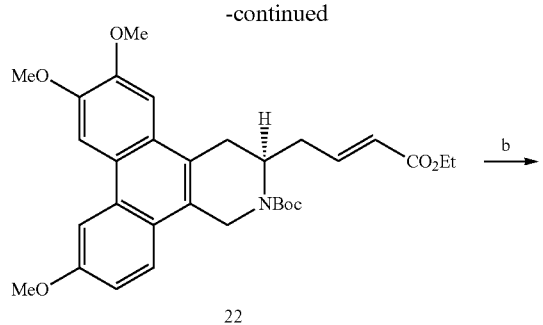

22

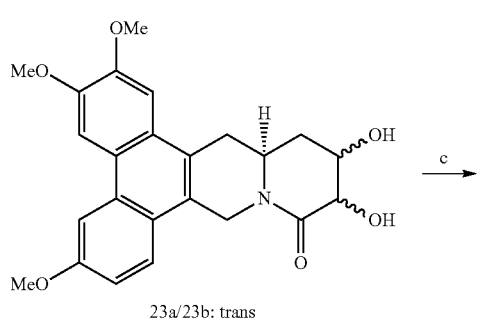

23a/23b: trans

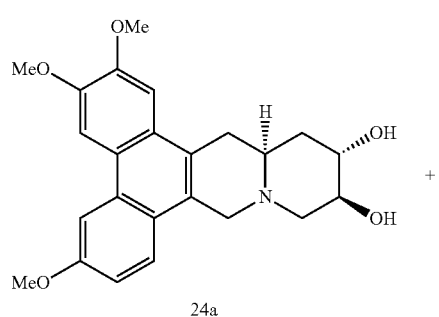

24a

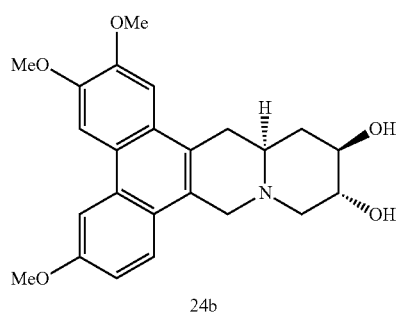

24b

Reagents and conditions: (a) Ph₃P═CH₂CO₂Et, THF, 89% (b) i) OsO₄, NMO, Acetone/H₂O = 8/1, overnight; ii) TFA, CH₂Cl₂; iii) TEA, MeOH, reflux, 67% over three steps (c) BMS, THF, 37%

Compound 10 was converted to E alkene using Wittig reagent Ph₃P═CH₂CO₂Et in a yield of 89%. The double bond was then oxidized with OsO₄ and NMO to give a dihydroxylated intermediate, which was cyclized to give a mixture of 23a/23b after the Boc group was removed. ¹H NMR indicated that the diastereomeric ratio was about 5:4. At last, the amide was reduced using BMS to furnish the goal products 24a and 24b.

EXAMPLE 3G

Scheme 7.

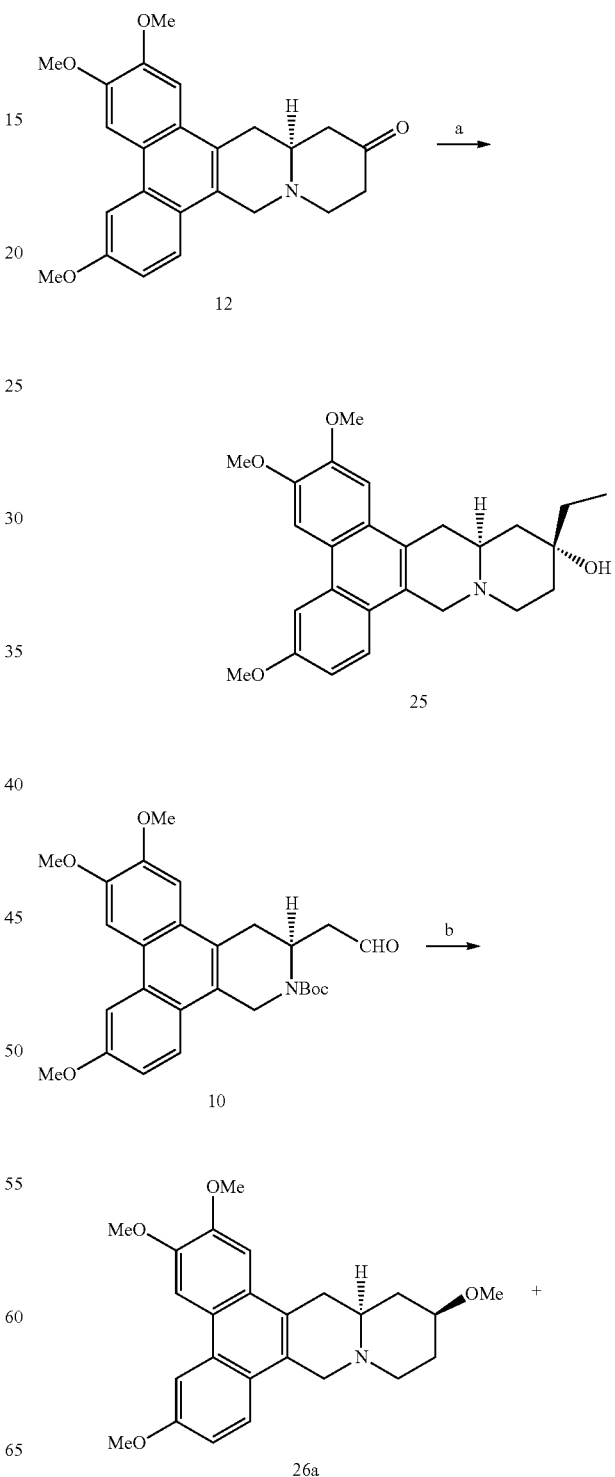

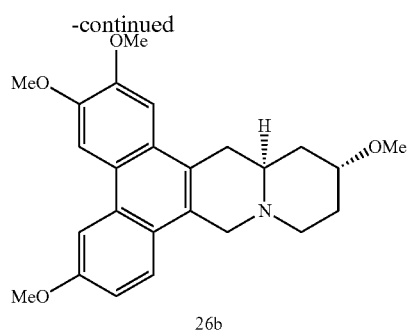

26b

Reagents and conditions: (a) EtMgBr, THF, 0° C., 51% (b) i) LiHMDs, ethyl acetate, THF, -78° C.; ii) TFA, CH$_2$Cl$_2$; iii) MeOH, Et$_3$N; iv) Me$_2$SO$_4$, NaH, THF; v) BMS, THF, 17% over five steps The ketone 12 was converted to tertiary alcohol 25 using EtMgBr at 0° C., and only the 13R diastereomer was isolated. Since direct methylation of compound 13b failed to give 13-methoxy-cryptopleurine 26b, compound 26a and 26b were prepared as follows: compound 10 was subject to nucleophilic addition with ethyl acetate using LiHMDs at −78° C. to give alcohols, which then underwent cyclization after removal of the Boc group. The hydroxyl group was then methylated using Me$_2$SO$_4$ and NaH and the amide was reduced by BMS at last to afford compound 26a and 26b. The configuration of 26a and 26b was determined to be (13S, 14aS) and (13R,14aS) respectively by comparing the coupling constant of H at C13 (J=2.8 Hz) and other chemical shifts with those of compound 13a and 13b.

The configuration of other compounds including compound 3a/3b, 9a/9b, 13a/13b, 19a/19b, 21a/21b, 24a/24b, and 25 was determined by NOESY experiments.

Selected compounds were tested against a panel of five cancer cell lines: A549 (lung), DU-145 (prostate), KB (nasopharyngeal), HCT-8 (colon), and SKBR (breast). GI$_{50}$'s were shown in Table 1.

For substitutions at C12 position of R-antofine, compound 8, 9a, and 9b showed a uniform decrease of cytotoxicity in the middle nM to low μM range, suggesting that C12 might not be a good place to introduce polar groups such as hydroxyl. The 12R isomer (9a) showed a relative higher (3-fold) activity compared with 12S isomer (9b), indicating the confirmation of the five-membered E-ring might be relevant to their anticancer activity.

For substitutions at C13 position of R-cryptopleurine, compound 12, 13a, and 13b showed potent anticancer activity in the low nM range with a rank order of 13b (13R)>12>13a (12S), although they were less potent than R-cryptopleurine.

For C12 position of R-cryptopleurine, compound 18, 19a, and 19b were found to have lower potency in comparison with cryptopleurine. Interestingly, compound 19a (12R isomer, lower nM range) still exhibited strong anticancer activity in vitro compared with 19b (12S isomer, low μM range).

In addition, we also performed a calculation of blood-brain barrier penetration ratio that might help predict their pharmacological behavior in vivo. As seen in Table 1, tylophorine has a much lower value than cryptopleurine and antofine, which is consistent with results from animal tests that tylophorine was generally non-toxic up to 500 mg/kg in rats, whereas cryptopleurine was quite toxic. This is possibly due to higher distribution in brain (predicted value=0.2814). All compounds except compound 8 shown herein exhibited reduced predicted value than cryptopleurine and antofine, some of which even had a value lower than tylophorine while still possessed strong anticancer activity in vitro such as compound 12, 13a, and 13b. And it is foreseeable that the BBB value could be further lowered if using tylophorine as the main scaffold to reduce potential CNS toxicity. Other structural modifications are still underway and results will be reported in due time.

Experimental Section (13R/S,13aS)-11-oxo-13-hydroxy-antofine (2a/2b)

Alcohol 1 (113 mg, 0.25 mmol) was dissolved in CH$_2$Cl$_2$ (10 mL) and Et$_3$N (0.14 mL, 1 mmol), to which Py.SO$_3$ (120

TABLE 1

GI$_{50}$'s of new polar phenanthroindolizidines and phenanthroquinolizidines

| Compound | A549 (μM) | DU145 (μM) | KB (μM) | KBvin (μM) | HCT-8 (μM) | SKBR (μM) | Predicted BBB penetration (C.brain/C.blood) |
| --- | --- | --- | --- | --- | --- | --- | --- |
| 3a | 2.81 | 3.20 | 1.83 | 3.42 | — | — | 0.0586 |
| 3b | 0.27 | 0.85 | 0.50 | 0.64 | — | — | 0.0586 |
| 7 | 5.97 | 10.30 | 12.00 | 2.64 | 3.56 | — | 0.0437 |
| 8 | 0.29 | 0.71 | 0.50 | 0.43 | — | — | 0.3344 |
| 9a | 0.61 | 0.70 | 0.78 | 0.64 | — | — | 0.0624 |
| 9b | 2.27 | 1.80 | 1.81 | 2.21 | — | — | 0.0624 |
| 12 | 0.028 | 0.045 | 0.050 | 0.043 | — | — | 0.0286 |
| 13a | 0.072 | 0.059 | 0.043 | 0.078 | — | 0.295 | 0.0591 |
| 13b | 0.022 | 0.011 | 0.023 | 0.025 | — | 0.072 | 0.0591 |
| 18 | 0.910 | 1.70 | 0.734 | 1.479 | — | 3.34 | 0.0778 |
| 19a | 0.082 | 0.066 | 0.033 | 0.045 | — | 0.348 | 0.1276 |
| 19b | 2.51 | 2.25 | 2.25 | 3.07 | — | 6.44 | 0.1276 |
| 21a | 0.01 | 0.033 | 0.025 | 0.025 | — | — | 0.1234 |
| 21b | 0.069 | 0.20 | 0.30 | 0.12 | — | — | 0.1234 |
| 24a | 0.55 | 0.60 | 0.84 | 2.17 | — | — | 0.0686 |
| 24b | 14.48 | 17.09 | 17.52 | 12.56 | — | — | 0.0686 |
| 25 | 0.99 | 0.77 | 0.92 | 0.87 | — | — | 0.1740 |
| 26a | 7.11 | 3.57 | 5.24 | 3.69 | — | — | 0.0418 |
| 26b | 0.025 | 0.056 | 0.10 | 0.066 | — | — | 0.0418 |
| R-cryptopleurine | 1.38 nM | 1.59 nM | 1.51 nM | — | 1.09 nM | — | 0.2814 |
| R-antofine | 0.022 | 0.025 | 0.036 | 0.025 | — | — | 0.9806 | mg, 0.75 mmol) in DMSO was added dropwise. The mixture was stirred for 1.5 h, to which 1N HCl was added. The organic layer was washed with sat. NaHCO$_3$ and brine, dried over MgSO$_4$. In another flask, ethyl acetate (30 µL, 0.30 mmol) was added to LiHMDs (0.33 mmol) in THF at −78° C. stirring for 1 h, to which the aldehyde in THF was added slowly. The mixture was stirred for 3 h until TLC indicated complete disappearance of the aldehyde. Sat. NH$_4$Cl was added to quench the reaction and most solvent was removed in vacuo. CH$_2$Cl$_2$ was added and the organic layer was washed with sat. NaHCO$_3$ and brine, dried over Na$_2$SO$_4$. The solvent was evaporated and the residue was dissolved in TFA/CH$_2$Cl$_2$, which was stirred for 1 h. After removal of TFA in vacuo, Et$_3$N (0.20 mL) and MeOH (10 mL) were added. The mixture was refluxed for 1 h. Chromatography using CH$_2$Cl$_2$/MeOH gave 56 mg (57% over four steps) of an inseparable mixture of 2a/2b in a ratio of 2:1 as a white solid. $^1$H NMR (400 MHz, CDCl$_3$): δ 7.87 (s, 1H), 7.85 (d, J=2.4 Hz, 1H), 7.80 (d, J=9.2 Hz, 1H), 7.63 (s, 0.5H), 7.54 (d, J=2.4 Hz, 0.52H), 7.31 (d, J=8.8 Hz, 0.55H), 7.22-7.19 (m, 2H), 7.15 (s, 0.51H), 6.76 (dd, J=9.2 Hz, J=2.4 Hz, 0.52H), 5.38 (d, J=17.2 Hz, 1H), 4.93 (d, J=17.6 Hz, 0.56H), 4.66 (m, 0.58H), 4.57 (d, J=17.2 Hz, 1H), 4.51 (m, 1H), 4.40 (d, J=17.6 Hz, 0.59H), 4.11 (s, 4.23H), 4.04 (s, 4.25H), 4.01 (s, 2.79H), 3.90 (s, 1.49H), 3.85-3.75 (m, 1.69H), 3.51 (dd, J=15.6 Hz, J=4.0 Hz, 1H), 3.40 (dd, J=16.0 Hz, J=11.2 Hz, 0.64H), 3.18-3.09 (m, 1.24H), 2.94 (dd, J=17.6 Hz, J=7.2 Hz, 1H), 2.88 (dd, J=6.4 Hz, J=17.6 Hz, 0.50H), 2.74 (dd, J=15.2 Hz, J=11.2 Hz, 1H), 2.66 (d, J=18.0 Hz, 0.60H), 2.59 (dd, J=17.6 Hz, J=2.4 Hz, 1H); ESI MS m/z 394.10 (M+H)$^+$.

(13S,13aS)-13-hydroxyl-antofine (3a) and (13aS, 13R)-13-hydroxyl-antofine (3b)

Compound 2a/2b (56 mg) were suspended in THF and LiAlH$_4$ (20 mg, 0.50 mmol) was added. The mixture was stirred at room temperature for 1 h. Water and 1N NaOH were then added and the mixture was filtered. CH$_2$Cl$_2$ was used for extraction for normal workup. Chromatography using CH$_2$Cl$_2$/MeOH gave 27 mg of 3a (48%) and 12 mg (22%) of 3b as white solids. For 3a: $^1$H NMR (400 MHz, CDCl$_3$): δ 7.88 (d, J=2.8 Hz, 1H), 7.79 (s, 1H), 7.76 (d, J=9.2 Hz, 1H), 7.17 (dd, J=9.2 Hz, J=2.4 Hz, 1H), 6.77 (s, 1H), 4.67 (d, J=14.8 Hz, 1H), 4.32 (m, 1H), 4.10 (s, 3H), 4.02 (s, 3H), 3.66 (s, 3H), 3.58 (d, J=15.2 Hz, 1H), 3.51 (dt, J=8.8 Hz, J=2.4 Hz, 1H), 3.11 (dd, J=16.0 Hz, J=11.2 Hz, 1H), 2.93 (dd, J=16.0 Hz, J=3.2 Hz, 1H), 2.46-2.40 (m, 1H), 2.36-2.26 (m, 2H), 1.93-1.88 (m, 1H); ESI MS m/z 380.15 (M+H)$^+$. For 3b: $^1$H NMR (400 MHz, CDCl$_3$): δ 7.88-7.87 (m, 2H), 7.77 (d, J=9.2 Hz, 1H), 7.29 (s, 1H), 7.19 (dd, J=9.2 Hz, J=2.4 Hz, 1H), 4.58 (d, J=15.2 Hz, 1H), 4.35-4.30 (m, 1H), 4.09 (s, 3H), 4.04 (s, 3H), 4.01 (s, 3H), 3.74 (d, J=14.8 Hz, 1H), 3.47 (dd, J=15.6 Hz, J=2.8 Hz, 1H), 3.37 (dt, J=8.8 Hz, J=2.4 Hz, 1H), 2.96 (dd, J=15.2 Hz, J=11.2 Hz, 1H), 2.72 (q, J=9.2 Hz, 1H), 2.50-2.44 (m, 2H), 1.83-1.76 (m, 1H); ESI MS m/z 380.05 (M+H)$^+$.

(S)—N-2'-methoxypropenoyl-6,7,10-trimethoxy-3-vinyl-1,3,4-trihydrodibenzo[f,h]-isoquinoline (5)

Compound 4 (900 mg, 2 mmol) was dissolved in TFA/CH$_2$Cl$_2$ (20 mL) at r.t., and the mixture was stirred for 1 h. The solvent was removed by evaporation and TFA was neutralized with NMM. The residue was redissolved in DMF (20 mL), to which 2-methoxyacrylic acid (224 mg, 2.20 mmol), EDC hydrochloride (478 mg, 2.50 mmol), HOBt (340 mg, 2.50 mmol), NMM (0.80 mL) were added. Stirring was continued overnight. DMF was then removed under reduced pressure, and the residue was dissolved in CH$_2$Cl$_2$ (50 mL), washed with HCl (1N), sat. NaHCO$_3$, and brine, and dried over MgSO$_4$. 727 mg (83%) of compound 5 was isolated over two steps by column chromatography eluting with EtOAc/Hexane. mp 74-76° C.; [α]$^{23}_D$=71.5° (c 1.16, CHCl$_3$); $^1$H NMR (400 MHz, CDCl$_3$, compound rotameric at rt): δ 7.89-7.84 (m, 3H), 7.28 (s, 1H), 7.21 (dd, J=9.2 Hz, J=2.8 Hz, 1H), 5.88-5.61 (m, 2H), 5.20-5.10 (m, 3H), 4.64 (d, J=3.2 Hz, 1H), 4.54 (m, 1H), 4.46 (d, J=3.2 Hz), 4.09 (s, 3H), 4.05 (s, 3H), 4.00 (s, 3H), 3.73 (s, 3H), 3.43-3.28 (m, 2H); $^{13}$C NMR (100 MHz, CDCl$_3$): δ 165.9, 162.6, 157.9, 157.2, 149.7, 148.8, 135.9, 130.4, 126.5, 124.3, 123.8, 123.7, 123.3, 117.7, 115.2, 105.0, 104.1, 103.9, 56.1, 56.0, 55.6, 55.3, 53.8, 39.6, 36.5, 31.5, 30.3; ESI-HRMS ([M+H]$^+$) calcd for C$_{26}$H$_{27}$NO$_5$ 433.1889. found 434.1963.

(S)-11-oxo-12-methoxy-antofine-12-ene (6)

Compound 5 (727 mg, 1.66 mmol) was dissolved in anhydrous CH$_2$Cl$_2$ under N$_2$, to which Grubb's 2$^{nd}$ generation catalyst in CH$_2$Cl$_2$ was added in one portion. The reaction was stirred at reflux for 2 h or monitored by TLC. Compounds 6 (596 mg) was isolated by column chromatography eluting with CH$_2$Cl$_2$/MeOH as a light yellow solid. Yield: 88%. mp 135-137° C.; [α]$^{23}_D$=−235° (c 1.11, CHCl$_3$); $^1$H NMR (400 MHz, CDCl$_3$): δ 7.80 (s, 1H), 7.79 (d, J=2.8 Hz, 1H), 7.72 (d, J=8.8 Hz, 1H), 7.20-7.17 (m, 2H), 6.00 (d, J=2.4 Hz, 1H), 5.37 (d, J=17.6 Hz, 1H), 4.65 (d, J=17.2 Hz, 1H), 4.16-4.12 (m, 1H), 4.10 (s, 3H), 4.03 (s, 3H), 4.00 (s, 3H), 3.86 (s, 3H), 3.52 (dd, J=11.6 Hz, J=4.8 Hz, 1H), 2.53 (dd, J=15.6 Hz, J=11.6 Hz, 1H); $^{13}$C NMR (100 MHz, CDCl$_3$): δ 163.9, 158.0, 153.1, 149.5, 148.7, 130.4, 126.0, 124.1, 124.0, 123.2, 123.2, 122.4, 115.3, 108.7, 104.9, 104.0, 103.9, 57.5, 56.1, 56.0, 55.6, 52.4, 40.4, 31.4; ESI-HRMS ([M+H]$^+$) calcd for C$_{24}$H$_{23}$NO$_5$ 405.1567. found 406.1667.

(S)-12-methoxy-antofine-12-ene (7)

The amide 6 (450 mg, 1.11 mmol) and LiAlH$_4$ (2 equiv.) were suspended in THF (15 mL), which was stirred for 2 h. Water was then added to quench the reaction, followed by aq. NaOH (1N, 1 mL) and H$_2$O (1 mL). The mixture was filtered and then extracted with CHCl$_3$ and dried over MgSO$_4$. Column chromatography eluting with CH$_2$Cl$_2$/MeOH gave the target product 7 (300 mg) as a light yellow solid. Yield: 69%. mp 202-204° C.; [α]$^{23}_D$=−97.0° (c 0.47, CHCl$_3$); $^1$H NMR (400 MHz, CDCl$_3$): δ 7.91 (s, 1H), 7.90 (d, J=2.4 Hz, 1H), 7.80 (d, J=8.8 Hz, 1H), 7.33 (s, 1H), 7.20 (dd, J=9.2 Hz, J=2.4 Hz, 1H), 4.83 (s, 1H), 4.52 (d, J=14.4 Hz, 1H), 4.10 (s, 3H), 4.06 (s, 3H), 4.05 (d, J=14.4 Hz, 1H), 4.01 (s, 3H), 3.83 (d, J=7.2 Hz, 1H), 3.72 (s, 3H), 3.58 (m, 2H), 3.32 (d, J=15.2 Hz, 1H), 3.02 (m, 1H); $^{13}$C NMR (100 MHz, CDCl$_3$): δ 159.7, 157.7, 149.6, 148.6, 130.2, 127.7, 127.6, 125.8, 124.5, 124.4, 123.7, 115.1, 104.8, 104.3, 104.0, 95.3, 63.7, 57.8, 57.0, 56.2, 56.0, 55.7, 51.8, 33.8; ESI-HRMS ([M+H]$^+$) calcd for C$_{24}$H$_{25}$NO$_4$ 391.1784. found 392.1865.

(S)-12-oxo-antofine (8)

Compound 7 (300 mg) was refluxed in HCl/THF for 2 h before the solvent was evaporated. NaOH was used for neutralization and CH$_2$Cl$_2$ used for extraction. Chromatography gave 200 mg of compound 8 as a light yellow solid (68%). mp 240-242° C.; [α]$^{23}_D$=−34.7° (c 0.91, CHCl$_3$); IR (FT-IR ATR, cm$^{-1}$) 2833, 1751, 1609, 1510, 1260, 1234, 1208, 1202, 1126, 867, 777; $^1$H NMR (400 MHz, CDCl$_3$): δ 7.92 (s, 1H), 7.91 (d, J=2.4 Hz, 1H), 7.78 (d, J=8.8 Hz, 1H), 7.27 (s, 1H), 7.22 (dd, J=9.2 Hz, J=2.6 Hz, 1H), 4.70 (d, J=14.8 Hz, 1H), 4.11 (s, 3H), 4.06 (s, 3H), 4.02 (s, 3H), 3.84 (d, J=15.2 Hz, 1H), 3.78 (d, J=16.8 Hz, 1H), 3.43 (d, J=13.2 Hz, 1H), 3.07-3.01 (m, 2H), 2.98 (d, J=16.4 Hz, 1H), 2.76 (dd, J=17.6 Hz, J=5.2 Hz, 1H), 2.43 (dd, J=17.6 Hz, J=10.0 Hz, 1H); $^{13}$C NMR (100 MHz, CDCl$_3$): δ 212.4, 157.7, 149.5, 148.6, 130.2, 126.6, 125.7, 124.5, 124.0, 123.7, 123.6, 115.1, 104.7, 103.8, 103.7, 63.1, 57.9, 56.0, 55.9, 53.4, 44.7, 33.2; ESI-HRMS ([M+H]$^+$) calcd for C$_{23}$H$_{23}$NO$_4$ 377.1627. found 378.1704.

(12R,13aS)-12-hydroxyl-antofine (9a) and (12S,13aS)-12-hydroxyl-antofine (9b)

The ketone 8 (38 mg, 0.10 mmol) was suspended in MeOH, to which NaBH$_4$ (19 mg, 0.50 mmol) was added at r.t. The mixture was stirred for 1 h before sat. NaHCO$_3$ was added. After normal workup, chromatography using MeOH/CH$_2$Cl$_2$ gave 19 mg of 9a (50%) and 12 mg of 9b (31%) as white solids. For 9a: $^1$H NMR (400 MHz, CDCl$_3$): δ 7.85 (s, 2H), 7.69 (d, J=9.2 Hz, 1H), 7.18 (s, 1H), 7.12 (dd, J=9.2 Hz, J=2.4 Hz, 1H), 4.57 (d, J=14.8 Hz, 1H), 4.41 (m, 1H), 4.09 (s, 3H), 3.99 (s, 6H), 3.57 (d, J=14.8 Hz, 1H), 3.33 (d, J=10.4 Hz, 1H), 3.26 (dd, J=15.6 Hz, J=2.8 Hz, 1H), 2.88 (dd, J=15.2 Hz, J=10.8 Hz, 1H), 2.75-2.68 (m, 1H), 2.54-2.50 (m, 1H), 2.42-2.38 (m, 1H), 1.74-1.68 (m, 1H); ESI MS m/z 380.05 (M+H)$^+$. For 9b: $^1$H NMR (400 MHz, CDCl$_3$): δ 7.92 (s, 1H), 7.90 (d, J=2.4 Hz, 1H), 7.80 (d, J=9.2 Hz, 1H), 7.30 (s, 1H), 7.21 (dd, J=9.2 Hz, J=2.8 Hz, 1H), 4.65 (m, 1H), 4.63 (d, J=14.8 Hz, 1H), 4.06 (s, 3H), 4.02 (s, 3H), 3.86-3.80 (m, 2H), 3.41 (m, 1H), 3.35 (d, J=14.8 Hz, 1H), 2.95-2.83 (m, 2H), 2.49 (dd, J=10.0 Hz, J=4.8 Hz, 1H), 2.20-2.05 (m, 2H); ESI MS m/z 380.00 (M+H)$^+$.

(S)—N-Boc-6,7,10-trimethoxy-3-vinylcarbonylmethyl-1,3,4-trihydrodibenzo[f,h]isoquinoline (11)

Compound 10 (700 mg, 1.50 mmol) was dissolved in THF (20 mL), to which vinylmagnesium bromide (3.50 mL, 3.50 mmol) was added dropwise at 0° C. After 2 h of stirring, sat. NH$_4$Cl was added to quench the reaction and the mixture was extracted with CH$_2$Cl$_2$. The organic layers were washed with aq. NaHCO$_3$ and brine, dried over Na$_2$SO$_4$. Then the mixture was evaporated and the residue was redissolved in anhydrous CH$_2$Cl$_2$. Dess-Martine periodinane (848 mg, 2 mmol) was added and the reaction mixture was stirred for 4 h. Na$_2$S$_2$O$_3$ (500 mg) was added followed by sat. NaHCO$_3$, which was stirred for 10 min. The mixture was extracted with CH$_2$Cl$_2$ and the organic layers were combined and washed with brine, dried over MgSO$_4$. The solvent was removed and the crude was chromatographed using EtOAc/hexane to give 11 (434 mg, 57%) as a light yellow foam. $^1$H NMR (400 MHz, CDCl$_3$, peak broadened due to rotamers at r.t.): δ 7.87 (brs, 3H), 7.22 (brs, 2H), 6.30 (dd, J=17.2 Hz, J=10.4 Hz, 1H), 6.13 (d, J=17.6 Hz, 1H), 5.77 (d, J=6.8 Hz, 1H), 5.27 (m, 2H), 4.61 (m, 1H), 4.08 (s, 3H), 4.02 (s, 3H), 4.00 (s, 3H), 3.32 (dd, J=16.4 Hz, J=6.0 Hz, 1H), 3.15 (brs, 1H), 2.85-2.75 (m, 2H), 1.53 (s, 9H); ESI MS m/z 492.20 (M+H)$^+$.

(S)-13-oxo-cryptopleurine (12)

To a solution of TFA in CH$_2$Cl$_2$ was added compound 11 (245 mg, 0.50 mmol), which was stirred for 1 h before the solvent was removed in vacuo. Then the residue was dissolved in CH$_2$Cl$_2$ (5 mL) and MeOH (20 mL), to which Cs$_2$CO$_3$ (326 mg, 1 mmol) was added in one portion. The mixture was refluxed overnight. After evaporation of the solvent, the crude was chromatographed using CH$_2$Cl$_2$/MeOH to afford 12 (123 mg, 63%) as a light yellow solid. $^1$H NMR (400 MHz, CDCl$_3$): δ 7.81-7.80 (m, 2H), 7.68 (d, J=9.2 Hz, 1H), 7.16 (dd, J=8.8 Hz, J=2.4 Hz, 1H), 7.04 (s, 1H), 4.42 (d, J=15.6 Hz, 1H), 4.06 (s, 3H), 4.00 (s, 3H), 3.98 (s, 3H), 3.54 (dd, J=15.6 Hz, 1H), 3.43-3.38 (m, 1H), 2.87 (dd, J=16.0 Hz, J=3.2 Hz, 1H), 2.81-2.73 (m, 2H), 2.61-2.40 (m, 5H); ESI MS m/z 392.10 (M+H)$^+$.

(13S,14aS)-13-hydroxyl-eryptopleurine (13a) and (13R,14aS)-13-hydroxyl-cryptopleurine (13b)

To a solution of compound 12 (39 mg, 0.10 mmol) in MeOH was added NaBH$_4$ (19 mg, 0.50 mmol). The reaction mixture was stirred for 2 h before sat. NaHCO$_3$ was added. The mixture was then extracted using CH$_2$Cl$_2$ and the organic layers were washed with brine, dried over Na$_2$SO$_4$. The crude was chromatographed using MeOH/CH$_2$Cl$_2$ to give 13a (9 mg, 24%) and 13b as white solids (21 mg, 55%). The diastereoselectivity was further increased using L-selectride in THF at 0° C. to give 13a/13b in a ratio of 1/9. For 13a: $^1$H NMR (300 MHz, CDCl$_3$): δ 7.89-7.88 (m, 2H), 7.75 (d, J=9.0 Hz, 1H), 7.34 (s, 1H), 7.20 (dd, J=9.0 Hz, J=2.1 Hz, 1H), 4.43 (d, J=15.6 Hz, 1H), 4.07 (s, 3H), 4.04 (s, 3H), 3.99 (s, 3H), 3.69 (m, 1H), 3.54 (d, J=15.6 Hz, 1H), 3.26 (m, 1H), 3.02 (m, 1H), 2.89 (m, 1H), 2.42-2.59 (m, 3H), 2.07 (m, 1H), 1.72 (m, 1H); ESI MS m/z 394.05 (M+H)$^+$. For 13b: $^1$H NMR (300 MHz, CDCl$_3$): δ 7.90 (s, 1H), 7.89 (d, J=2.7 Hz, 1H), 7.80 (d, J=9.0 Hz, 1H), 7.23 (s, 1H), 7.19 (dd, J=9.0 Hz, J=2.4 Hz, 1H), 4.46 (d, J=15.6 Hz, 1H), 4.29 (m, 1H), 4.10 (s, 3H), 4.05 (s, 3H), 4.01 (s, 3H), 3.72 (d, J=15.3 Hz, 1H), 3.08-3.04 (m, 2H), 2.86-2.72 (m, 2H), 2.15-2.03 (m, 2H), 1.90-1.74 (m, 2H); ESI MS m/z 394.05 (M+H)$^+$.

(S)—N-Boc-6,7,10-trimethoxy-3-(3'-propenyl)-1,3,4-trihydrodibenzo[f,h]isoquinoline (14)

To a solution of Ph$_3$P=CH$_2$Br (1.43 g, 4 mmol) in THF was added n-BuLi (2M in heptanes, 1.95 mL) at 0° C. under N$_2$. The mixture was stirred for 0.5 h before compound 8 (970 mg, 2.08 mmol) in THF (10 mL) was added dropwise. The mixture was then stirred for 2 h (monitored by TLC). Sat. NH$_4$Cl was added to quench the reaction and THF was removed by evaporation. The residue was dissolved in CH$_2$Cl$_2$, washed with sat. NaHCO$_3$ and brine, and dried over MgSO$_4$. Column chromatography eluting with EtOAc/Hexane gave 9 (820 mg, 85%) as a light yellow foam. $^1$H NMR (400 MHz, CDCl$_3$, peak broadened due to rotamers at r.t.): δ 7.92-7.87 (m, 3H), 7.27-7.23 (m, 2H), 5.89-5.83 (m, 1H), 5.34 (brs, 1H), 5.05-4.79 (m, 3H), 4.53 (d, J=17.2 Hz, 1H), 4.11 (s, 3H), 4.04 (s, 3H), 4.02 (s, 3H), 3.26 (dd, J=16.0 Hz, J=2.0 Hz, 1H), 3.10 (d, J=16.4 Hz, 1H), 2.41-2.33 (m, 1H), 2.21-2.18 (m, 1H), 1.54 (s, 9H); ESI MS m/z 464.20 (M+H)$^+$, 486.10 (M+Na)$^+$.

(S)—N-2'-methoxypropenoyl-6,7,10-trimethoxy-3-(3'-propenyl)-1,3,4-trihydrodibenzo[f,h]isoquinoline (15)

Similar procedures as compound 5. Yield: 77% over two steps. $^1$H NMR (400 MHz, CDCl$_3$, peak broadened due to rotamers at r.t.): δ 7.93-7.70 (m, 3H), 7.25-7.22 (m, 2H), 5.84-5.76 (m, 1H), 5.68 (d, J=18.0 Hz, 1H), 5.34-5.16 (m, 0.65H), 5.07 (d, J=10.4 Hz, 1H), 5.01 (d, J=17.2 Hz, 1H), 4.77 (d, J=16.8 Hz, 0.29H), 4.61-4.40 (m, 3H), 4.10 (s, 3H), 4.04 (s, 3H), 4.01 (s, 3H), 3.31 (dd, J=16.0 Hz, J=4.8 Hz, 1H), 3.14 (d, J=15.6 Hz, 1H), 2.48-2.41 (m, 1H), 2.29-2.25 (m, 1H); ESI MS m/z 448.10 (M+H)$^+$.

(R)-11-oxo-12-methoxy-cryptopleurine-12-ene (16)

Similar procedures as compound 6. Yield: 65%. $^1$H NMR (400 MHz, CDCl$_3$): δ 7.89 (d, J=8.8 Hz, 1H), 7.85 (s, 1H), 7.84 (d, J=2.4 Hz, 1H), 7.22 (dd, J=9.2 Hz, J=2.4 Hz, 1H), 7.16 (s, 1H), 5.73 (d, J=17.2 Hz, 1H), 5.38 (t, J=4.8 Hz, 1H), 4.62 (d, J=17.2 Hz, 1H), 4.16-4.12 (m, 1H), 4.08 (s, 3H), 4.03 (s, 3H), 4.00 (s, 3H), 3.95-3.90 (m, 1H), 3.66 (s, 3H), 3.24 (dd, J=16.0 Hz, J=11.6 Hz, 1H), 3.00 (dd, J=16.0 Hz, J=2.8 Hz, 1H), 2.94 (ddd, J=17.2 Hz, J=8.0 Hz, J=4.0 Hz, 1H), 2.52 (dt, J=17.2 Hz, J=5.2 Hz, 1H); ESI MS m/z 420.10 (M+H)$^+$.

(R)-12-methoxy-cryptopleurine-12-ene (17)

Similar procedures as compound 7. Yield: 70%. $^1$H NMR (400 MHz, CDCl$_3$): δ 7.90 (s, 1H), 7.89 (d, J=2.4 Hz, 1H), 7.79 (d, J=9.2 Hz, 1H), 7.26 (s, 1H), 7.19 (dd, J=9.2 Hz, J=2.4 Hz, 1H), 4.71 (m, 1H), 4.47 (d, J=16.0 Hz, 1H), 4.10 (s, 3H), 4.06 (d, J=16.0 Hz, 1H), 4.05 (s, 3H), 4.00 (s, 3H), 3.58 (s, 3H), 3.44 (d, J=16.0 Hz, 1H), 3.28 (dd, J=15.6 Hz, J=1.6 Hz, 1H), 3.21-3.14 (m, 2H), 3.00-2.94 (m, 1H), 2.49-2.45 (m, 1H), 2.33-2.27 (m, 1H); ESI MS m/z 406.10 (M+H)$^+$.

(R)-12-oxo-cryptopleurine (18)

Similar procedures as compound 8. Yield: 80%. $^1$H NMR (400 MHz, CDCl$_3$): δ 7.90 (s, 1H), 7.89 (d, J=2.4 Hz, 1H), 7.73 (d, J=9.2 Hz, 1H), 7.22 (s, 1H), 7.19 (dd, J=9.2 Hz, J=2.4 Hz, 1H), 4.38 (d, J=15.6 Hz, 1H), 4.10 (s, 3H), 4.05 (s, 3H), 4.01 (s, 3H), 3.75 (d, J=15.6 Hz, 1H), 3.63 (dd, J=14.8 Hz, J=1.2 Hz, 1H), 3.19 (dd, J=16.0 Hz, J=2.4 Hz, 1H), 3.10 (d, J=14.8 Hz, 1H), 2.93 (dd, J=16.0 Hz, J=10.0 Hz, 1H), 2.87-2.82 (m, 1H), 2.68-2.63 (m, 1H), 2.52-2.44 (m, 1H), 2.36-2.29 (m, 1H), 2.00-1.91 (m, 1H); ESI MS m/z 392.05 (M+H)$^+$.

(12R,14aR)-12-hydroxyl-cryptopleurine (19a) and (12S,14aR)-12-hydroxyl-cryptopleurine (19b)

The ketone 18 (39 mg, 0.10 mmol) was suspended in MeOH, to which NaBH$_4$ (19 mg, 0.50 mmol) was added at r.t. The mixture was stirred for 1 h before sat. NaHCO$_3$ was added. After normal workup, chromatography using MeOH/CH$_2$Cl$_2$ gave 23 mg of 19a (58%) and 6 mg of 9b (15%) as white solids. The reaction can also be performed with L-selectride at 0° C. and only 19a was isolated (31 mg, 80%). For 19a: $^1$H NMR (400 MHz, CDCl$_3$): δ 7.89 (s, 1H), 7.88 (d, J=2.8 Hz, 1H), 7.76 (d, J=8.8 Hz, 1H), 7.23 (s, 1H), 7.20 (dd, J=9.2 Hz, J=2.4 Hz, 1H), 4.40 (d, J=15.2 Hz, 1H), 4.09 (s, 3H), 4.05 (s, 3H), 4.00 (s, 3H), 3.98-3.91 (m, 1H), 3.66 (d, J=15.2 Hz, 1H), 3.41-3.37 (m, 1H), 3.10 (dd, J=16.4 Hz, J=3.2 Hz, 1H), 2.82 (dd, J=16.4 Hz, J=10.0 Hz, 1H), 2.35-2.30 (m, 1H), 2.15 (t, J=10.4 Hz, 2H), 2.12-2.07 (m, 1H), 1.62-1.52 (m, 1H), 1.46-1.37 (m, 1H); ESI MS m/z 394.10 (M+H)$^+$. For 19b: $^1$H NMR (400 MHz, CDCl$_3$): δ 7.86 (s, 1H), 7.85 (d, J=2.4 Hz, 1H), 7.70 (d, J=9.2 Hz, 1H), 7.19 (s, 1H), 7.15 (dd, J=9.2 Hz, J=2.4 Hz, 1H), 4.30 (d, J=15.2 Hz, 1H), 4.09 (s, 3H), 4.08 (m, 1H), 4.04 (s, 3H), 4.00 (s, 3H), 3.55 (d, J=15.6 Hz, 1H), 3.26-3.23 (m, 1H), 3.05 (dd, J=16.4 Hz, J=3.2 Hz, 1H), 2.83 (dd, J=16.4 Hz, J=10.0 Hz, 1H), 2.43 (dd, J=12.0 Hz, J=1.6 Hz, 1H), 2.41-2.35 (m, 1H), 1.98-1.94 (m, 1H), 1.90-1.85 (m, 2H), 1.69-1.61 (m, 1H); ESI MS m/z 394.15 (M+H)$^+$.

(14R/S,14aS)-11-oxo-14-hydroxyl-cryptopleurine (20a/20b)

The preparation of the aldehyde was similar as compound 2a/2b. At −78° C. under N$_2$, to a solution of LiHMDs (1.5 mL, 1.50 mmol) in THF was added methyl propiolate (91 μL, 1.10 mmol) and the reaction mixture was stirred for 1 h. Then the aldehyde (~1 mmol) in 10 mL of THF was added dropwise in 5 min. The resulting mixture was continued to stir for 2 h before sat. NH$_4$Cl was added. The mixture was warmed to r.t. and CH$_2$Cl$_2$ was used for extraction. After routine workup, the residue was dissolved in MeOH and subject to catalytic hydrogenation using Pd/C (100 mg) at 50 psi for 2 h. The catalyst was filtered off and the solvent was evaporated under reduced pressure. Then the residue was dissolved in TFA/CH$_2$Cl$_2$ and stirred for 1 h before Et$_3$N (3 equiv.) and MeOH (15 mL) were added. The resulting mixture was refluxed for 2 h. At last, the mixture was chromatographed using MeOH/CH$_2$Cl$_2$ to give an inseperable mixture of 20a and 20b (191 mg, 47%) as white solids. $^1$H NMR (400 MHz, CDCl$_3$): δ 7.91-7.84 (m, 3H), 7.24-7.17 (m, 2H), 5.88 (d, J=17.2 Hz, 0.58H), 5.72 (d, J=17.2 Hz, 0.34H), 4.53-4.42 (d, J=18.0 Hz, 1H), 4.22 (m, 0.77H), 4.11 (s, 3H), 4.05 (s, 3H), 4.00 (s, 3H), 3.93-3.88 (m, 0.79H), 3.77-3.73 (m, 1H), 3.38 (dd, J=16.0 Hz, J=2.8 Hz, 1H), 2.95 (m, 1H), 2.84-2.71 (m, 1H), 2.61-2.48 (m, 1H), 2.27-2.20 (m, 1H), 2.10-2.02 (m, 11-1); ESI MS m/z 408.10 (M+H)$^+$.

(14S,14aS)-11-oxo-14-hydroxyl-cryptopleurine (21a) and (14R,14aS)-11-oxo-14-hydroxyl-cryptopleurine (21b)

The mixture 20a/20b (84 mg, 0.21 mmol) was suspended in THF (20 mL), to which borane-methyl sulfide (1.0 mL, 1.00 mmol) was added. The reaction mixture was stirred overnight before MeOH (5 mL) was added and warmed to reflux for 0.5 h. The mixture was chromatographed using MeOH/CH$_2$Cl$_2$ to afford 21a (14.4 mg) and 21b (18.8 mg) as white solids. Yield: 41%. For 21a: $^1$H NMR (400 MHz, CDCl$_3$): δ 7.90-7.89 (m, 2H), 7.78 (d, J=9.2 Hz, 1H), 7.29 (s, 1H), 7.19 (dd, J=8.8 Hz, J=2.4 Hz, 1H), 4.47 (d, J=15.6 Hz, 1H), 4.10 (s, 3H), 4.05 (s, 3H), 4.01 (s, 3H), 3.91 (br s, 1H), 3.67 (d, J=15.6 Hz, 1H), 3.53 (dd, J=16.4 Hz, J=10.4 Hz, 1H), 3.24-3.21 (m, 1H), 2.98 (dd, J=16.8 Hz, J=4.0 Hz, 1H), 2.61-2.57 (m, 2H), 2.34-2.28 (m, 1H), 2.10-2.03 (m, 2H), 1.69-1.66 (m, 1H); ESI MS m/z 394.10 (M+H)$^+$. For 21b: $^1$H NMR (400 MHz, CDCl$_3$): δ 7.90 (s, 1H), 7.89 (d, J=2.4 Hz, 1H), 7.77 (d, J=9.2 Hz, 1H), 7.31 (s, 1H), 7.19 (dd, J=9.2 Hz, J=2.4 Hz, 1H), 4.47 (d, J=15.6 Hz, 1H), 4.10 (s, 3H), 4.06 (s, 3H), 4.01 (s, 3H), 3.71-3.64 (m, 2H), 3.60 (dd, J=16.4 Hz, J=3.2 Hz, 1H), 3.22-3.19 (m, 1H), 2.96 (dd, J=16.4 Hz, J=9.2 Hz, 1H), 2.34-2.28 (m, 2H), 2.19-2.16 (m, 1H), 1.89-1.81 (m, 2H), 1.50-1.44 (m, 1H); ESI MS m/z 394.10 (M+H)$^+$.

(R,E)-N-Boc-3-(4-ethoxy-4-oxobut-2-enyl)-6,7,10-trimethoxy-3,4-dihydrodibenzo[f,h]isoquinoline (22)

To a solution of compound 10 (233 mg, 0.50 mmol) in CH$_2$Cl$_2$ (10 mL) was added Ph$_3$P=CH$_2$CO$_2$Et (348 mg, 1 mmol) in one portion. The reation mixture was stirred at 40° C. for 5 h. After normal workup, the residue was chromatographed using EtOAc/Hexane to give 238 mg of 22 as a light yellow foam in a yield of 89%. $^1$H NMR (400 MHz, CDCl$_3$, peak broadened due to rotamers at r.t.): δ 7.93-7.78 (m, 3H), 7.28-7.22 (m, 2H), 7.03-6.83 (m, 1H), 5.91-5.78 (d, J=15.6 Hz, 1H), 5.41-5.23 (m, 1H), 5.06-4.89 (m, 1H), 4.65-4.50 (d, J=16.8 Hz, 1H), 4.16 (q, J=7.2 Hz, 2H), 4.11 (s, 3H), 4.04 (s, 3H), 4.02 (s, 3H), 3.40-3.29 (dd, J=16.0 Hz, J=6.0 Hz, 1H), 3.09 (d, J=16.4 Hz, 1H), 2.57-2.50 (m, 1H), 2.34 (br s, 1H), 1.53 (s, 9H), 1.27 (t, J=7.2 Hz, 3H); ESI MS m/z 536.20 (M+H)$^+$, 558.30 (M+Na)$^+$.

(12S/13S,12R/13R,14aS)-11-oxo-12,13-dihydroxyl-eryptopleurine (23a/23b)

To a solution of amide 22 (238 mg, 0.44 mmol) in 15 mL of acetone and $H_2O$ (8:1) was sequentially added $OsO_4$ (2.5 wt % in t-BuOH, 0.05 mmol) and 4-methylmorpholine N-oxide (155 mg, 1.32 mmol). The reaction mixture was stirred at 50° C. for 6 h before excessive $Na_2S_2O_3$ was added to quench the reaction. The mixture was extracted by $CH_2Cl_2$ and washed with brine, dried over $Na_2SO_4$. The solvent was then removed in vacuo and 10 mL of TFA in $CH_2Cl_2$ (1:1) was added, and the mixture was stirred for 0.5 h. After that, the solvent was evaporated and the trace of TFA was neutralized by $Et_3N$. The residue was stirred in 10 mL of MeOH and 0.2 mL of $Et_3N$ for 2 h. Chromatography using MeOH/$CH_2Cl_2$ gave an inseperable mixture of 23a and 23b as a yellow solid (130 mg, yield: 67% over three steps, in about 5:4 ratio as indicated by NMR). $^1$H NMR (400 MHz, $CDCl_3$): δ 7.92-7.84 (m, 3H), 7.27-7.17 (m, 2H), 6.00 (d, J=17.2 Hz, 0.43H), 5.54 (d, J=18.0 Hz, 0.56H), 4.62 (d, J=18.0 Hz, 0.65H), 4.45 (d, J=17.2 Hz, 0.51H), 4.24 (m, 0.65H), 4.11 (s, 3H), 4.07 (s, 3H), 4.02 (m, 4H), 3.77 (m, 0.71H), 3.38 (dd, J=16.0 Hz, J=3.2 Hz, 1H), 2.97 (dd, J=16.4 Hz, J=10.8 Hz, 1H), 2.67-2.64 (m, 1H), 2.41-2.31 (m, 1H), 2.00 (m, 1H); ESI MS m/z 424.10 $(M+H)^+$.

(12S,13S,14aS)-12,13-dihydroxyl-cryptopleurine (24a) and (12R,13R,14aS)-12,13-dihydroxyl-cryptopleurine (24b)

Similar procedures as compound 21a and 21b. For 24a: $^1$H NMR (400 MHz, $CDCl_3$): δ 7.90 (s, 1H), 7.88 (d, J=2.4 Hz, 1H), 7.76 (d, J=9.2 Hz, 1H), 7.23 (s, 1H), 7.20 (dd, J=9.2 Hz, J=2.4 Hz, 1H), 4.48 (d, J=15.6 Hz, 1H), 4.10 (s, 3H), 4.06 (s, 3H), 4.01 (s, 3H), 3.83-3.77 (m, 1H), 3.71-3.68 (m, 1H), 3.65-3.59 (m, 1H), 3.43 (dd, J=11.2 Hz, J=4.4 Hz, 1H), 3.16 (dd, J=16.4 Hz, J=3.2 Hz, 1H), 2.90 (dd, J=16.4 Hz, J=10.0 Hz, 1H), 2.57-2.52 (m, 1H), 2.38-2.33 (m, 1H), 2.30 (t, J=10.4 Hz, 1H), 1.64 (q, J=12.0 Hz, 1H); ESI MS m/z 410.00 $(M+H)^+$. For 24b: $^1$H NMR (400 MHz, $CDCl_3$): δ 7.90 (s, 1H), 7.88 (d, J=2.4 Hz, 1H), 7.76 (d, J=9.2 Hz, 1H), 7.22 (s, 1H), 7.19 (dd, J=9.2 Hz, J=2.4 Hz, 1H), 4.37 (d, J=15.2 Hz, 1H), 4.10 (s, 3H), 4.08 (m, 1H), 4.06 (s, 3H), 4.00 (s, 3H), 3.83 (br s, 1H), 3.77 (d, J=15.6 Hz, 1H), 3.11 (dd, J=12.0 Hz, J=3.2 Hz, 1H), 3.04 (m, 1H), 2.93 (dd, J=12.0 Hz, J=1.6 Hz, 1H), 2.88-2.85 (m, 2H), 2.09-2.06 (m, 2H); ESI MS m/z 410.00 $(M+H)^+$.

(13R,14aS)-13-ethyl-13-hydroxyl-cryptopleurine (25)

To a solution of compound 12 (14 mg, 0.036 mmol) in THF was added EtMgBr (0.10 mL, 0.10 mmol) under $N_2$ at 0° C. The resulting mixture was stirred for 1 h before sat. $NH_4Cl$ was added to quench the reaction. $CH_2Cl_2$ was used for extraction. The organic layers were combined and washed with aq. $NaHCO_3$ and brine, dried over $Na_2SO_4$. The solvent was removed in vacuo and the residue was chromatographed using MeOH/$CH_2Cl_2$ to give 25 (7.8 mg, 51%) as a light yellow solid. $^1$H NMR (400 MHz, $CDCl_3$): δ 7.88 (s, 1H), 7.86 (d, J=2.4 Hz, 1H), 7.78 (d, J=8.8 Hz, 1H), 7.19 (s, 1H), 7.18 (dd, J=8.8 Hz, J=2.4 Hz, 1H), 4.46 (d, J=15.2 Hz, 1H), 4.09 (s, 3H), 4.03 (m, 1H), 3.99 (s, 3H), 3.66 (d, J=15.6 Hz, 1H), 3.12-3.08 (m, 1H), 3.01 (dd, J=16.0 Hz, J=2.4 Hz, 1H), 2.82 (dd, J=16.0 Hz, J=11.2 Hz, 1H), 2.75-2.69 (m, 2H), 1.96 (dt, J=10.2 Hz, J=2.8 Hz, 1H), 1.86 (dt, J=11.2 Hz, J=4.4 Hz, 1H), 1.72-1.68 (m, 1H), 1.59 (q, J=7.6 Hz, 2H), 1.55 (m, 1H), 1.01 (t, J=7.6 Hz, 3H); ESI MS m/z 422.00 $(M+H)^+$.

(13S,14aS)-13-methoxy-cryptopleurine (26a) and (13R,14aS)-13-methoxy-cryptopleurine (26b)

To a solution of LiHMDs (0.30 mmol) in THF under Ar was added EtOAc (25 μl, 0.25 mmol) in 1 mL of THF at −78° C. and the resulting mixture was stirred for 1 h before compound 10 (93 mg, 0.20 mmol) in 1 mL of THF was added slowly. The reaction mixture was stirred at −78° C. for about 2 h as indicated by TLC. Then sat. $NH_4Cl$ was added and the mixture was extracted with $CH_2Cl_2$, dried over $Na_2SO_4$. After the Boc group was removed by TFA, the residue was stirred in $Et_3N$/MeOH for 2 h and the intermediate was purified through a short column using MeOH/$CH_2Cl_2$ as elutant. The solvent was evaporated and the residue was redissolved in THF, to which NaH (20 mg) was added. The reaction mixture was stirred for 0.5 h followed by addition of $Me_2SO_4$ before the temperature was warmed to 50° C. The reaction was stopped according to TLC (about 1 h) and after normal workup, the mixture was dried over $Na_2SO_4$. At last, the solvent was removed in vacuo and the residue was redissolved in THF, to which BMS (0.2 mL, 0.20 mmol) was added. The mixture was stirred overnight and MeOH was used to quench the reaction in reflux. The mixture was purified using MeOH/$CH_2Cl_2$ as elutant to give 7.2 mg of 26a and 6.4 mg of 26b as light yellow solids in 17% yield over five steps. For 26a: $^1$H NMR (400 MHz, $CDCl_3$): δ 7.91 (s, 1H), 7.89 (d, J=2.4 Hz, 1H), 7.79 (d, J=9.2 Hz, 1H), 7.26 (s, 1H), 7.19 (dd, J=9.2 Hz, J=2.4 Hz, 1H), 4.49 (d, J=15.6 Hz, 1H), 4.10 (s, 3H), 4.06 (s, 3H), 4.01 (s, 3H), 3.60 (d, J=15.6 Hz, 1H), 3.44 (s, 3H), 3.39-3.30 (m, 2H), 3.14 (dd, J=16.4 Hz, J=3.2 Hz, 1H), 2.94 (dd, J=16.0 Hz, J=10.4 Hz, 1H), 2.47-2.31 (m, 3H), 2.21-2.17 (m, 1H), 1.76-1.66 (m, 1H), 1.54-1.46 (m, 1H); ESI MS m/z 408.10 $(M+H)^+$. For 26b: $^1$H NMR (400 MHz, $CDCl_3$): δ 7.91 (s, 1H), 7.89 (d, J=2.4 Hz, 1H), 7.79 (d, J=9.2 Hz, 1H), 7.24 (s, 1H), 7.19 (dd, J=9.2 Hz, J=2.4 Hz, 1H), 4.45 (d, J=15.2 Hz, 1H), 4.10 (s, 3H), 4.06 (s, 3H), 4.01 (s, 3H), 3.72 (d, J=16.0 Hz, 1H), 3.69 (m, 1H), 3.40 (s, 3H), 3.09-3.01 (m, 2H), 2.89-2.78 (m, 2H), 2.74-2.67 (m, 1H), 2.31-2.26 (m, 1H), 2.09-2.04 (m, 1H), 1.98-1.89 (m, 1H), 1.71-1.64 (m, 1H); ESI MS m/z 408.10 $(M+H)^+$.

References (1). Gellert, E. *J. Nat. Prod.* 1982, 45, 50-73.
(2). For reviews, see: (a). Li, Z.; Jin, Z.; Huang, R. *Synthesis* 2001, 16, 2365-2378. (b). Chemler, S. R. *Current Bioactive Compounds* 2009, 5, 2.
(3). Buckley, T. F.; Rapoport, H. *J. Org. Chem.* 1983, 48, 4222-4232.
(4). Nordlander, J. E.; Njoroge, F. G. *J. Org. Chem.* 1987, 52, 1627-1630.
(5). Furstner, A.; Kennedy, J. W. *J. Chem. Eur.* 12006, 12, 7398-7410.
(6). Jin, Z.; Li, S. P.; Wang, Q. M.; Huang, R. Q. *Chinese Chem. lefts* 2004, 15, 1164.
(7). Faber, L.; Wiegrebe, W. *Helv. Chim. Acta* 1976, 59, 2201-2212.
(8) (a) Comins, D. L.; Chen, X.; Morgan, L. A. *J. Org. Chem.* 1997, 62, 7435-7438. (b) Mara, M.; Takino, Y.; Tomotake, M.; Fukumoto, K. *J. Chem. Soc. perkin Trans.* 1990, 1, 2287-2292. (c) Suzuki, H.; Aoyagi, S.; Kibayashi, C. *J. Org. Chem.* 1995, 60, 6114-6122.
(9). Kim, S.; Lee, T.; Lee, E.; Lee, J.; Fan, G. J.; Lee, S. K.; Lee, D. *J. Org. Chem.* 2004, 69, 3144-3149.

(10). Zeng, W.; Chemler, S. R. *J. Org. Chem.* 2008, 73, 6045-6047.

(11). Kim, S. H.; Lee, J.; Lee, T.; Park, H. G.; Kim, D. *Org. Lett.* 2003, 5, 2703-2706.

(12). Suffness, M.; Douros, J. *Anticancer Agents Based on Natural Product Models*, Academic press 1980, 465-487.

(13) (a) Gao, W.; Busson, S.; Grill, S. P.; Gullen, E. A.; Hu, Y. C.; Huang, X.; Zhong, S.; kaczmarek, C.; Gutierrez, J.; Francis, S.; Baker, D. C.; Yu, S.; Cheng, Y. C. *Bioorg. & Med. Chem. Lett.* 2007, 17, 4338-4342. (b) Gao, W.; Lam, W.; Zhong, S.; kaczmarek, C.; Baker, D. C.; Cheng, Y. C. *Cancer Res.* 2004, 64, 678-688.

The foregoing is illustrative of the present invention, and is not to be construed as limiting thereof. The invention is defined by the following claims, with equivalents of the claims to be included therein.

What is claimed is:

1. A compound having a structure according to Formula IV:

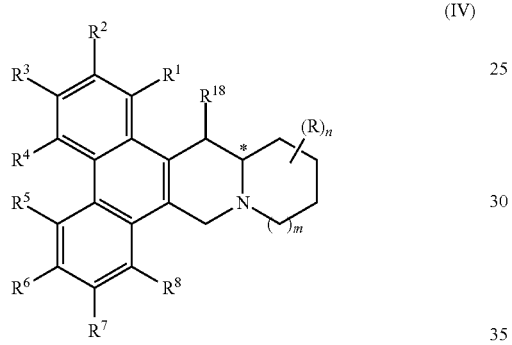

wherein:
n is 1 or 2;
m is 1;
each R is hydroxyl;
$R^1$, $R^2$, $R^3$, $R^4$, $R^5$, $R^6$, $R^7$ and $R^8$ are each independently selected from the group consisting of H and alkoxy;
subject to the proviso that at least one of $R^1$, $R^2$, $R^3$, $R^4$, $R^5$, $R^6$, $R^7$ and $R^8$ is an alkoxy;
$R^{18}$ is selected from the group consisting of H, hydroxyl, alkoxy, alkylthio, loweralkyl, loweralkenyl, loweralkynyl, alkoyl, loweralkoyl, loweralkenoyl and amino;
or a pharmaceutically acceptable salt thereof.

2. The compound of claim 1, wherein $R^{18}$ is H.

3. The compound of claim 2, selected from the group consisting of:

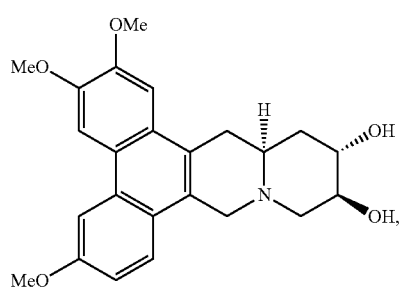
24a

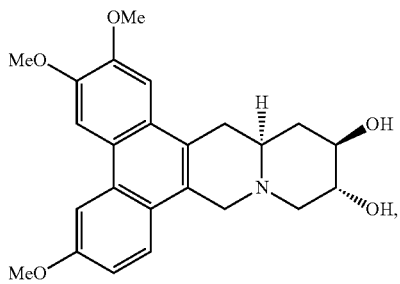
24b

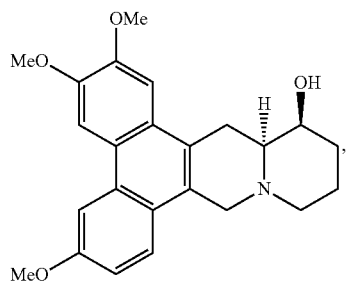
21a

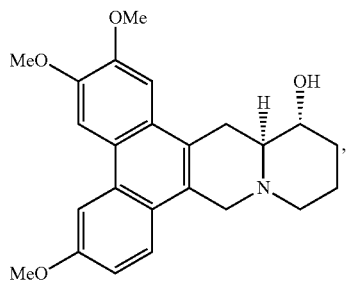
21b

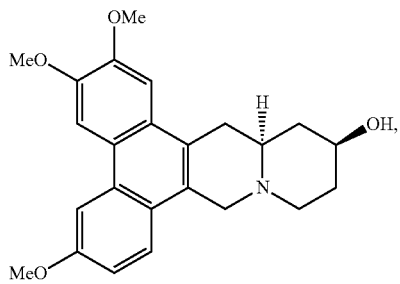
13a

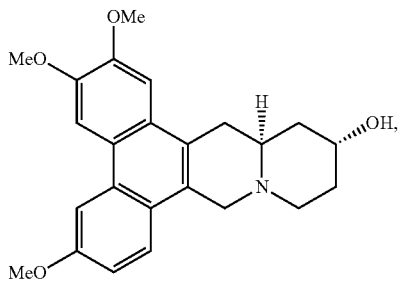
13b and pharmaceutically acceptable salts thereof.

4. A method of treating a cancer, comprising administering to a human or animal subject in need thereof a treatment effective amount of a compound of claim 3, or a pharmaceutically acceptable salt thereof, wherein said cancer is selected from the group consisting of breast cancer and lung cancer.

5. A composition comprising a compound of claim 3 in a pharmaceutically acceptable carrier.

6. A composition comprising a compound of claim 1 in a pharmaceutically acceptable carrier.

7. A method of treating a cancer, comprising administering to a human or animal subject in need thereof a treatment effective amount of a compound of claim 1, or a pharmaceutically acceptable salt thereof, wherein said cancer is selected from the group consisting of skin cancer, lung cancer, testicular cancer, lymphoma, leukemia, Kaposi's sarcoma, esophageal cancer, stomach cancer, colon cancer, breast cancer, endometrial cancer, ovarian cancer, liver cancer and prostate cancer.

8. The method of claim 7, wherein said cancer is breast cancer.

9. The method of claim 7, wherein said cancer is lung cancer.

10. The method of claim 7, wherein said cancer comprises multi-drug resistant cancer.

11. The method of claim 7, wherein said cancer comprises etoposide resistant cancer.

* * * * *